United States Patent
Yamakawa

(10) Patent No.: US 10,219,680 B2
(45) Date of Patent: Mar. 5, 2019

(54) ENDOSCOPIC SURGICAL DEVICE, OVERTUBE, AND EXTERIOR TUBE

(71) Applicant: FUJIFILM Corporation, Tokyo (JP)

(72) Inventor: Shinichi Yamakawa, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 241 days.

(21) Appl. No.: 15/058,175

(22) Filed: Mar. 2, 2016

(65) Prior Publication Data
US 2016/0235279 A1 Aug. 18, 2016

Related U.S. Application Data

(63) Continuation of application No. PCT/JP2014/072990, filed on Sep. 2, 2014.
(Continued)

(51) Int. Cl.
*A61B 1/00* (2006.01)
*A61B 1/313* (2006.01)
(Continued)

(52) U.S. Cl.
CPC ...... *A61B 1/00135* (2013.01); *A61B 1/00004* (2013.01); *A61B 1/00045* (2013.01);
(Continued)

(58) Field of Classification Search
CPC .... A61B 2017/3445; A61B 2017/3484; A61B 2017/349; A61B 17/348; A61B 1/00073; A61B 1/00075
(Continued)

(56) References Cited

U.S. PATENT DOCUMENTS 4,040,413 A * 8/1977 Ohshiro ............. A61B 1/00082 600/115
4,066,070 A * 1/1978 Utsugi ............... A61B 1/00082 600/115
(Continued)

FOREIGN PATENT DOCUMENTS

JP H10-075958 3/1998
JP 2003-061970 3/2003
(Continued)

OTHER PUBLICATIONS

"Written Opinion of the International Searching Authority of PCT/JP2014/072990", this report contains the following items: Form PCT/ISA237(cover sheet), PCT/ISA237(Box No. 1), PCT/ISA237(Box No. V) and PCT/ISA237(Box No. VI), dated Oct. 28, 2014, which is English translation of "Written Opinion of the International Searching Authority", pp. 1-8.

*Primary Examiner* — Timothy J Neal
*Assistant Examiner* — Aaron B Fairchild
(74) *Attorney, Agent, or Firm* — JCIPRNET

(57) ABSTRACT

The overtube includes a slider within an overtube body, which guides an endoscope and a treatment tool into a body cavity. An endoscope-coupled part and a treatment tool-coupled part are provided inside the slider, and the slider has a dead zone where the forward and backward movement of either the endoscope or the treatment tool does not interlock with the movement of the other and a sensing zone where the forward and backward movement of either the endoscope or the treatment tool interlocks with the movement of the other. A contact surface of the overtube body with a body wall is constituted of a wall surface member that serves as a rotation-preventing wall surface for preventing rotation in a rotational direction with an axial direction of the overtube body as a center.

21 Claims, 42 Drawing Sheets

Related U.S. Application Data

(60) Provisional application No. 61/873,206, filed on Sep. 3, 2013.

(51) Int. Cl.
| | | |
|---|---|---|
| *A61B 1/018* | (2006.01) | |
| *A61B 1/07* | (2006.01) | |
| *A61B 17/34* | (2006.01) | |
| *A61B 17/00* | (2006.01) | |
| *A61B 90/00* | (2016.01) | |
| *A61B 17/22* | (2006.01) | |

(52) U.S. Cl.
CPC ...... *A61B 1/00073* (2013.01); *A61B 1/00114* (2013.01); *A61B 1/00154* (2013.01); *A61B 1/018* (2013.01); *A61B 1/07* (2013.01); *A61B 1/3132* (2013.01); *A61B 17/3421* (2013.01); *A61B 17/3462* (2013.01); *A61B 90/37* (2016.02); *A61B 2017/0034* (2013.01); *A61B 2017/22074* (2013.01); *A61B 2017/3441* (2013.01); *A61B 2017/3445* (2013.01); *A61B 2017/3484* (2013.01)

(58) Field of Classification Search
USPC ....................................................... 600/115
See application file for complete search history.

(56) References Cited

U.S. PATENT DOCUMENTS

| | | | |
|---|---|---|---|
| 5,697,913 A | | 12/1997 | Sierocuk et al. |
| 6,004,302 A | * | 12/1999 | Brierley ............. A61F 9/00781 604/239 |
| 6,432,085 B1 | * | 8/2002 | Stellon ............... A61B 17/3421 604/164.04 |
| 2005/0119525 A1 | * | 6/2005 | Takemoto .......... A61B 1/00154 600/114 |
| 2005/0119685 A1 | | 6/2005 | Smith |
| 2007/0106319 A1 | | 5/2007 | Au et al. |
| 2010/0256447 A1 | * | 10/2010 | Dubi .................. A61B 1/00082 600/115 |
| 2011/0124960 A1 | | 5/2011 | St. Onge et al. |
| 2011/0230713 A1 | | 9/2011 | Kleemann et al. |
| 2015/0080650 A1 | | 3/2015 | Dejima et al. |

FOREIGN PATENT DOCUMENTS

| | | |
|---|---|---|
| JP | 2003-325436 | 11/2003 |
| JP | 2004-041580 | 2/2004 |
| JP | 2004-141486 | 5/2004 |
| JP | 2004-180858 | 7/2004 |
| JP | 2007-521846 | 8/2007 |
| JP | 2009-514651 | 4/2009 |
| JP | 2012-501695 | 1/2012 |
| WO | 2013/176167 | 11/2013 |

\* cited by examiner

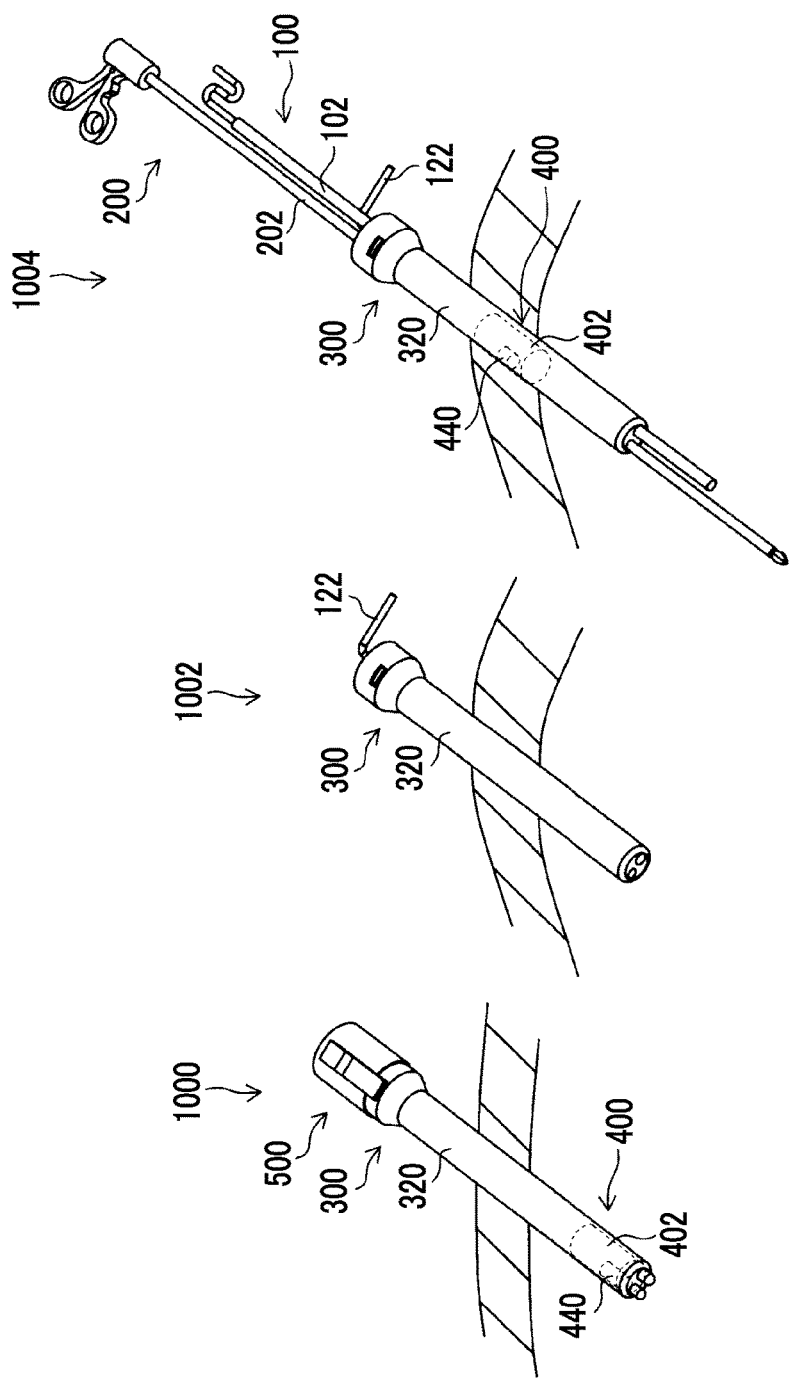

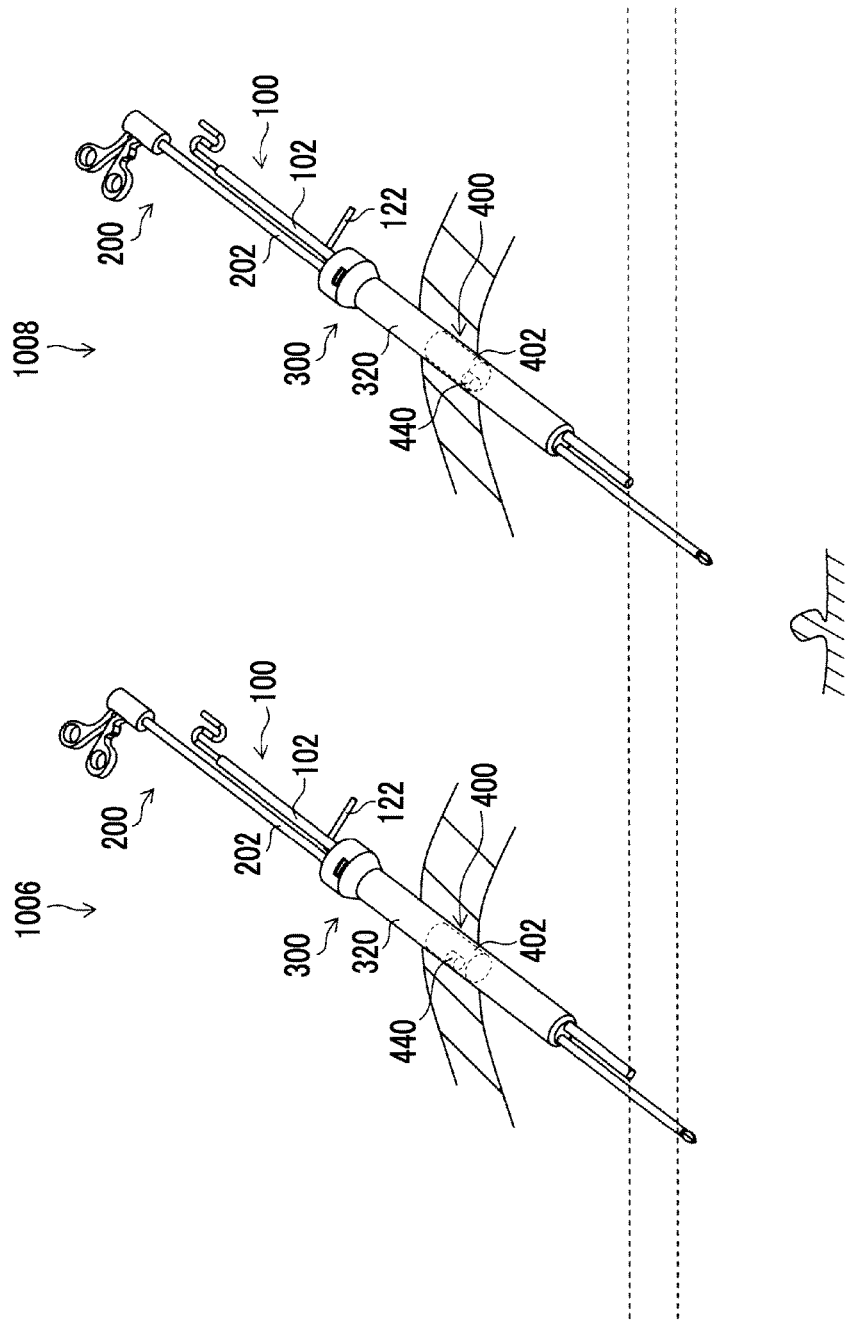

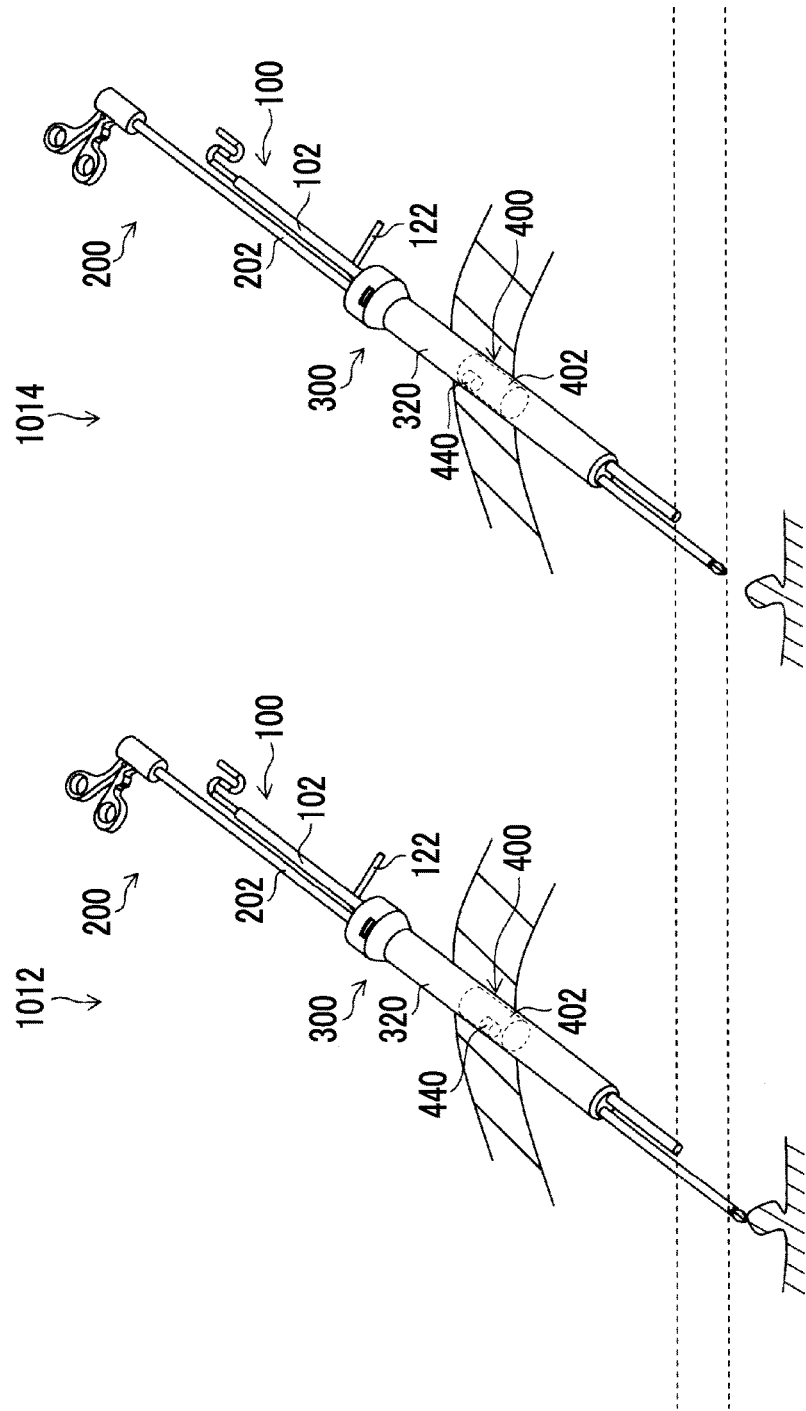

ENDOSCOPIC SURGICAL DEVICE, OVERTUBE, AND EXTERIOR TUBE

CROSS-REFERENCE TO RELATED APPLICATIONS

The present application is a Continuation of PCT International Application No. PCT/JP2014/072990 filed on Sep. 2, 2014 claiming priority under 35 U.S.C. § 119(a) of U.S. Provisional Applications 61/873,206 filed on Sep. 3, 2013. Each of the above applications is hereby expressly incorporated by reference, in their entirety, into the present application.

BACKGROUND OF THE INVENTION

1. Field of the Invention

The present invention relates to an endoscopic surgical device, a trocar (overtube), and a sleeve (exterior tube), and particularly, relates to an endoscopic surgical device, an overtube, and an exterior tube that can operate in a state where an endoscope and a treatment tool inserted into a body cavity are interlocked with each other.

2. Description of the Related Art

In the related art, the endoscopic surgery of inserting a treatment tool and an endoscope into a patient's body cavity and performing treatment work while observing, using the endoscope, the treatment state of an affected part using the treatment tool inserted into the body cavity has been known. In this surgery, in order for a surgeon to obtain a visual field where surgery is easy, the operation of changing the observation position of the endoscope is performed when necessary.

Generally, in the endoscopic surgery, a surgeon's hand is blocked due to the operation of the treatment tool, and the operation of changing the observation position of the endoscope is performed by an assistant called a scopist (endoscopic technician). For this reason, when the observation position of the endoscope is changed, the surgeon should serially give instructions to the assistant. Therefore, the work of correctly directing the orientation of the endoscope to a direction desired by the surgeon is difficult, and stress is likely to be imposed on the surgeon. Additionally, since the assistant performs an operation after the surgeon issues an instruction, there is a tendency that surgery time is likely to be prolonged. Additionally, the assistant should operate the endoscope so as not to interfere with a surgeon's procedure, and the operation is likely to become complicated.

In contrast, various techniques of interlocking the endoscope and the treatment tool have been suggested up to now (for example, refer to JP2004-141486A and JP2003-325436A).

An endoscopic surgery system that moves the treatment tool while following the fluctuation of the visual field of the endoscope is disclosed in JP2004-141486A. In this endoscopic surgery system, a treatment part of the treatment tool is kept from deviating from the visual field of the endoscope by detecting the movement distance (the rotational angle and the amount of insertion and extraction) of the endoscope in a state where the endoscope and the treatment tool have been inserted into an integral sheath (guide member), and controlling the movement distance (the rotational angle and the amount of insertion and extraction) of the treatment tool with respect to the sheath on the basis of the detection result.

Additionally, an endoscopic surgery device that changes the visual field of the endoscope while following the movement of the treatment tool inserted into the body cavity during the endoscopic surgery is disclosed in JP2003-325436A. This endoscopic surgery device is provided by mechanically coupling the treatment tool to a distal end part of the endoscope to integrally move the treatment tool and the distal end part of the endoscope to move the observation optical axis of the endoscope in a direction in which the treatment tool moves.

Additionally, various techniques for fixing, to a body wall, an overtube, which guides a medical instrument, such as an endoscope or a treatment tool, into the body cavity have been proposed up to now (for example, refer to JP2003-61970A and JP2009-514651A).

SUMMARY OF THE INVENTION

Under the above background, in the endoscopic surgery, it is desired that the visual field of the endoscope can be easily changed while the surgeon operates the treatment tool without asking for an assistant's help.

However, the endoscopic surgery system disclosed in JP2004-141486A does not mechanically interlock the endoscope with the treatment tool, and has a problem in which a mechanism for performing interlocking control of the endoscope and the treatment tool is easily enlarged and complicated. Additionally, this endoscopic surgery system moves the treatment tool while following the movement of the endoscope, and does not move the endoscope while following the movement of the treatment tool. For this reason, there are problems in that it is necessary to ask for an assistant's help in order to change the visual field of the endoscope, the operation for changing the observation position of the endoscope according to a surgeon's intention easily becomes complicated, and the surgery time is easily prolonged.

Additionally, since the endoscopic surgery device disclosed in JP2003-325436A has a configuration in which the endoscope and the treatment tool are mechanically coupled and always move integrally, the visual field of the endoscope also changes minutely in an interlocking manner with minute movement of the treatment tool. For this reason, there is a problem in that an observation image obtained by the endoscope moves minutely and is hardly seen. Particularly when the endoscope and the treatment tool are inserted into the body cavity in a parallel state, there is a problem in which the size of an object to be observed changes in an interlocking manner with the minute movement of the treatment tool, and a sense of perspective cannot be easily held.

Additionally, in ordinary overtubes, only one insertion passage for guiding the medical instrument, such as an endoscope or a treatment tool, into the body cavity is provided, and the medical instrument inserted through the insertion passage is movable forward and backward in an axial direction and is brought into a rotatable state in a rotational direction with an axial direction as a center. For this reason, even if an overtube inserted into a body wall rotates, the treatment tool does not rotate. Additionally, if the treatment tool is rotated, even if the treatment tool co-rotates with the rotation of the overtube, the treatment tool can be returned to its original state, and the rotational operation of the treatment tool is a simple operation for the surgeon.

In contrast, if the overtube rotates in the rotational direction with the axial direction as the center in the case of a configuration in which a plurality of insertion passages are provided inside the overtube, for example, a configuration in which an endoscope insertion passage and a treatment tool insertion passage are provided, the endoscope and the treatment tool inserted through the insertion passages, respectively, may co-rotate, a state where the treatment tool is seen with respect to the affected part under the observation image (endoscope image) obtained by the endoscope may be made different, and treatment may be affected.

Additionally, in the configuration in which the endoscope insertion passage and the treatment tool insertion passage are provided inside the overtube, the central axes of the respective insertion passages are provided at positions eccentric from the central axis of the overtube. Therefore, if the treatment tool or the endoscope is operated, there is a problem in that the torque thereof in the rotational direction with respect to the overtube is likely to be generated.

Meanwhile, a technique of providing a ring-shaped protrusion in a direction perpendicular to an insertion direction of the overtube is disclosed in JP2003-61970A and a technique of including an elongated tube with a slit, twisting the elongated tube after insertion into the inside of a body to thereby form a projection resulting from deformation, and fixing the overtube to the body wall is disclosed in JP2009-514651A. However, such techniques are respectively for preventing the overtube from slipping out from the body wall. That is, JP2003-61970A and JP2009-514651A do not consider about the problems caused in the above configurations at all and also do not disclose or imply means for solving the problems.

In this way, in any of the related-art techniques, there are various problems in order to smoothly perform the endoscopic surgery, and it cannot be said that the techniques of interlocking the endoscope and the treatment tool inserted into the body cavity are sufficient.

The invention has been made in view of such a situation and an object thereof is to provide an endoscopic surgical device, an overtube, and an exterior tube with which a surgeon can easily obtain a desired image with simple operation without increasing a burden on the surgeon.

In order to achieve the above object, an endoscopic surgical device related to a first aspect of the invention is an endoscopic surgical device including an endoscope that observes the inside of a body cavity; a treatment tool that inspects or treats an affected part within the body cavity; and an overtube that guides the endoscope and the treatment tool into the body cavity. The overtube includes an overtube body that passes through a body wall and is inserted into the body cavity; an endoscope insertion passage that is provided inside the overtube body and allows the endoscope to be inserted therethrough so as to be movable forward and backward; a treatment tool insertion passage that is provided inside the overtube body and allows the treatment tool to be inserted therethrough so as to be movable forward and backward; and an interlocking member that is configured to be movable forward and backward inside the overtube body, has an endoscope-coupled part to be coupled to the endoscope inserted through the endoscope insertion passage and a treatment tool-coupled part to be coupled to the treatment tool inserted through the treatment tool insertion passage, and has a dead zone where the forward and backward movement of either the endoscope or the treatment tool does not interlock with the movement of the other and a sensing zone where the forward and backward movement of either the endoscope or the treatment tool interlocks with the movement of the other. A contact surface of the overtube body with a body wall includes a rotation-preventing wall surface for preventing rotation in a rotational direction with an axial direction of the overtube body as a center.

In the first aspect of the invention, it is preferable that the rotation-preventing wall surface is provided with a first concavo-convex part including a groove part or a projection part that is formed along an axial direction of the overtube body.

Additionally, in the first aspect of the invention, it is preferable that a plurality of the first concavo-convex parts are provided in the rotational direction of the overtube body.

Additionally, in the first aspect of the invention, it is preferable that the plurality of first concavo-convex parts are periodically provided in the rotational direction of the overtube body.

Additionally, in the first aspect of the invention, it is preferable that the rotation-preventing wall surface is provided with a second concavo-convex part including a groove part or a projection part that is formed along the rotational direction of the overtube body.

Additionally, in the first aspect of the invention, it is preferable that a plurality of the second concavo-convex parts are provided in the axial direction of the overtube body.

Additionally, in the first aspect of the invention, it is preferable that the plurality of second concavo-convex parts are periodically provided in the axial direction of the overtube body.

Additionally, in the first aspect of the invention, it is preferable that the second concavo-convex part includes a first locking surface that restricts the movement of the overtube body to a distal end side in the axial direction, and a second locking surface that restricts the movement of the overtube body to a base end side in the axial direction.

Additionally, in the first aspect of the invention, it is preferable that each of the first locking surface and the second locking surface includes a surfaces including a plane perpendicular to the axial direction of the overtube body.

Additionally, in the first aspect of the invention, it is preferable that the interlocking member includes a slider member that is coupled to the endoscope and moves forward and backward integrally with the endoscope, and a sleeve member that is coupled to the treatment tool and moves forward and backward integrally with the treatment tool, and a range where the sleeve member is movable forward and backward with respect to the slider member is limited.

Additionally, in the first aspect of the invention, it is preferable that the following formula is satisfied when a fixing force for fixing the endoscope-coupled part to the endoscope is defined as F1 and a fixing force for the treatment tool-coupled part to the treatment tool is defined as F2.

$$F1 > F2$$

Additionally, in the first aspect of the invention, it is preferable that the endoscopic surgical device further includes a first valve member that is provided in the endoscope insertion passage and secures airtightness within the body cavity; and a second valve member that is provided in the treatment tool insertion passage and secures airtightness within the body cavity, and the following formulas are satisfied when a fixing force for fixing the endoscope-coupled part to the endoscope is defined as F1, a fixing force for fixing the treatment tool-coupled part to the treatment tool is defined as F2, and a frictional force that the endoscope receives from the first valve member when the endoscope moves forward and backward is defined as F3.

$$F1 > F3$$

$$F2 > F3$$

Additionally, an overtube related to a second aspect of the invention is an overtube including an overtube body that passes through a body wall and is inserted into a body cavity; an endoscope insertion passage that is provided inside the overtube body and allows an endoscope for observing the inside of the body cavity to be inserted therethrough so as to be movable forward and backward; a treatment tool insertion passage that is provided inside the overtube body and allows a treatment tool for inspecting or treating an affected part within the body cavity to be inserted therethrough so as to be movable forward and backward; and an interlocking member that is configured to be movable forward and backward inside the overtube body, has an endoscope-coupled part to be coupled to the endoscope inserted through the endoscope insertion passage and a treatment tool-coupled part to be coupled to the treatment tool inserted through the treatment tool insertion passage, and has a dead zone where the forward and backward movement of either the endoscope or the treatment tool does not interlock with the movement of the other and a sensing zone where the forward and backward movement of either the endoscope or the treatment tool interlocks with the movement of the other. A contact surface of the overtube body with a body wall includes a rotation-preventing wall surface for preventing rotation in a rotational direction with an axial direction of the overtube body as a center.

In the second aspect of the invention, the rotation-preventing wall surface is provided with a groove part or a projection part that is formed along an axial direction of the overtube body.

Additionally, in the second aspect of the invention, it is preferable that a plurality of the first concavo-convex parts are provided in the rotational direction of the overtube body.

Additionally, in the second aspect of the invention, it is preferable that the plurality of first concavo-convex parts are periodically provided in the rotational direction of the overtube body.

Additionally, in the second aspect of the invention, it is preferable that the rotation-preventing wall surface is provided with a second concavo-convex part having a groove part or a projection part that is formed along the rotational direction of the overtube body.

Additionally, in the second aspect of the invention, it is preferable that a plurality of the second concavo-convex parts are provided in the axial direction of the overtube body.

Additionally, in the second aspect of the invention, it is preferable that the plurality of second concavo-convex parts are periodically provided in the axial direction of the overtube body.

Additionally, in the second aspect of the invention, it is preferable that the second concavo-convex part includes a first locking surface that restricts the movement of the overtube body to a distal end side in the axial direction, and a second locking surface that restricts the movement of the overtube body to a base end side in the axial direction.

Additionally, in the second aspect of the invention, it is preferable that each of the first locking surface and the second locking surface includes a surface including a plane perpendicular to the axial direction of the overtube body.

Additionally, an endoscopic surgical device related to a third aspect of the invention is an endoscopic surgical device including an endoscope that observes the inside of a body cavity; a treatment tool that inspects or treats an affected part within the body cavity; an overtube that guides the endoscope and the treatment tool into the body cavity; and an exterior tube that fixes the overtube to an abdominal wall. The overtube includes an overtube body that passes through a body wall and is inserted into the body cavity; an endoscope insertion passage that is provided inside the overtube body and allows the endoscope to be inserted therethrough so as to be movable forward and backward; a treatment tool insertion passage that is provided inside the overtube body and allows the treatment tool to be inserted therethrough so as to be movable forward and backward; and an interlocking member that is configured to be movable forward and backward inside the overtube body, has an endoscope-coupled part to be coupled to the endoscope inserted through the endoscope insertion passage and a treatment tool-coupled part to be coupled to the treatment tool inserted through the treatment tool insertion passage, and has a dead zone where the forward and backward movement of either the endoscope or the treatment tool does not interlock with the movement of the other and a sensing zone where the forward and backward movement of either the endoscope or the treatment tool interlocks with the movement of the other. The exterior tube includes an insertion part that covers the portion of the overtube body that passes through the body wall; a base end part that is provided on a base end side of the insertion part and has a larger external diameter than that of the insertion part; and an airtight valve that is provided at the base end part and maintains the airtightness with the overtube body. A plurality of transverse grooves along a circumferential direction are formed in an axial direction in an outer peripheral surface of the insertion part, the transverse grooves have a distal end-side wall surface and a base-end-side wall surface, and an inclination angle of the distal end-side wall surface with respect to a radial direction of the insertion part is made smaller than an inclination angle of the base-end-side wall surface with respect to the radial direction of the insertion part.

Additionally, in the third aspect of the invention, it is preferable that the distal end-side wall surface is configured to incline in the same direction as the radial direction of the insertion part or incline to the base-end-side wall surface side.

Additionally, in the third aspect of the invention, it is preferable that a plurality of axial longitudinal grooves are formed in the circumferential direction at an outer peripheral part of the insertion part.

Additionally, an exterior tube related to a fourth aspect of the invention is an exterior tube that fixes an overtube to an abdominal wall. The overtube includes an overtube body that passes through a body wall and is inserted into the body cavity; an endoscope insertion passage that is provided inside the overtube body and allows an endoscope for observing the inside of the body cavity to be inserted therethrough so as to be movable forward and backward; a treatment tool insertion passage that is provided inside the overtube body and allows a treatment tool for inspecting or treating an affected part within the body cavity to be inserted therethrough so as to be movable forward and backward; and an interlocking member that is configured to be movable forward and backward inside the overtube body, has an endoscope-coupled part to be coupled to the endoscope inserted through the endoscope insertion passage and a treatment tool-coupled part to be coupled to the treatment tool inserted through the treatment tool insertion passage, and has a dead zone where the forward and backward movement of either the endoscope or the treatment tool does not interlock with the movement of the other and a sensing zone where the forward and backward movement of either the endoscope or the treatment tool interlocks with the movement of the other. The exterior tube includes an insertion part that covers the portion of the overtube body that passes through the body wall; a base end part that is provided on a base end side of the insertion part and has a larger external diameter than that of the insertion part; and an airtight valve that is provided at the base end part and maintains the airtightness with the overtube body. A plurality of transverse grooves along a circumferential direction are formed in an axial direction in an outer peripheral surface of the insertion part, the transverse grooves have a distal end-side wall surface and a base-end-side wall surface, and an inclination angle of the distal end-side wall surface with respect to a radial direction of the insertion part is made smaller than an inclination angle of the base-end-side wall surface with respect to the radial direction of the insertion part.

Additionally, in the fourth aspect of the invention, it is preferable that the distal end-side wall surface is configured to incline in the same direction as the radial direction of the insertion part or incline to the base-end-side wall surface side.

Additionally, in the fourth aspect of the invention, it is preferable that a plurality of axial longitudinal grooves are formed in the circumferential direction at an outer peripheral part of the insertion part.

According to the invention, the endoscope moves forward and backward with play with respect to the forward and backward movement of the treatment tool. Thus, when the treatment tool has been minutely displaced in the axial direction (when a forward and backward movement of a small amplitude has been performed), the size of an object to be observed can be prevented from fluctuating, a sense of perspective can be suitably maintained, and a stable observation image can be provided. Additionally, when the treatment tool has been largely displaced in the axial direction (when a forward and backward movement of a large amplitude has been performed), the range of an observation image obtained by the endoscope is changed in an interlocking manner with this large displacement. Thus, the size of an object to be observed changes according to the operation of the treatment tool, it is possible to simply obtain an image desired by a surgeon, and operability improves. Additionally, by virtue of the rotation-preventing wall surface that constitutes the contact surface of the overtube (overtube body) contacting the body wall, the rotation in the rotational direction with the axial direction of the overtube as a center can be prevented, and the overtube can be reliably fixed to the body wall. Accordingly, the positional relationship between an affected part and the treatment tool can be maintained in a suitable state under the observation image obtained by the endoscope and thus treatment performance can be improved, an image desired by a surgeon can be simply obtained, and endoscopic surgery can be smoothly performed.

BRIEF DESCRIPTION OF THE DRAWINGS

FIGS. 35A to 35C are views illustrating a situation in which the overtube is inserted into a body wall.

FIGS. 36A and 36B are views illustrating a situation in which a treatment tool insertion part is pushed into an affected part side within a body cavity from a hand side.

FIGS. 38A and 38B are views illustrating a situation in which the treatment tool insertion part is pulled to the hand side from the affected part side within the body cavity.

DESCRIPTION OF THE PREFERRED EMBODIMENTS

A preferred embodiment of the invention will be described below in detail according to the accompanying drawings. In addition, any drawing may illustrate main parts in an exaggerated manner for description, and may have dimensions different from actual dimensions. Additionally, in the following, characteristic parts of the invention will be described in detail after the basic configuration of an endoscope surgical device (endoscopic surgical device) is first described.

<Configuration of Endoscopic Surgical Device>

Figure 1:
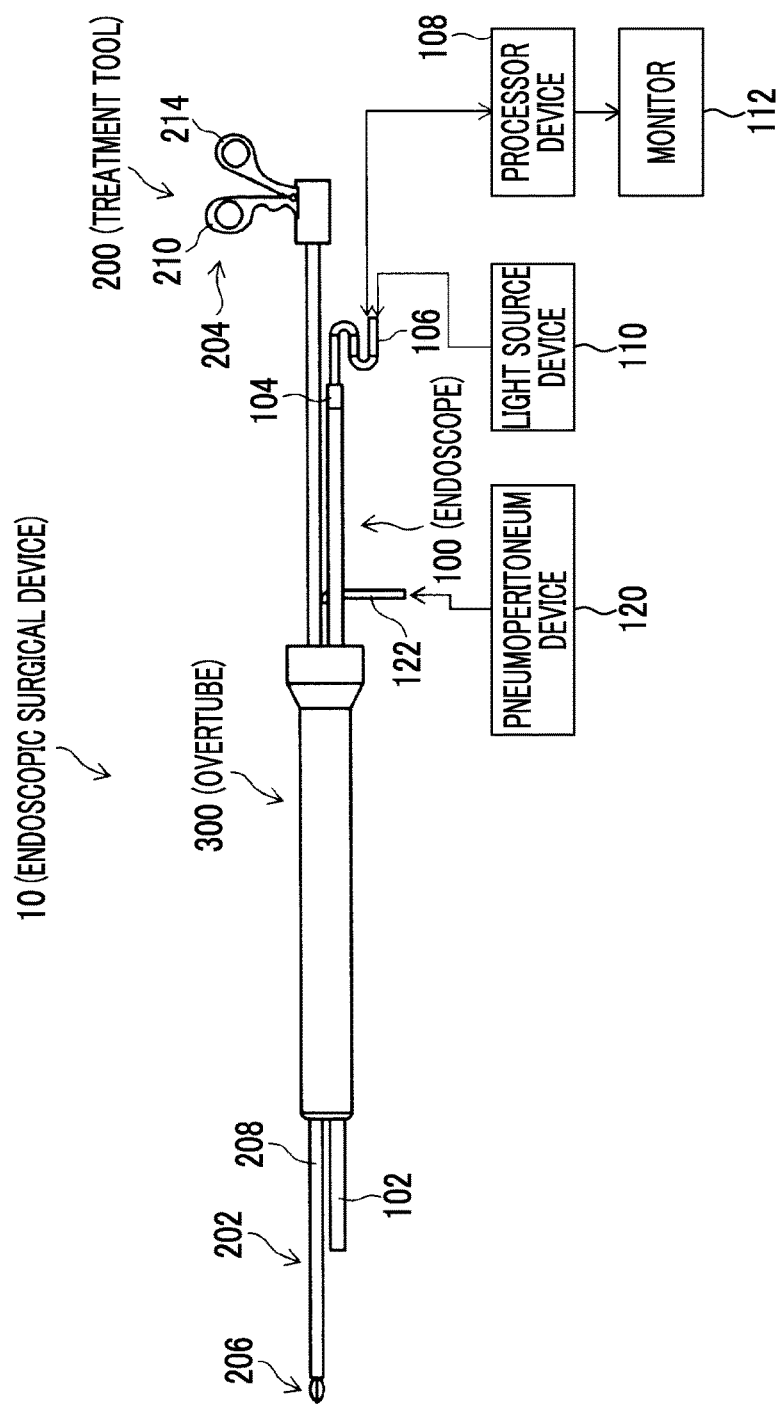
FIG. 1 is a schematic configuration diagram illustrating the basic configuration of an endoscopic surgical device.

FIG. 1 is a schematic configuration diagram illustrating the basic configuration of the endoscopic surgical device. As illustrated in FIG. 1, an endoscopic surgical device 10 includes an endoscope 100 that observes the inside of a patient's body cavity, a treatment tool 200 for inspecting or treating an affected part within the patient's body cavity, and an overtube 300 (guide member) that guides the endoscope 100 and the treatment tool 200 into the body cavity.

<Configuration of Endoscope>

The endoscope 100 includes an elongated insertion part (hereinafter referred to as "endoscope insertion part") 102 that is, for example, a hard endoscope, such as a laparoscope, and that is inserted into a body cavity, and an operating part 104 that is provided continuously with a base end side of the endoscope insertion part 102. A universal cable 106 is connected to the operating part 104, and each of a processor device 108 and a light source device 110 is detachably connected to a distal end part of the universal cable 106 via a connector (not illustrated). Additionally, the processor device 108 is connected to a monitor 112 via a cable.

Figure 2:
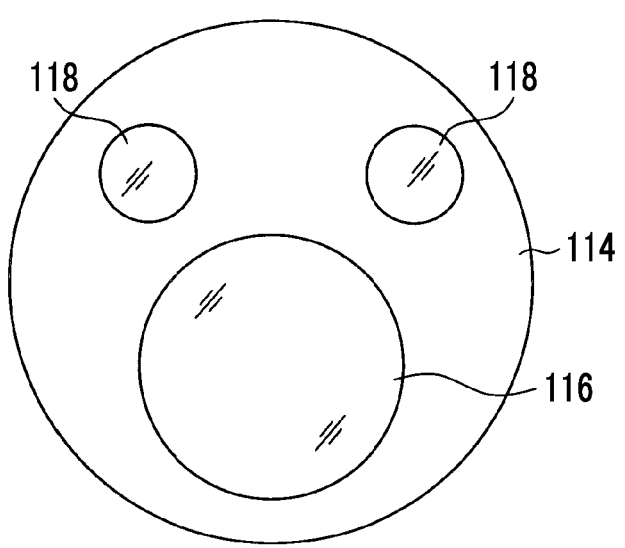
FIG. 2 is a plan view illustrating a distal end surface of an endoscope insertion part.

As illustrated in FIG. 2, a distal end surface 114 of the endoscope insertion part 102 is provided with an observation window 116 and illumination windows 118 and 118.

An objective lens of an observation optical system, and an image pick-up element, such as a charge-coupled device (CCD) or a complementary metal-oxide semiconductor (CMOS), which is arranged at an image pick-up position of the objective lens, are disposed behind the observation window 116. A signal cable (not illustrated) is connected to a substrate that supports the image pick-up element. The signal cable is inserted through the endoscope insertion part 102, the operating part 104, and the universal cable 106, and the like of FIG. 1, is provided to extend up to the connector (not illustrated), and is connected to the processor device 108. An observation image picked up by the observation window 116 is formed on a light-receiving surface of the image pick-up element, and is converted into electrical signals (image pick-up signals), and the electrical signals are output to the processor device 108 via the signal cable and are converted into video signals. Then, the video signals are output to the monitor 112 connected to the processor device 108, and the observation image (endoscope image) is displayed on a screen of the monitor 112.

An exit end of a light guide (not illustrated) is disposed behind the illumination windows 118 and 118 of FIG. 2. The light guide is inserted through the endoscope insertion part 102, the operating part 104, and the universal cable 106 of FIG. 1 and has an incident end disposed within the connector (not illustrated). Therefore, by coupling the connector to the light source device 110, the illumination light radiated from the light source device 110 is transmitted to the illumination windows 118 and 118 via the light guide, and is radiated forward from the illumination windows 118 and 118. In addition, in FIG. 2, the two illumination windows 118 and 118 are disposed on the distal end surface 114 of the endoscope insertion part 102. However, the number of the illumination windows 118 is not limited, and the number thereof may be one or three or more.

<Configuration of Treatment Tool>

As illustrated in FIG. 1, the treatment tool 200 consists of, for example, forceps, and includes an elongated insertion part (hereinafter referred to as a "treatment tool insertion part") 202 that is inserted into a body cavity, an operating part 204 that is provided on the base end side of the treatment tool insertion part 202 and is gripped by a surgeon, and a treatment part 206 that is provided on a distal end side of the treatment tool insertion part 202 and is operable by the operation of the operating part 204.

The treatment tool insertion part 202 is provided with a tubular sheath 208, and an operating shaft (not illustrated) that is inserted into the sheath 208 so as to be movable in the direction of an axial center. Moreover, the operating part 204 is provided with a fixed handle 210, and a movable handle 214 that is rotatably coupled to the fixed handle 210 via a turning pin. A base end part of the operating shaft is coupled to the movable handle 214.

The treatment part 206 is provided with a pair of gripping members capable of being openable and closable. The gripping members are coupled to a distal end part of the operating shaft via a driving mechanism (not illustrated). With the rotational operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, and an ultrasonic aspirator.

<Configuration of Overtube>

Figure 3:
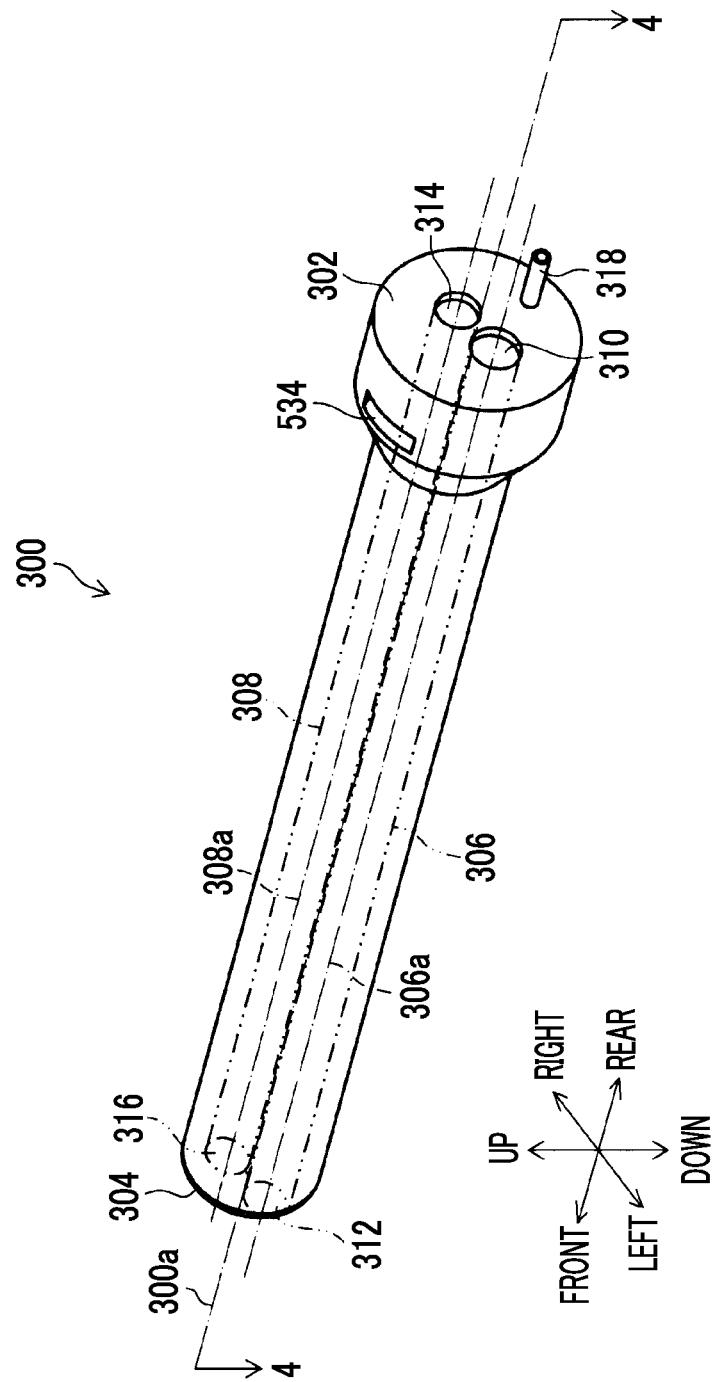
FIG. 3 is an external appearance perspective view illustrating an overtube from the rear upper left.

FIG. 3 is an external appearance perspective view illustrating the overtube 300 from the rear upper left.

As illustrated in this drawing, the overtube 300 has an endoscope insertion passage 306 through which the endoscope insertion part 102 of the endoscope 100 is inserted so as to be movable forward and backward, and a treatment tool insertion passage 308 through which the treatment tool insertion part 202 of the treatment tool 200 is inserted so as to be movable forward and backward.

The endoscope insertion passage 306 has a diameter such that at least the endoscope insertion part 102 is capable of being inserted therethrough, using an endoscope insertion axis 306a, which is parallel to a reference axis 300a (longitudinal axis) indicating a central axis of the entire overtube 300, as a central axis, and indicates a space portion within the overtube 300 that penetrates from a base end surface 302 of the overtube 300 to a distal end surface 304 thereof. The endoscope insertion axis 306a is equivalent to the position of the axis (central axis) of the endoscope insertion part 102 that is inserted through the endoscope insertion passage 306.

The base end surface 302 is provided with an endoscope insertion opening 310 for allowing the endoscope insertion part 102 to be inserted into the endoscope insertion passage 306 therethrough, and the distal end surface 304 is provided with an endoscope delivery opening 312 for allowing the endoscope insertion part 102 inserted into the endoscope insertion passage 306 to be delivered to the outside therethrough.

The treatment tool insertion passage 308 has a diameter such that at least the treatment tool insertion part 202 is capable of being inserted therethrough, using a treatment tool insertion axis 308a parallel to the reference axis 300a as a central axis, and indicates a space portion within the overtube 300 that penetrates from the base end surface 302 of the overtube 300 to the distal end surface 304. The treatment tool insertion axis 308a is equivalent to the position of the axis (central axis) of the treatment tool insertion part 202 that is inserted through the treatment tool insertion passage 308.

The base end surface 302 is provided with a treatment tool insertion opening 314 for allowing the treatment tool insertion part 202 to be inserted into the treatment tool insertion passage 308 therethrough, and the distal end surface 304 is provided with a treatment tool delivery opening 316 for allowing the treatment tool insertion part 202 inserted into the treatment tool insertion passage 308 to be delivered to the outside therethrough.

Additionally, the overtube 300 has an air supply connector 318 (fluid-supplying connector) on the base end surface 302. The air supply connector 318 is provided at the end part of an air supply pipe line that communicates with the endoscope insertion passage 306 and the treatment tool insertion passage 308 inside the overtube 300.

One end part of an air supply tube 122 (tube member) illustrated in FIG. 1 is connected to the air supply connector 318, and the other end part of the air supply tube 122 is connected to a pneumoperitoneum device 120. Therefore, if pneumoperitoneum gas (gas for pneumoperitoneum), such as carbon dioxide gas, is supplied from the pneumoperitoneum device 120 to the air supply tube 122, the pneumoperitoneum gas is sent from the air supply connector 318 to the inside of the overtube 300, and is delivered from the endoscope delivery opening 312 and the treatment tool delivery opening 316 of the distal end surface 304 through the inside of the overtube 300 to the outside of the overtube 300.

In addition, regarding the position and orientation of a space where the overtube 300 has been arranged, terms called front, rear, left, right, up, and down are used with the orientation from the base end surface 302 in a direction along the reference axis 300a to the distal end surface 304 defined as the front and with the orientation from the reference axis 300a to the endoscope insertion axis 306a defined as the left.

(Internal Structure of Overtube)

Figure 4:
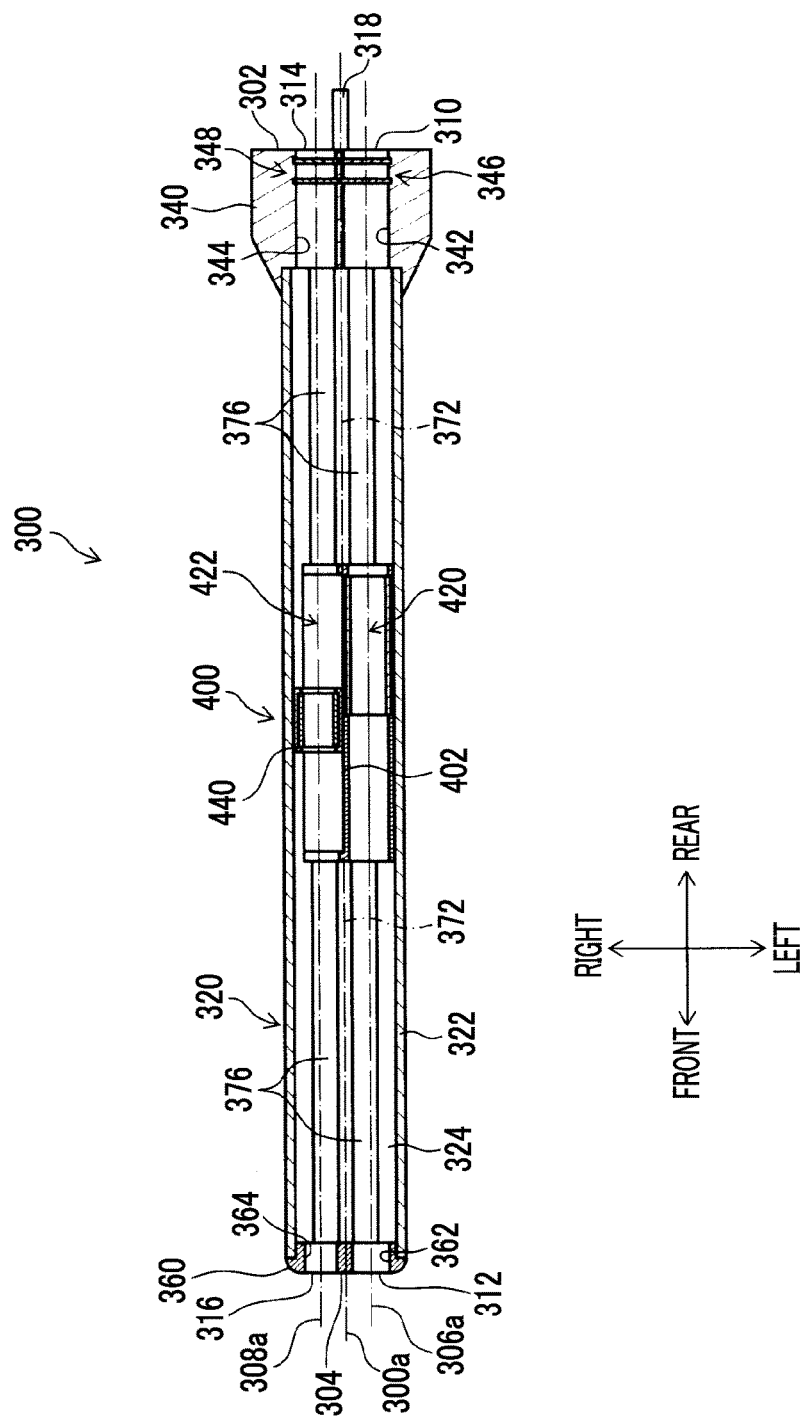
FIG. 4 is a sectional view, as seen from arrow 4-4 of FIG. 3, illustrating the internal structure of the overtube.

The specific configuration of the overtube 300 will be described. FIG. 4 is a sectional view (a sectional view as seen from arrow 4-4 of FIG. 3) illustrating the internal structure of the overtube 300, and illustrates a section cut in a plane that includes the reference axis 300a and orthogonal to an upward-downward direction. In the present specification, when a drawing is simply called a sectional view, the drawing illustrates a sectional view cut by the same plane as FIG. 4.

As illustrated in this drawing, the overtube 300 has an overtube body 320 that occupies substantially the entire area in a forward-rearward direction, a base end cap 340 that is arranged at a rear part of the overtube 300, a distal end cap 360 that is arranged at a distal end part, and a slider 400 (interlocking member) that is arranged inside the overtube 300. In addition, the base end cap 340 and the distal end cap 360 are some of the constituent elements of the overtube body of the invention, and may be formed separately from or formed integrally with the overtube body 320.

(Description of Overtube Body)

The overtube body 320 is formed in an elongated cylindrical shape having the reference axis 300a as a central axis using hard resin, metal, or the like, and has an outer wall 322 that surrounds an outer periphery, and a lumen 324 that penetrates from a base end of the overtube body 320 to a distal end thereof.

The lumen 324 has the endoscope insertion axis 306a and the treatment tool insertion axis 308a inserted therethrough, and is provided with a space that serves as the endoscope insertion passage 306 and the treatment tool insertion passage 308.

Additionally, the lumen 324 serves as the air supply pipe line through which the pneumoperitoneum gas sent in from the air supply connector 318 passes.

The base end cap 340 is attached to the base end of the overtube body 320, and is formed in a columnar shape made to have a larger diameter than the external diameter of the overtube body 320, using hard resin, metal, or the like. The base end cap 340 has a flat rear end surface serving as the base end surface 302 of the overtube 300 on the rear side thereof, and has through-holes 342 and 344 that penetrate from the base end surface 302 to the lumen 324 of the overtube body 320.

The through-hole 342 has a central axis arranged coaxially with the endoscope insertion axis 306a, and forms a portion of the endoscope insertion passage 306. An opening of the through-hole 342 in the base end surface 302 is equivalent to the above-described endoscope insertion opening 310.

The through-hole 344 has a central axis arranged coaxially with the treatment tool insertion axis 308a, and forms a portion of the treatment tool insertion passage 308. An opening of the through-hole 344 in the base end surface 302 is equivalent to the above-described treatment tool insertion opening 314.

Valve members 346 and 348 (a first valve member 346, a second valve member 348) are respectively arranged in the through-hole 342 and the through-hole 344. Although the detailed description of the valve members 346 and 348 is omitted, the valve members have, for example, slits that open only when being inserted through the endoscope insertion part 102 and the treatment tool insertion part 202 and that come into close contact with outer peripheral surfaces (side surfaces) of the endoscope insertion part 102 and the treatment tool insertion part 202 without a substantial gap. This secures the airtightness of spaces closer to the distal end side than the valve members 346 and 348, and reduces the leakage or the like of the pneumoperitoneum gas injected into the body cavity to the outside of the body.

In addition, the valve members 346 and 348 are not limited to those with the specific configuration, and valve members with widely-known arbitrary configurations can be used. Although FIG. 4 illustrates a configuration in which the two valve members are respectively arranged in the through-hole 342 and the through-hole 344, a configuration in which one valve member or three or more valve members are arranged may be adopted.

(Description of Air Supply Connector)

Figure 5:
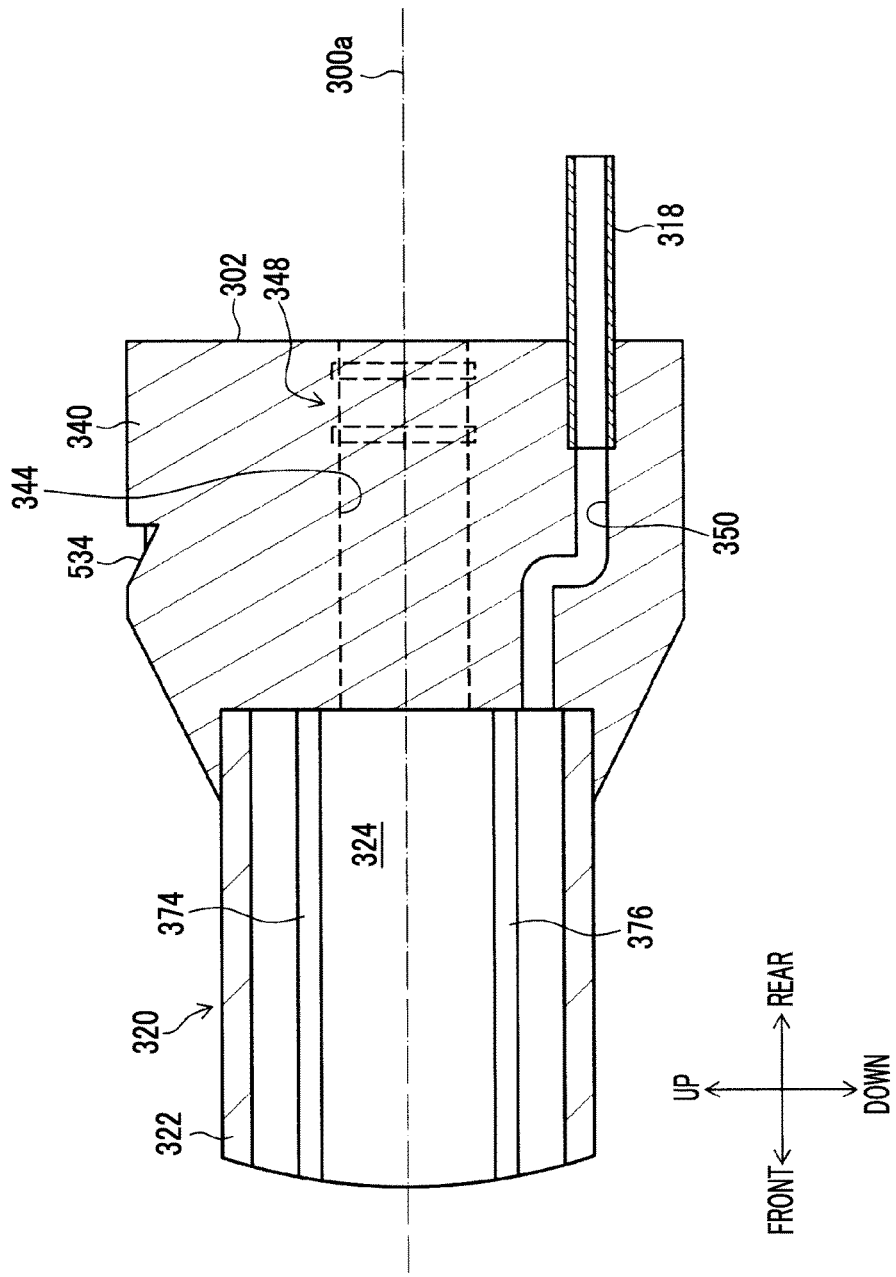
FIG. 5 is a sectional view of the periphery of a base end cap cut in a plane orthogonal to a paper surface of FIG. 4.

Additionally, FIG. 5 is a sectional view of the periphery of the base end cap 340 when the overtube 300 is cut in a plane that includes the reference axis 300a and is orthogonal to the paper surface of FIG. 4. As illustrated in this drawing, the base end cap 340 has a through-hole 350 that penetrates from the base end surface 302 to the lumen 324 of the overtube body 320.

The through-hole 350 is a portion of the air supply pipe line that allows the pneumoperitoneum gas to flow therethrough, and has a rear end part formed at a position below the reference axis 300a. The rear end part is provided with the above-described air supply connector 318 to which the air supply tube 122 (refer to FIG. 1) from the pneumoperitoneum device 120 is connected.

The air supply connector 318 is formed in an elongated cylindrical shape, and has a part buried and fixed inside the through-hole 350. Accordingly, at a position below the reference axis 300a in the base end surface 302, the axis (central axis) of the air supply connector 318 is arranged so as to be substantially orthogonal to the base end surface 302 (arranged parallel to the reference axis 300a), and the air supply connector 318 is provided to protrude rearward from the base end surface 302.

The air supply tube 122 is connected to the air supply connector 318 by fitting the air supply tube 122 to the outer periphery of the air supply connector 318. Then, if the pneumoperitoneum gas is delivered from the pneumoperitoneum device 120 to the air supply tube 122, the pneumoperitoneum gas is sent into the lumen 324 of the overtube body 320 from the air supply connector 318.

(Merits Based on Arrangement of Air Supply Connector on Base End Surface)

Here, in an overtube that guides one medical instrument into a body cavity, it is general that the air supply connector is provided not on a base end surface of the overtube but on a side surface thereof.

This is because the air supply connector may interfere with an inner needle supposing that the air supply connector is provided on the base end surface, and because the overtube can be rotated around the axis so as to prevent the interference of the air supply connector and the air supply tube with a body wall without influencing the position of the medical instrument inserted through the overtube even if the air supply connector is provided on the side surface.

On the other hand, in the overtube 300 of the present embodiment, if the overtube 300 is rotated around the axis, the position of the endoscope insertion part 102 and the treatment tool insertion part 202 changes. Therefore, a case where it is difficult to avoid any interference of the air supply connector 318 and the air supply tube 122 with the body wall while maintaining the positions of the endoscope insertion part 102 and the treatment tool insertion part 202 within the body cavity at positions desired by a surgeon may occur.

Thus, in the overtube 300 of the present embodiment, the interference of the air supply connector 318 and the air supply tube 122 with the body wall is prevented by arranging the air supply connector 318 on the base end surface 302 of the overtube 300, and the interference of the air supply tube with the inner needle is avoided by devising the configuration of the inner needle as will be described below.

In addition, the air supply pipe line within the air supply connector 318 and the overtube 300 may be provided in order to supply fluids other than the pneumoperitoneum gas into a body cavity.

The distal end cap 360 illustrated in FIG. 4 is attached to the distal end of the overtube body 320, and is formed of hard resin, metal, or the like. The distal end cap 360 has a front surface serving as the distal end surface 304 of the overtube 300 on a front side thereof, and has through-holes 362 and 364 that penetrate from the lumen 324 of the overtube body 320 to the distal end surface 304.

The through-hole 362 has a central axis arranged coaxially with the endoscope insertion axis 306a, and forms a portion of the endoscope insertion passage 306. An opening of the through-hole 362 in the distal end surface 304 is equivalent to the above-described endoscope delivery opening 312.

The through-hole 364 has a central axis arranged coaxially with the treatment tool insertion axis 308a, and forms a portion of the treatment tool insertion passage 308. An opening of the through-hole 364 in the distal end surface 304 is equivalent to the above-described treatment tool delivery opening 316.

Additionally, as described above, the pneumoperitoneum gas sent into the lumen 324 of the overtube body 320 via the air supply tube 122, the air supply connector 318 of the base end cap 340, and the through-hole 350 from the pneumoperitoneum device 120 is delivered to the outside (the inside of a body cavity) via the through-hole 362 and the through-hole 364.

Although the overtube body 320, the base end cap 340, and the distal end cap 360 above form the outer wall of the overtube 300, the outer wall of the overtube 300 may not necessarily be constituted of these separated members.

The air supply pipe line of the overtube body 320 through which the pneumoperitoneum gas passes may be a lumen that is provided separately from the lumen 324.

(Description of Slider)

Next, the slider 400 will be described.

The slider 400 illustrated in FIG. 4 is housed within the lumen 324 of the overtube body 320, and is supported so as to be movable forward and backward in the direction of the reference axis 300a.

The slider 400 is an interlocking member that is coupled to the endoscope insertion part 102 inserted through the endoscope insertion passage 306 and the treatment tool insertion part 202 inserted through the treatment tool insertion passage 308 and that has a dead zone where the forward and backward movement of either the endoscope insertion part or the treatment tool insertion part in the forward-rearward direction (axial direction) does not interlock with the movement of the other and a sensing zone where the forward and backward movement of either the endoscope insertion part or the treatment tool insertion part interlocks with the movement of the other.

That is, the endoscope insertion part 102 is adapted to interlock with the forward and backward movement of the treatment tool insertion part 202 in the axial direction with play.

Accordingly, when a surgeon has moved the treatment tool insertion part 202 forward and backward in the axial direction and when the axial displacement of the treatment tool insertion part 202 is large (when a forward and backward movement of a large amplitude has been performed), the endoscope insertion part 102 also moves in an interlocking manner forward, backward, upward, downward, rightward, and leftward. Thus, the visual field, orientation, and the like of the endoscope 100 can be changed as intended by a surgeon. Additionally, the visual field is always given to pick up an image of a treatment tool distal end, and consequently, an image that is optimal for treatment is automatically provided. When it is desired to check places other than the treatment part, the checking can be performed by moving forceps, and a surgeon can perform operations as desired. Therefore, an assistant (scopist) who operates the endoscope 100 apart from the surgeon can be made unnecessary, and a troublesome condition in which the surgeon should instruct an assistant about the visual field, orientation, and the like of the endoscope serially can be eliminated.

Additionally, when the axial displacement of the treatment tool insertion part 202 is small (when a forward and backward movement of a small amplitude has been performed), the endoscope insertion part 102 does not interlock. Therefore, the size of an object to be observed within an observation image can be prevented from fluctuating unnecessarily, a sense of perspective can be suitably maintained, and a stable observation image can be provided.

(Internal Structure of Slider)

The internal structure of the slider 400 will be described.

Figure 6:
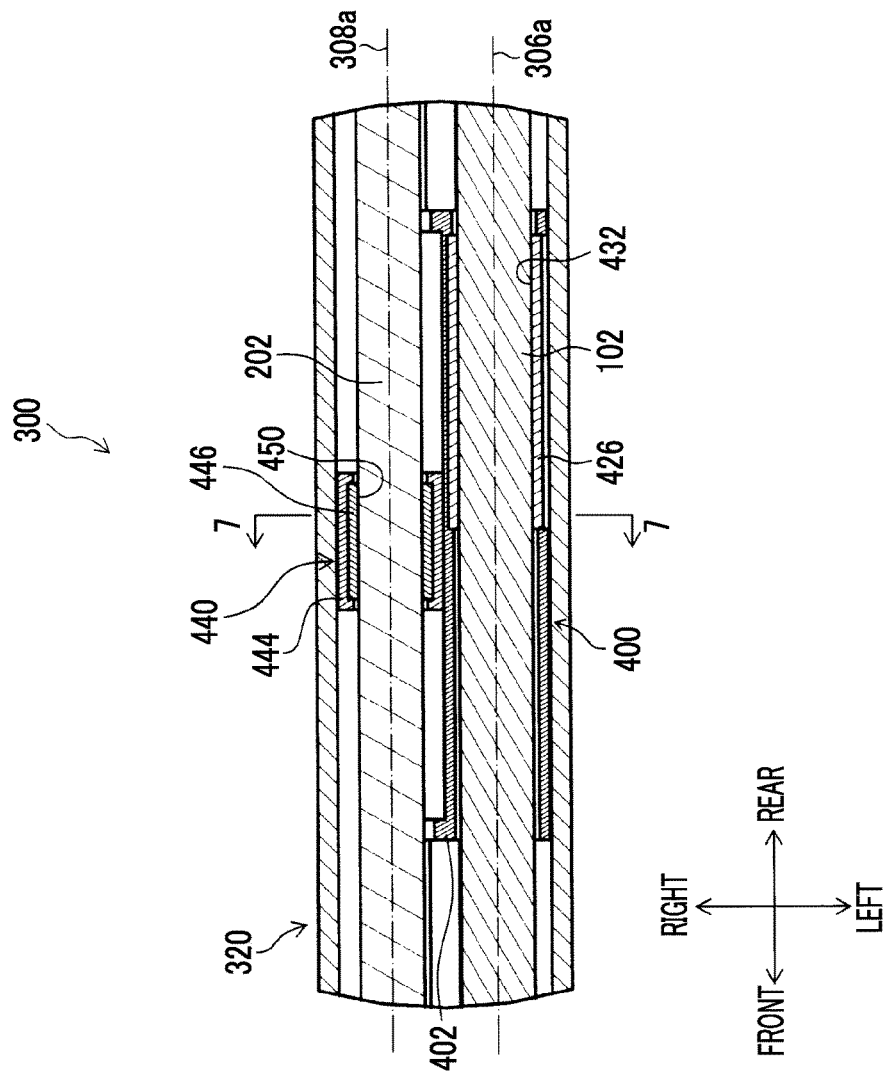
FIG. 6 is an enlarged sectional view illustrating a portion of FIG. 4 in an enlarged manner.

FIG. 6 is an enlarged sectional view illustrating a portion, in which the slider 400 is arranged in FIG. 4, in an enlarged manner, and illustrates a state where the endoscope insertion part 102 and the treatment tool insertion part 202 have been inserted through the endoscope insertion passage 306 and the treatment tool insertion passage 308, respectively.

Figure 7:
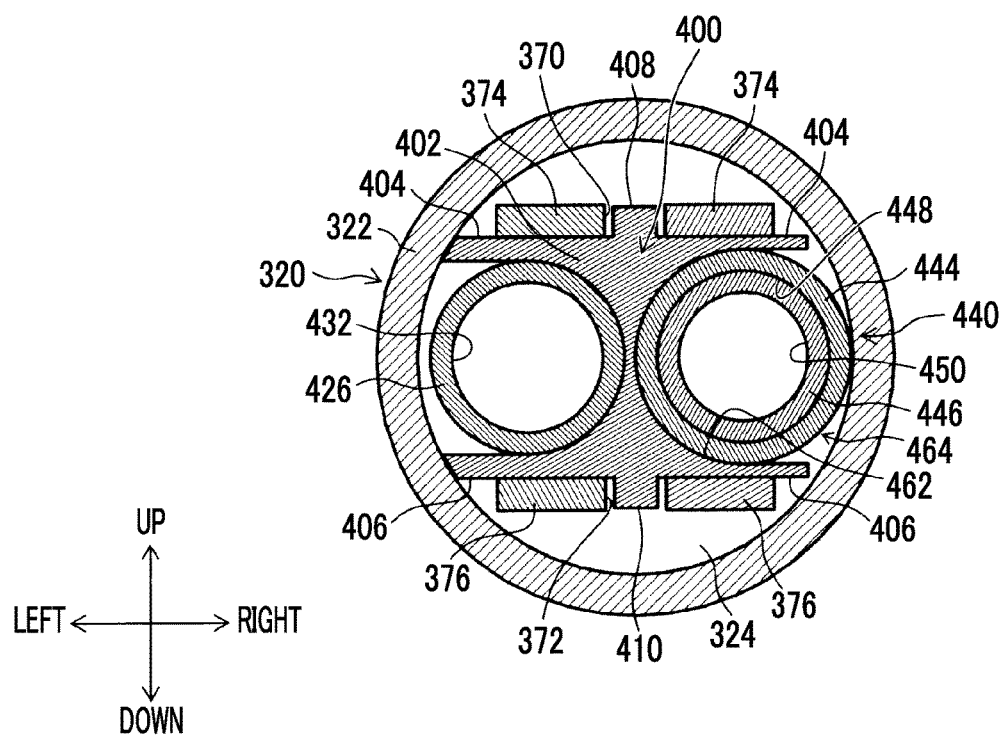
FIG. 7 is a view as seen from arrow 7-7 in FIG. 6.

FIG. 7 is a view as seen from arrow 7-7 in FIG. 6.

Figure 8:
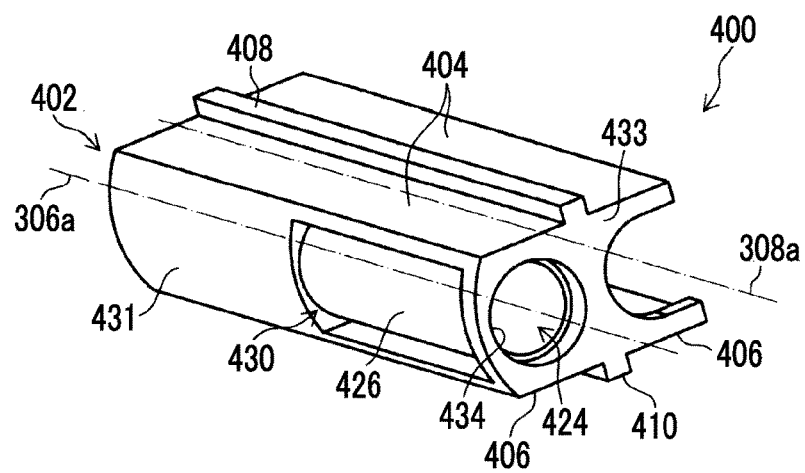
FIG. 8 is a perspective view illustrating a slider from the rear upper left.
Figure 9:
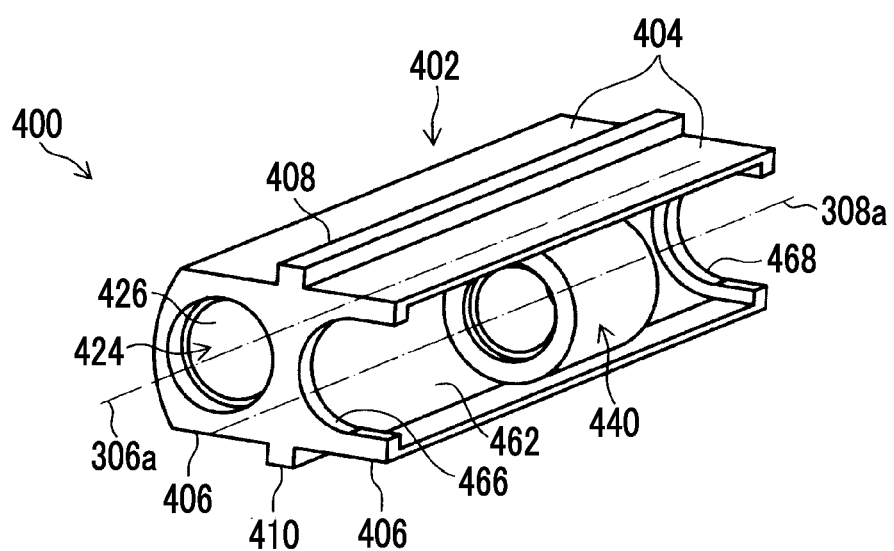
FIG. 9 is a perspective view illustrating the slider from the rear upper right.
Figure 10:
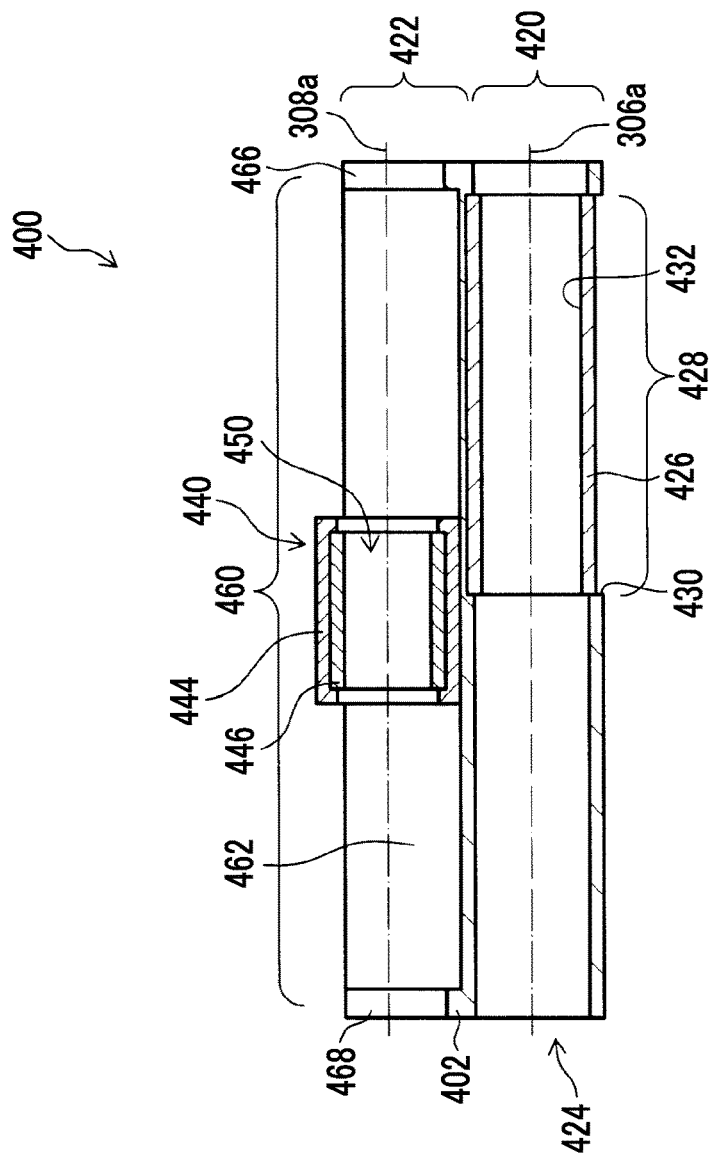
FIG. 10 is a sectional view of the slider.

Additionally, FIGS. 8 and 9 are respectively perspective views illustrating the slider 400 from the rear upper left and from the rear upper right and FIG. 10 is a sectional view of only the slider 400.

As illustrated in FIGS. 6 to 10, the slider 400 has a slider body 402 (slider member) that holds components of the slider 400. The slider body 402, as illustrated in FIGS. 7 to 9, has a flat upper surface 404 and a flat lower surface 406, and has protruding strips 408 and 410, respectively, on the upper surface 404 and the lower surface 406.

The protruding strips 408 and 410 respectively protrude in the upward-downward direction at substantially central parts of the upper surface 404 and the lower surface 406 in a leftward-rightward direction, extend in the direction (forward-rearward direction) of the reference axis 300a within the lumen 324 of the overtube body 320, and are fitted into guide grooves 370 and 372 provided in an upper part and a lower part within the lumen 324 of the overtube body 320 as illustrated in FIG. 7.

The guide grooves 370 and 372 are respectively formed by gaps between a pair of left and right guide plates 374 and 374 and a pair of left and right the guide plates 376 and 376 that are arranged at the upper part and the lower part within the lumen 324.

The guide plates 376 and 376 arranged at the lower part within the lumen 324 are illustrated in FIG. 4. As illustrated in this drawing, the guide plates 374 and 374 and the guide plates 376 and 376 are respectively formed in the shape of a long plate, and are installed along the direction of the reference axis 300a by being laid between the base end cap 340 and the distal end cap 360.

Accordingly, the guide grooves 370 and 372 are respectively arranged along the direction of the reference axis 300a from the base end cap 340 to the distal end cap 360 within the lumen 324.

As illustrated in FIG. 7, in a state where the slider 400 is housed and arranged within the lumen 324, the protruding strips 408 and 410 are respectively fitted into the guide grooves 370 and 372, and the upper surface 404 and the lower surface 406 respectively contact or approach the guide plates 374 and 374 and the guide plates 376 and 376. Accordingly, the slider 400 (slider body 402) is supported so as to be movable forward and backward in the forward-rearward direction within the lumen 324, and is supported in a state where the movement of the slider in the upward-downward direction and in the leftward-rightward direction and the rotation of the slider in all directions are restricted (a state where the rotation of the slider around at least the reference axis 300a is impossible).

In addition, the guide grooves 370 and 372 may not be formed by the guide plates 374 and 374 and the guide plates 376 and 376 arranged within the lumen 324 of the overtube body 320, and may be formed in the outer wall 322 of the overtube body 320 or may be formed by other configurations.

Additionally, a range (movable range) in which the slider 400 (slider body 402) moves forward and backward in the forward-rearward direction with respect to the overtube body 320 is a range having a position where the slider 400 abuts against the base end cap 340 as a rear end (a position closest to the base end) and having a position where the slider abuts against the distal end cap 360 as a front end (a position closest to the distal end). However, the rear end and the front end of the movable range of the slider 400 may not be restricted by the base end cap 340 and the distal end cap 360.

Additionally, the slider 400, as illustrated in FIG. 10, has a endoscope-coupled part 420 that is coupled (engaged) with the endoscope insertion part 102, and a treatment tool-coupled part 422 that is coupled (engaged) with the treatment tool insertion part 202.

(Description of Endoscope-Coupled Part)

The endoscope-coupled part 420 is provided on the left side of the slider body 402, and includes a through-hole 424 in which a space serving as the endoscope insertion passage 306 is secured within the lumen 324 of the overtube body 320 and through which, as illustrated in FIG. 6, the endoscope insertion part 102 is inserted, and a pressure-contact member 426 that is brought into pressure contact with the outer peripheral surface (side surface) of the endoscope insertion part 102 inserted through the endoscope insertion passage 306.

The through-hole 424 is formed to penetrate from a rear end of the slider body 402 to a front end thereof, and has a larger diameter than the external diameter of at least the endoscope insertion part 102. A central axis of the through-hole 424 is arranged coaxially with the endoscope insertion axis 306a within the lumen 324.

A pressure-contact member attachment part 428 for attaching the pressure-contact member 426 is provided on the rear end side of the through-hole 424.

The pressure-contact member attachment part 428 has an internal diameter that is made larger than other position ranges of the through-hole 424, and has formed therein an opening 430 (refer to FIG. 8) that penetrates up to an outer surface (left side surface 431) of the slider body 402 in a partial range thereof (a left side surface of the slider 400) in the circumferential direction. The pressure-contact member 426 is fitted into the through-hole 424 from the opening 430, and the pressure-contact member 426 is fixed to the slider body 402 in the pressure-contact member attachment part 428.

The pressure-contact member 426, as illustrated in FIG. 7, is annularly formed of an elastic material, such as elastic rubber or a spring, and a central axis of a through-hole 432 thereof is arranged coaxially with the endoscope insertion axis 306a.

Accordingly, when the endoscope insertion part 102 is inserted through the endoscope insertion passage 306, as illustrated in FIG. 6, the endoscope insertion part 102 is inserted through the through-hole 432 of the pressure-contact member 426.

In addition, the position of an outer peripheral surface of the pressure-contact member 426 in the opening 430 of the pressure-contact member attachment part 428 substantially coincides with the position of the left side surface 431 of the slider body 402 around the opening 430. That is, the opening 430 of the pressure-contact member attachment part 428 provides a space for arranging the pressure-contact member 426, and as compared to a configuration in which the pressure-contact member 426 is completely housed inside the slider body 402, the slider body 402 is miniaturized, and the external diameter of the overtube body 320 is also made smaller along with this miniaturization. However, a configuration in which the pressure-contact member 426 is completely housed inside the slider body 402 may be adopted.

Additionally, the internal diameter (the diameter of the through-hole 432) of the pressure-contact member 426 is slightly smaller than the external diameter of the endoscope insertion part 102.

Therefore, when the endoscope insertion part 102 is inserted through the through-hole 432 of the pressure-contact member 426, the through-hole 432 is pushed and widened and the pressure-contact member 426 is deformed. An elastic force is generated in the pressure-contact member 426 due to this deformation, and the pressure-contact member 426 is brought into pressure contact (engaged) with the endoscope insertion part 102 inserted through the through-hole 432.

Therefore, a frictional force acts on the relative movement between the endoscope insertion part 102 and the pressure-contact member 426. Then, unless a larger external force than the frictional force is applied between the endoscope insertion part 102 and the pressure-contact member 426, the relative movement does not occur between the endoscope insertion part 102 and the pressure-contact member 426, and the endoscope insertion part 102 and the slider 400 (slider body 402) are brought into a state where they are coupled (engaged) in an interlockable manner via the pressure-contact member 426.

Accordingly, the slider 400 (slider body 402) also integrally moves forward and backward in an interlocking manner with the forward and backward movement of the endoscope insertion part 102 in the forward-rearward direction (axial direction).

In addition, since the coupling here is based on the elastic force of the pressure-contact member 426, the engagement position (a position where the slider 400 is engaged in the endoscope insertion part 102) of the endoscope insertion part 102 coupled to the slider 400 (slider body 402) can be arbitrarily adjusted.

(Description of Treatment Tool-Coupled Part)

The treatment tool-coupled part 422, as illustrated in FIG. 10 is provided on the right side of the slider body 402, and includes a sleeve 440 (sleeve member) that is coupled to the treatment tool insertion part 202, and a guide part 460 that guides the sleeve 440 so as to be movable forward and backward in the direction (forward-rearward direction) of the treatment tool insertion axis 308a.

The sleeve 440 is housed in a sleeve housing space 464 of the guide part 460 to be described below in detail, is supported so as to be movable forward and backward in the forward-rearward direction, and as illustrated in FIG. 7, includes a sleeve body (frame body) 444 that surrounds the outside of the sleeve, and a pressure-contact member 446 that is arranged inside the sleeve.

The sleeve body 444 is formed in a cylindrical shape, and has a through-hole 448 with a larger diameter than the external diameter of at least the treatment tool insertion part 202. The central axis of the through-hole 448 is arranged coaxially with the treatment tool insertion axis 308a within the lumen 324 of the overtube body 320, and secures a space for the treatment tool insertion passage 308.

The pressure-contact member 446 is annularly formed of an elastic material, such as elastic rubber or a spring, and is fitted into the through-hole 448 of the sleeve body 444 and fixed to the sleeve body 444. A central axis of a through-hole 450 of the pressure-contact member 446 is arranged coaxially with the treatment tool insertion axis 308a within the lumen 324 of the overtube body 320.

Therefore, when the treatment tool insertion part 202 is inserted through the treatment tool insertion passage 308, as illustrated in FIG. 6, the treatment tool insertion part 202 is inserted through the through-hole 450 of the pressure-contact member 446.

Additionally, the internal diameter (the diameter of the through-hole 450) of the pressure-contact member 446 is slightly smaller than the external diameter of the treatment tool insertion part 202.

Therefore, when the treatment tool insertion part 202 is inserted through the through-hole 450 of the pressure-contact member 446, the through-hole 450 is pushed and widened and the pressure-contact member 446 is deformed. An elastic force is generated in the pressure-contact member 446 due to this deformation, and the pressure-contact member 446 is brought into pressure contact (engaged) with the treatment tool insertion part 202 inserted through the through-hole 450.

Therefore, a frictional force acts on the relative movement between the treatment tool insertion part 202 and the pressure-contact member 446. Then, unless a larger external force than the frictional force is applied between the treatment tool insertion part 202 and the pressure-contact member 446, the relative movement does not occur between the treatment tool insertion part 202 and the pressure-contact member 446, and the treatment tool insertion part 202 and the sleeve 440 are brought into a state where they are coupled (engaged) in an interlockable manner via the pressure-contact member 446.

Accordingly, the sleeve 440 also integrally moves forward and backward in an interlocking manner with the forward and backward movement of the treatment tool insertion part 202 in the forward-rearward direction (axial direction).

Additionally, the sleeve 440 also rotates with respect to the slider body 402 in an interlocking manner with the rotation around the axis of the treatment tool insertion part 202.

In addition, since the coupling between the treatment tool insertion part 202 and the sleeve 440 herein is based on the elastic force of the pressure-contact member 446, the engagement position (a position where the sleeve 440 is engaged in the treatment tool insertion part 202) of the treatment tool insertion part 202 coupled to the sleeve 440 can be arbitrarily adjusted.

Additionally, a region where the endoscope insertion part 102 is fixed to the endoscope-coupled part 420 of the slider 400 is referred to as an endoscope fixed region, and a region where the treatment tool insertion part 202 is fixed to the treatment tool-coupled part 422 of the slider 400 is referred to as a treatment tool fixed region. In the present form, the endoscope fixed region is equivalent to a region of an inner peripheral surface of the pressure-contact member 426 that is brought into pressure contact with the outer peripheral surface of the endoscope insertion part 102, and the treatment tool fixed region is equivalent to a region of an inner peripheral surface of the pressure-contact member 446 that is brought into pressure contact with the outer peripheral surface of the treatment tool insertion part 202. In this case, it is desirable that the endoscope fixed region is configured so as to become longer in the axial direction than the treatment tool fixed region.

Meanwhile, the guide part 460 of the treatment tool-coupled part 422, as illustrated in FIGS. 7 and 9, has a guide surface 462 that extends in the direction of the treatment tool insertion axis 308a (reference axis 300a) within the lumen 324 of the overtube body 320.

The guide surface 462 is curved in a U-shape toward an opening in a section orthogonal to the reference axis 300a, and as illustrated in FIG. 7, an inner peripheral surface of the overtube body 320 (outer wall 322) is arranged so as to face the opening of the guide surface 462, within the lumen 324 of the overtube body 320.

Accordingly, a space surrounded by the guide surface 462 and the inner peripheral surface of the overtube body 320 is formed as the sleeve housing space 464 of the guide part 460.

The sleeve housing space 464 is formed at a position where the treatment tool insertion axis 308a is inserted therethrough, and extends along the treatment tool insertion axis 308a.

The sleeve 440 is housed and arranged in the sleeve housing space 464 as described above, and a central axis of the sleeve 440 is arranged coaxially with the treatment tool insertion axis 308a.

In the sleeve housing space 464, an outer peripheral surface of the sleeve 440 comes in contact with or approaches the guide surface 462 and the inner peripheral surface of the overtube body 320.

Accordingly, in the sleeve housing space 464, the sleeve 440 is supported so as to be movable in the forward-rearward direction and rotatable around the axis, and is supported in a state where the movement of the sleeve in the upward-downward direction and in the leftward-rightward direction is restricted.

Additionally, the guide part 460 (slider body 402), as illustrated in FIGS. 9 and 10, has end edge parts 466 and 468, which are formed to protrude in a direction orthogonal to the guide surface 462 along an end edge of the guide surface 462, respectively, on the base end side and the distal end side thereof.

The end edge parts 466 and 468 abut against the end part of the sleeve 440 to restrict the movement of the sleeve 440, when the sleeve 440 arranged in the sleeve housing space 464 moves forward and backward in the forward-rearward direction.

Therefore, a range (movable range) where the sleeve 440 moves forward and backward in the forward-rearward direction with respect to the slider body 402 is limited with a position where the sleeve abuts against the end edge part 466 being defined as a rear end and a position where the sleeve abuts against the end edge part 468 being defined as a front end. However, the rear end and the front end of the movable range of the sleeve 440 may not be restricted by the end edge part 466 and the end edge part 468.

In addition, in the present embodiment, the sleeve housing space 464 of the guide part 460 is formed by the guide surface 462 of the slider body 402 and the inner peripheral surface of the overtube body 320. Therefore, as compared to a configuration in which the sleeve housing space 464 is formed only by the slider body 402 and the sleeve 440 is completely housed inside the slider body 402, the slider body 402 is miniaturized, and the external diameter of the overtube body 320 is also made smaller along with this miniaturization. However, a configuration in which the sleeve 440 is completely housed inside the slider body 402 may be adopted.

(Action of Slider when Endoscope and Treatment Tool are Coupled)

According to the slider 400 configured as described above, the endoscope insertion part 102 inserted through the endoscope insertion passage 306 of the overtube 300 and the slider body 402 are coupled, and the treatment tool insertion part 202 inserted through the treatment tool insertion passage 308 of the overtube 300 and the sleeve 440 are coupled.

Figure 11:
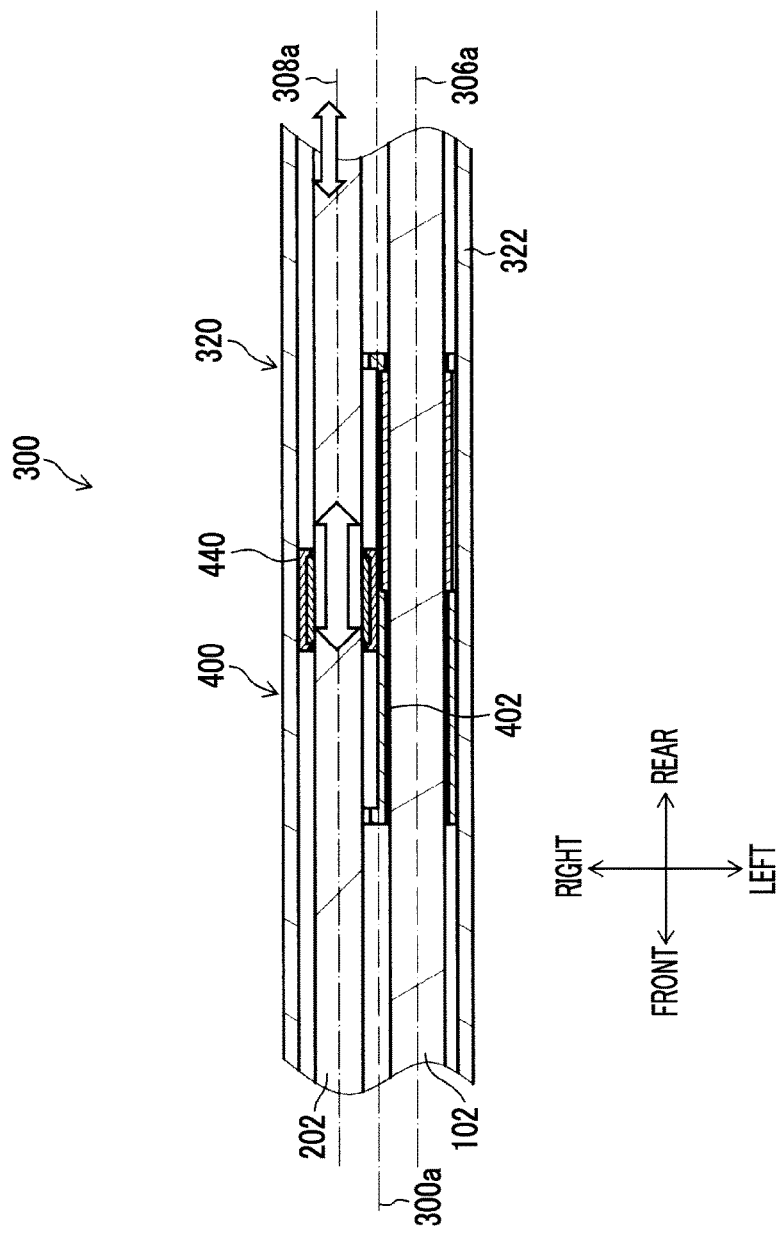
FIG. 11 is an explanatory view used for the description of the action of the slider.

As illustrated in FIG. 11, it is supposed that a surgeon performs a forward and backward movement for moving the treatment tool insertion part 202 forward and backward in the axial direction (forward-rearward direction) in a state where the sleeve 440 has not reached the rear end and the front end of the movable range thereof with respect to the slider body 402.

In this case, when the sleeve 440 has moved forward and backward within the movable range thereof with respect to the slider body 402, the slider body 402 does not move with respect to the forward and backward movement of the treatment tool insertion part 202. Therefore, the dead zone where the endoscope insertion part 102 does not interlock with the forward and backward movement of the treatment tool insertion part 202 is present.

Figure 12:
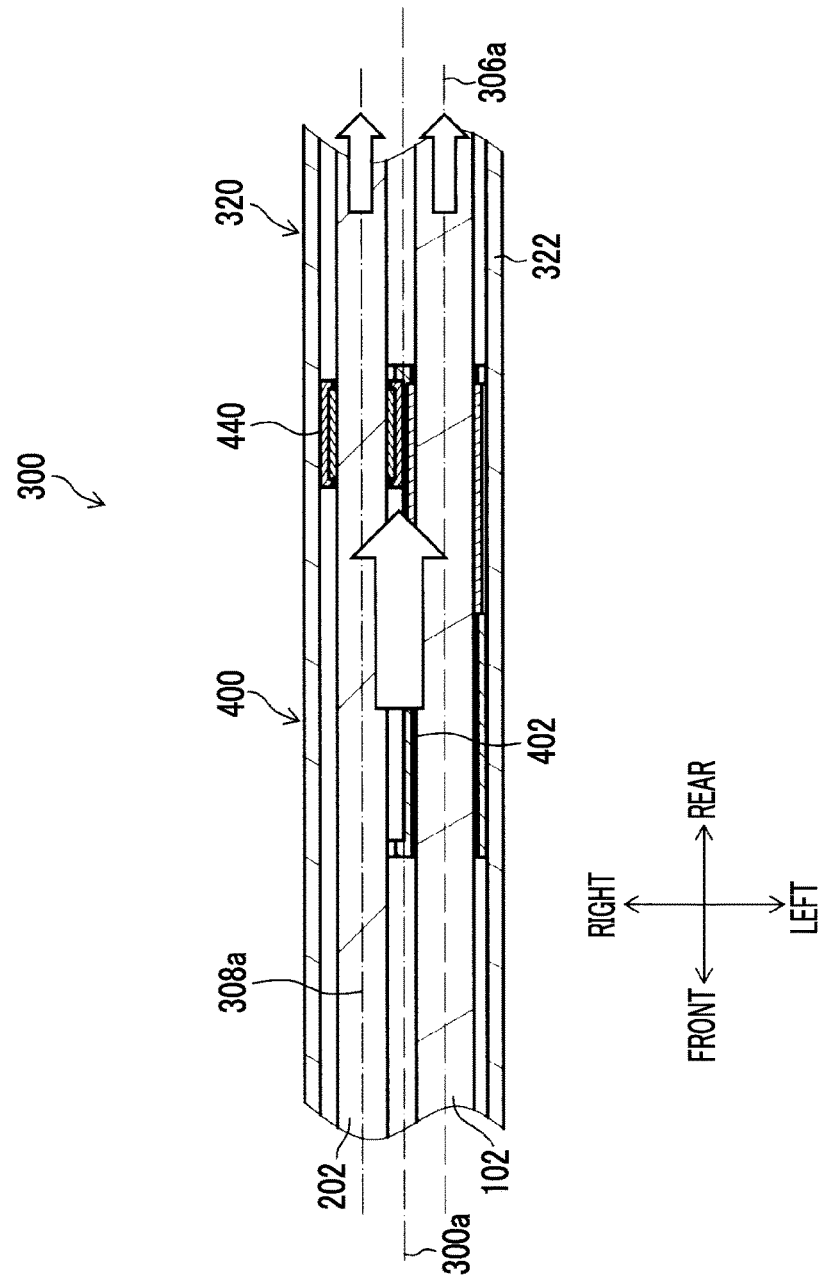
FIG. 12 is an explanatory view used for the description of the action of the slider.

On the other hand, as illustrated in FIG. 12, if the treatment tool insertion part 202 is moved backward in a state where the sleeve 440 reaches the rear end of the movable range thereof with respect to the slider body 402, the sleeve 440 and the slider body 402 move backward with respect to the overtube body 320 together with the treatment tool insertion part 202. Accordingly, the endoscope insertion part 102 moves backward in an interlocking manner with the treatment tool insertion part 202.

Figure 13:
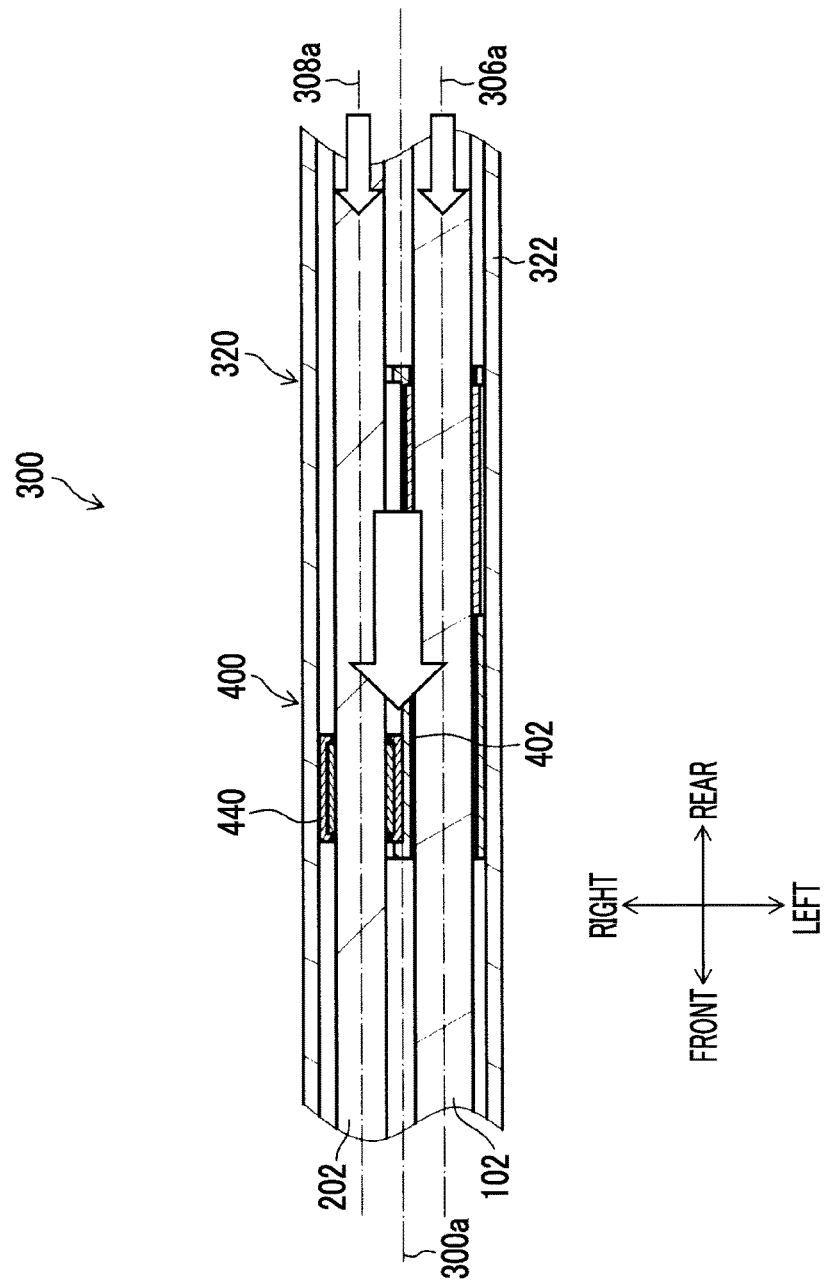
FIG. 13 is an explanatory view used for the description of the action of the slider.

Similarly, as illustrated in FIG. 13, if the treatment tool insertion part 202 is moved forward in a state where the sleeve 440 reaches the front end of the movable range thereof with respect to the slider body 402, the sleeve 440 and the slider body 402 move forward with respect to the overtube body 320 together with the treatment tool insertion part 202. Accordingly, the endoscope insertion part 102 moves forward in an interlocking manner with the treatment tool insertion part 202.

Therefore, when the treatment tool insertion part 202 has been largely displaced in the axial direction as described above (when the forward and backward movement of a large amplitude has been performed), the endoscope insertion part 102 is displaced in the axial direction in an interlocking manner with the treatment tool insertion part 202, and when the displacement of the treatment tool insertion part 202 in the axial direction is small (when the forward and backward movement of a small amplitude is performed), the endoscope insertion part 102 is not displaced in the axial direction.

Figure 14:
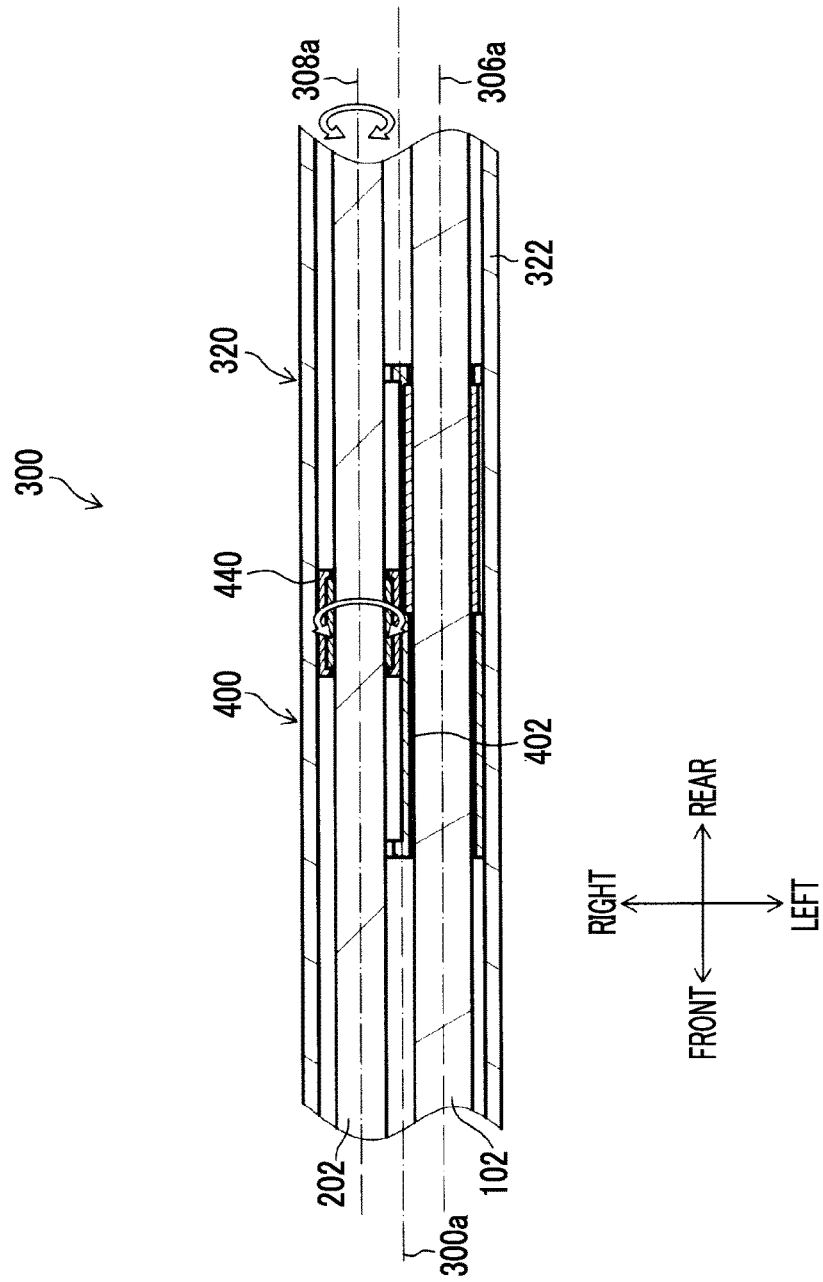
FIG. 14 is an explanatory view used for the description of the action of the slider.

Additionally, in the present embodiment, the slider body 402 is restricted only in forward and backward movement in the forward-rearward direction, whereas the sleeve 440 is supported so as to be rotatable around the axis with respect to the slider body 402. Therefore, as illustrated in FIG. 14, when the treatment tool insertion part 202 is operated to rotate around the axis, the slider body 402 does not rotate, and the treatment tool insertion part 202 and the sleeve 440 rotate around the axis.

Therefore, the rotational angle of the treatment tool insertion part 202 around the axis can be changed, without changing the positions of the endoscope insertion part 102 and the treatment tool insertion part 202 (the positions thereof within a body cavity) with respect to the overtube 300.

That is, when a treatment is performed on a predetermined affected part by inserting the endoscope insertion part 102 and the treatment tool insertion part 202 through the overtube 300 inserted into a body wall, in a general procedure, the endoscope 100 is used such that the position of the endoscope insertion part 102 in the upward-downward direction and in the leftward-rightward direction and the rotational angle thereof around the axis are fixed.

Meanwhile, the rotational operation of the treatment tool insertion part 202 around the axis is appropriately performed similar to the forward and backward movement so that the treatment tool 200 is easily operated by a surgeon.

In the overtube 300 of the present embodiment, the endoscope insertion part 102 and the treatment tool insertion part 202 are coupled by the slider 400. Thus, there is a concern that the positions of the endoscope insertion part 102 in the upward-downward direction and in the leftward-rightward direction and the rotational angle thereof around the axis may fluctuate due to the rotational operation or the like of the treatment tool insertion part 202.

However, since operations other than the forward and backward movement of the slider 400 are restricted as described above, the treatment tool insertion part 202 can be rotated around the axis without changing the positions of the endoscope insertion part 102 in the upward-downward direction and in the leftward-rightward direction and the rotational angle thereof around the axis, and the degree of freedom (five degrees of freedom) required for the operation of forceps is obtained. In addition, the five degrees of freedom of the operation of the forceps are the movement of the forceps with respect to an internal organ, and indicate five movements of the forceps including the movements of the forceps in the longitudinal direction, the transverse direction, and the forward and backward movement direction, the rotation of the forceps, and the opening/closing operation of the forceps.

(Operating Conditions of Slider)

Next, the operating conditions of the slider 400 will be described. Here, forces that act on the respective members related to the operation of the slider 400 are defined as follows.

A force with which the pressure-contact member 426 of the endoscope-coupled part 420 fixes the endoscope insertion part 102 at a fixed position of the outer peripheral surface thereof is referred to as a fixing force for fixing the slider body 402 to the endoscope insertion part 102, and the magnitude of the fixing force (the fixing force for fixing the endoscope insertion part 102 at the fixed position in the axial direction) with respect to the axial direction (forward-rearward direction) is defined as F1.

Similarly, a force with which the pressure-contact member 446 of the sleeve 440 in the treatment tool-coupled part 422 fixes the treatment tool insertion part 202 at a fixed position of the outer peripheral surface thereof is referred to as a fixing force for fixing the sleeve 440 to the treatment tool insertion part 202, and the magnitude of the fixing force with respect to the axial direction (forward-rearward direction) is defined as F2.

Meanwhile, a frictional force received from the valve member 346 when the endoscope insertion part 102 moves forward and backward is defined as F3, and a frictional force received from the valve member 348 when the treatment tool insertion part 202 moves forward and backward is defined as F4.

Additionally, a frictional force received from a peripheral member when the sleeve 440 moves forward and backward with respect to the slider body 402 is defined as F5, and a frictional force received from the peripheral member when the slider body 402 moves forward and backward with respect to the overtube body 320 is defined as F6.

(a) Conditions in which Endoscope and Treatment Tool are Interlocked with Each Other when Forward and Backward Movement Width of Treatment Tool is Large When the treatment tool insertion part 202 has been moved forward and backward (when the treatment tool insertion part has been markedly moved forward and backward), as conditions in which the endoscope insertion part 102 and the treatment tool insertion part 202 are integrally moved forward and backward via the slider 400, the fixing forces F1 and F2, and the frictional force F3 satisfy the following conditions (1) and (2).

$$F1 > F3 \quad (1)$$

$$F2 > F3 \quad (2)$$

Accordingly, if the sleeve 440 reaches the rear end or the front end of the movable range thereof with respect to the slider body 402 as illustrated in FIG. 12 or 13 when the treatment tool insertion part 202 has been moved forward and backward, the sleeve 440 receives the frictional force F3 of the valve member 346 via the slider body 402 and the endoscope insertion part 102. In this case, since the endoscope insertion part 102 and the slider body 402 are coupled by a larger fixing force F1 than the frictional force F3 and the treatment tool insertion part 202 and the sleeve 440 are coupled by a larger fixing force F2 than the frictional force F3, the slider body 402 moves forward and backward in an interlocking manner with the forward and backward movement of the treatment tool insertion part 202, and the endoscope insertion part 102 moves forward and backward in an interlocking manner with the forward and backward movement of the slider body 402.

Therefore, when the treatment tool insertion part 202 has been moved forward and backward, there is no case where, due to the frictional force of the valve member 346, the engagement position of the endoscope insertion part 102 engaged with the slider body 402 shifts and the engagement position of the treatment tool insertion part 202 engaged with the sleeve 440 also shifts.

In addition, when the treatment tool insertion part 202 has been moved forward and backward, as a condition for moving the slider body 402 forward and backward with respect to the overtube body 320 in an interlocking manner with this operation, the fixing force F2 and the frictional force F6 satisfy the following condition (3).

$$F2 > F6 \quad (3)$$

Similarly, when the endoscope insertion part 102 has been moved forward and backward, in order to move the endoscope insertion part 102 and the treatment tool insertion part 202 forward and backward integrally via the slider 400, the fixing forces F1 and F2, and the frictional force F4 satisfy the following conditions (4) and (5).

$$F1 > F4 \quad (4)$$

$$F2 > F4 \quad (5)$$

Additionally, when the endoscope insertion part 102 has been moved forward and backward, as a condition for moving the slider body 402 forward and backward with respect to the overtube body 320 in an interlocking manner with this operation, the fixing force F1 and the frictional force F6 satisfy the following condition (6).

$$F1 > F6 \quad (6)$$

(a) Conditions in which Endoscope and Treatment Tool are not Interlocked with Each Other when Forward and Backward Movement Width of Treatment Tool is Small When the treatment tool insertion part 202 has been moved forward and backward with a small width, as a condition for moving only the treatment tool insertion part 202 forward and backward without moving the endoscope insertion part 102 forward and backward as illustrated in FIG. 11, the frictional forces F3, F5, and F6 satisfy the following condition (7).

$$F3 + F6 > F5 \quad (7)$$

As a result, as illustrated in FIG. 11, when the movement width of the treatment tool insertion part 202 is small, the endoscope insertion part 102 does not move, and when the forward and backward movement width of the treatment tool insertion part 202 is large, the endoscope insertion part 102 moves. That is, when the forward and backward movement width of the treatment tool insertion part 202 is small, the sleeve 440 moves forward and backward only within the slider body 402, and the slider body 402 itself does not move with respect to the overtube body 320. Thus, the endoscope insertion part 102 does not move forward and backward in the axial direction (forward-rearward direction).

In addition, since F6 is considered to be substantially 0 when the frictional resistance of the slider body 402 with respect to the overtube body 320 is small enough to be ignored compared to the frictional force between the endoscope insertion part 102 and the valve member 346, the condition (7) becomes F3>F5.

On the other hand, when the forward and backward movement width of the treatment tool insertion part 202 is large, the sleeve 440 moves forward and backward within the slider body 402, is struck against the distal end side or the base end side of the slider body 402 and moves the slider body 402 itself with respect to the overtube body 320. Thus, the endoscope insertion part 102 coupled to the slider body 402 also moves forward and backward.

(c) Conditions for Adjustment of Length of Treatment Tool Insertion Part 202

As a condition for adjusting the length of the treatment tool insertion part 202 while gripping the endoscope 100 and the treatment tool 200, it is preferable that the fixing force F1 and F2 satisfy the following condition (8).

$$F1 > F2 \quad (8)$$

Accordingly, even when the treatment tool insertion part 202 has been moved forward and backward using the overtube body 320 or even when the treatment tool insertion part 202 has been moved forward and backward using the endoscope insertion part 102, the engagement position of the treatment tool insertion part 202 using the slider body 402 can be changed without changing the engagement position of the endoscope insertion part 102 engaged with the slider body 402.

When the length of the treatment tool insertion part 202 is adjusted by moving the treatment tool insertion part 202 forward and backward using the overtube body 320, frictional forces are generated between the sleeve 440 and the treatment tool insertion part 202 and between the valve member 348 and the treatment tool insertion part 202. Thus, the operating force required for the forward and backward movement of the treatment tool insertion part 202 is F2+F4. Therefore, in order to allow a surgeon to perform such an adjustment operation without feeling stress, it is desirable that the fixing force F2 and the frictional force F4 satisfy the following condition (9).

$$F2 + F4 < 10 \ N (N \text{ is Newtons}) \quad (9)$$

Meanwhile, when the length of the treatment tool insertion part 102 is adjusted by moving the treatment tool insertion part 202 forward and backward using the endoscope insertion part 202, if F4>F3 is satisfied, the same frictional forces as above are generated. Thus, it is desirable to satisfy Expression (9). If F3<F4 is satisfied, frictional forces are generated between the sleeve 440 and the treatment tool insertion part 202 and between the valve member 346 and the endoscope insertion part 102. Thus the operating force required for the forward and backward movement of the treatment tool insertion part 202 is F2+F3. Therefore, in order to allow a surgeon to perform such an adjustment operation without feeling stress, it is desirable that the fixing force F2 and the frictional force F3 satisfy the following condition (10).

$$F2 + F3 < 10 \ N (N \text{ is Newtons}) \quad (10)$$

The invention is effective not only when both of the condition (9) and the condition (10) are satisfied but also when only any one of these conditions is satisfied.

In addition, even when the fixing forces F1 and F2 satisfy the following Expression (11), the length of the treatment tool insertion part 202 can be adjusted. In this case, however, the engagement position between the endoscope insertion part 102 and the slider body 402 may move, and the positional adjustment between the slider body 402 and the endoscope insertion part 102 may be separately required.

$$F1 < F2 \quad (11)$$

In order to allow a surgeon to perform such an adjustment operation without feeling stress, it is desirable that the fixing force F1 and the frictional force F3 or F4 satisfy the following condition (12) or (13).

$$F1 + F4 < 10 \ N (N \text{ is Newtons}) \quad (12)$$

$$F1 + F3 < 10 \ N (N \text{ is Newtons}) \quad (13)$$

(d) Conditions for Ensuring Excellent Operability

As a condition in which a surgeon can perform the forward and backward movement of the treatment tool insertion part 202 without feeling stress, it is preferable that the frictional forces F3, F4, and F6 satisfy the following condition (14).

$$F3 + F4 + F6 < 10 \ N (N \text{ is Newtons}) \quad (14)$$

In this way, by setting the required operating force (F3+F4+F6) when a surgeon moves the treatment tool insertion part 202 forward and backward markedly, a surgeon can secure excellent operability without feeling stress.

(e) Conditions for Preventing Overtube from Shifting with Respect to Body Wall

As a condition in which the overtube 300 (overtube body 320) is prevented from shifting due to the forward and backward movement of the treatment tool insertion part 202, if the fixing force of the overtube 300 in the forward-rearward direction (axial direction) with respect to a body wall is defined as Ft, the fixing force Ft and the frictional forces F3 and F4 satisfy the following condition (15).

$$F_t > F3 + F4 \quad (15)$$

Accordingly, even if the treatment tool insertion part 202 has been moved forward and backward, the overtube 300 (overtube body 320) inserted into a body wall is fixed in a stable state without shifting. Thus, it is possible to secure excellent operability.

(Other Forms of Slider)

In the above overtube 300, a supporting mechanism of the slider 400 adapted to be capable of moving the slider 400 forward and backward only in the forward-rearward direction with respect to the overtube body 320 is not limited to the above form.

Figure 15:
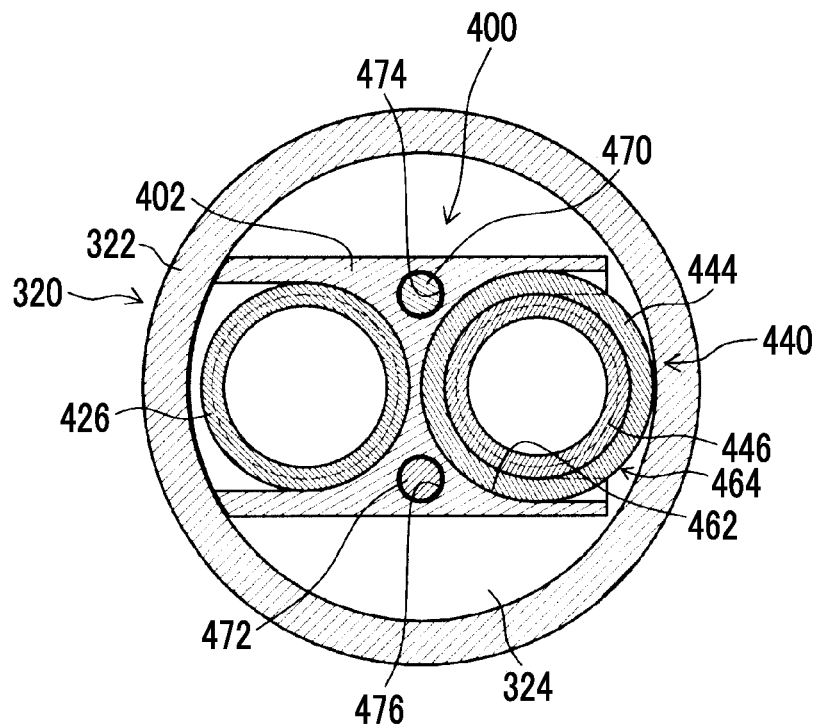
FIG. 15 is a sectional view illustrating another embodiment of a supporting mechanism of the slider in the overtube.

FIG. 15 is a sectional view illustrating another form of the overtube 300 by the section orthogonal to the reference axis 300a. In addition, the same reference signs will be given to constituent elements of the same or similar actions as those of the above form, and the description thereof will be omitted.

In the form illustrated in this drawing, guide rods 470 and 472, which are laid from the base end (base end cap 340) to the distal end (distal end cap 360), are arranged along the direction of the reference axis 300a at the upper part and the lower part within the lumen 324 of the overtube body 320.

Meanwhile, guide holes 474 and 476, which penetrate from the base end to the front end, are formed at the upper part and the lower part of the slider body 402 of the slider 400.

The guide rods 470 and 472 are respectively inserted through the guide holes 474 and 476, and the slider 400 is supported within the lumen 324.

Accordingly, the slider 400 is supported so as to be movable forward and backward only in the forward-rearward direction with respect to the overtube body 320.

Figure 16:
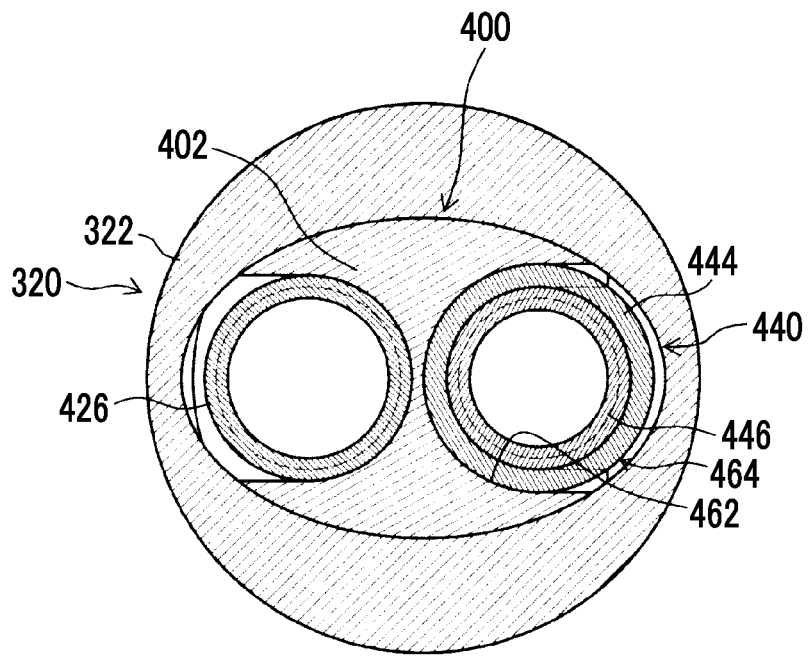
FIG. 16 is a sectional view illustrating still another embodiment of the supporting mechanism of the slider in the overtube.

FIG. 16 is a sectional view illustrating still another form of the overtube 300 by the section orthogonal to the reference axis 300a. In addition, the same reference signs will be given to constituent elements of the same or similar actions as those of the above form, and the description thereof will be omitted.

As illustrated in this drawing, the inner peripheral surface of the overtube body 320 (outer wall 322), that is, the outer shape of the lumen 324, is formed in an elliptical shape in the section orthogonal to the reference axis 300a.

Meanwhile, the slider 400 is formed so that the outer peripheral surface of the slider body 402 that is a frame body has a shape along an ellipse of the same shape as the lumen 324 in the section orthogonal to the reference axis 300a and the outer peripheral surface of the slider body 402 contacts or approaches the inner peripheral surface of the overtube body 320.

Accordingly, the slider 400 is supported so as to be movable forward and backward only in the forward-rearward direction with respect to the overtube body 320.

In addition, the shape of the slider is not limited to this, and the shape of the inner peripheral surface of the overtube body 320 and the shape of the slider body 402 in the section orthogonal to the reference axis 300a only has to be a combination of non-rotatable shapes. For example, in the forms illustrated in FIG. 7 and FIG. 15, if the shape of the inner peripheral surface of the overtube body 320 is formed in an elliptical shape as illustrated in FIG. 16 and the inner peripheral surface of the overtube body 320 is circumscribed on the slider body 402, similar to the form of FIG. 16, special guide means, such as the form of the protruding strips 408 and 410, the guide plates 374 and 376 in the form of FIG. 7 and the guide rods 470 and 472 and the guide holes 474 and 476 in the form of FIG. 15, can be made unnecessary.

(Description of Inner Needle)

Next, an inner needle 500 to be used after being mounted on the overtube 300 when the overtube 300 is inserted into a body wall will be described.

Figure 17:
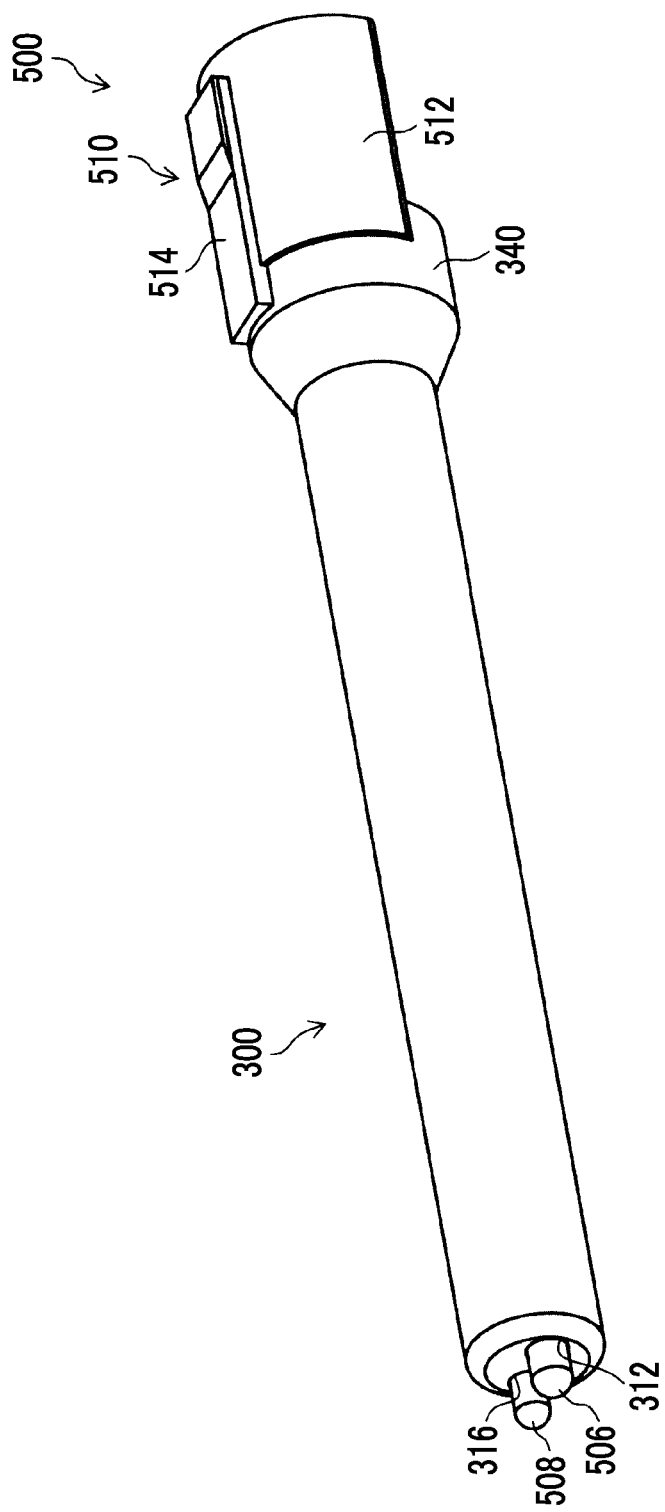
FIG. 17 is a perspective view illustrating a state where an inner needle has been mounted on the overtube, from the front upper left.
Figure 18:
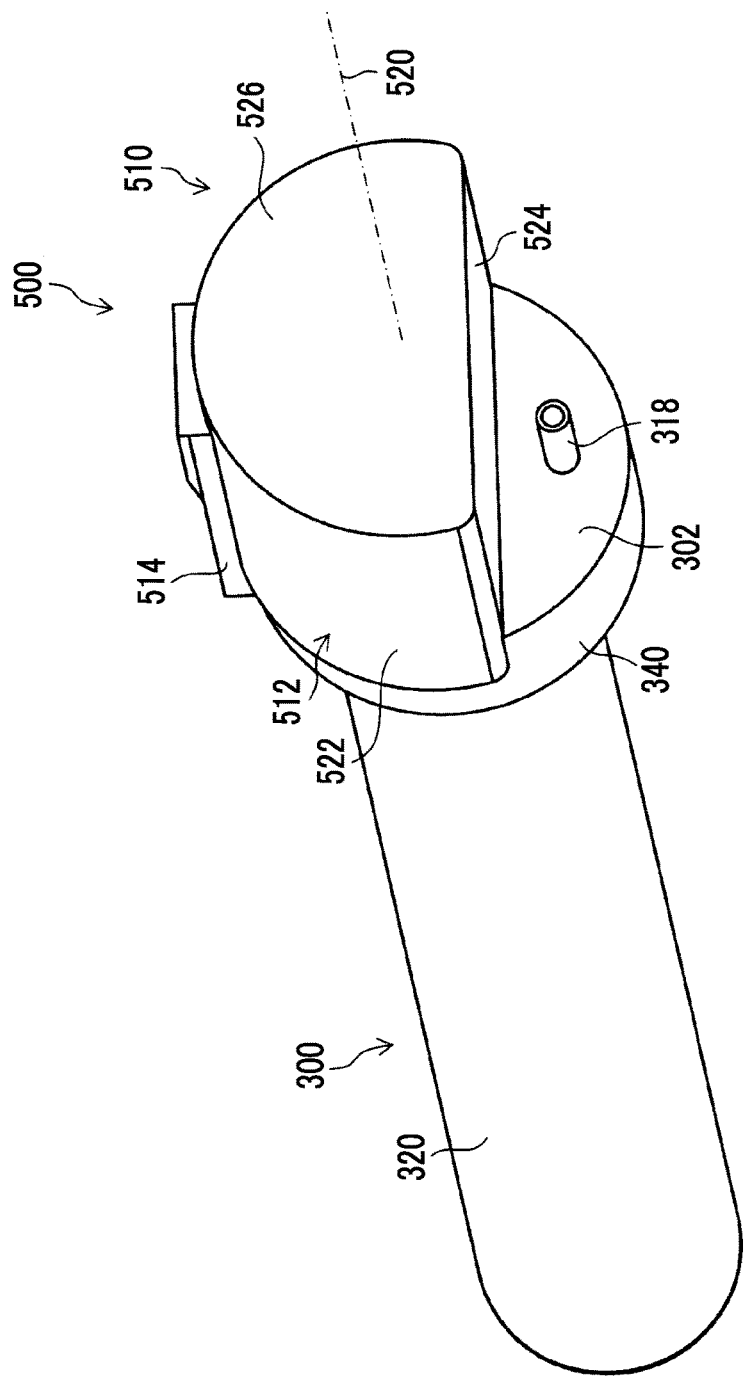
FIG. 18 is a perspective view illustrating a state where the inner needle has been mounted on the overtube, from the rear lower left.
Figure 19:
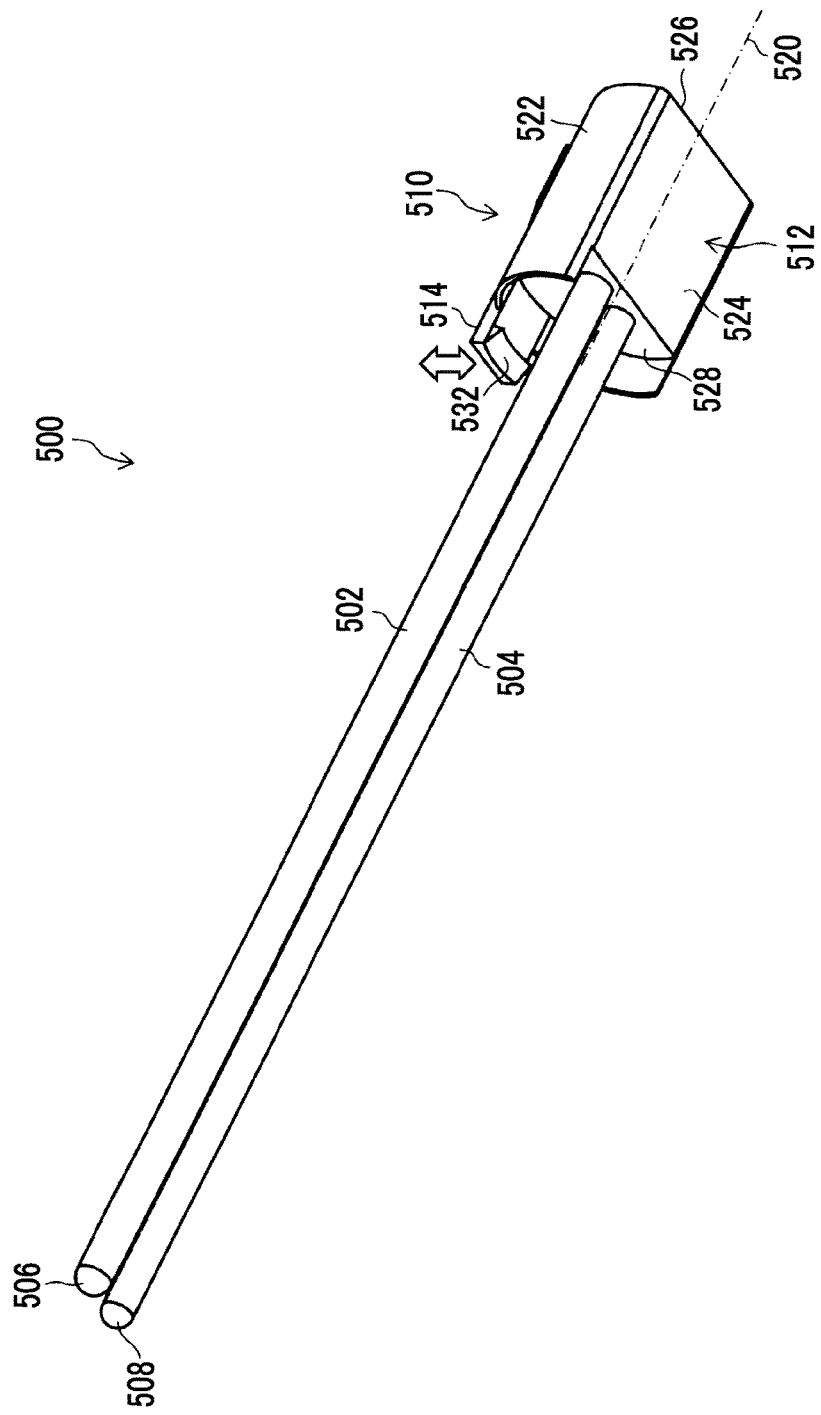
FIG. 19 is a perspective view illustrating the inner needle from the front lower left.

FIGS. 17 and 18 are respectively perspective views illustrating a state where the inner needle 500 has been mounted on the overtube 300 from the front upper left and from the rear lower left, and FIG. 19 is a perspective view illustrating only the inner needle 500 from the front lower left. In addition, the relationship of front and rear, left and right, and up and down of the inner needle 500 follows the relationship of front and rear, left and right, and up and down of the overtube 300 when being mounted on the overtube 300 as illustrated in FIG. 17.

As illustrated in these drawings, the inner needle 500 is constituted of two rod parts 502 and 504 that are formed in an elongated shape, distal end parts 506 and 508 that are respectively formed at the distal ends of the rod parts 502 and 504, and a head part 510 that is provided on the base end sides of the rod parts 502 and 504.

The rod part 502 (first rod part) has a diameter equal to or smaller than the external diameter of the above-described endoscope insertion part 102, and is formed with a size such that the rod part is insertable through the endoscope insertion passage 306. As illustrated in FIGS. 17 and 18, when the inner needle 500 is mounted on (incorporated into) the overtube 300, the s rod part 502 is arranged so as to be inserted through the endoscope insertion passage 306 of the overtube 300.

Additionally, the rod part 502 is formed to be slightly longer than the length of the overtube 300 (endoscope insertion passage 306) in the forward-rearward direction, and when the inner needle 500 has been mounted on the overtube 300, the distal end part 506 of the rod part 502 protrudes by a predetermined length from the endoscope delivery opening 312.

The rod part 504 (second rod part) has a diameter equal to or smaller than the external diameter of the above-described treatment tool insertion part 202, and is formed with a size such that the rod part is insertable through the treatment tool insertion passage 308. As illustrated in FIGS. 17 and 18, when the inner needle 500 has been mounted on the overtube 300, the rod part 504 is arranged so as to be inserted through the treatment tool insertion passage 308 of the overtube 300.

Additionally, the rod part 504 is formed to be slightly longer than the length of the overtube 300 (endoscope insertion passage 306) in the forward-rearward direction, and when the inner needle 500 has been mounted on the overtube 300, the distal end part 508 of the rod part 504 protrudes by a predetermined length from the treatment tool delivery opening 316.

Although the distal end parts 506 and 508 are formed in a curved surface shape and are configured to be dull so that no edge is formed (that is, in a rounded non-edge shape), the distal end parts are adapted to be capable of penetrating a body wall easily.

The head part 510 has a head part body 512 and a locking lever 514.

The head part body 512, as illustrated in FIGS. 18 and 19, has a shape surrounded by a side surface 522 along a column surface having an axis 520 extending in the forward-rearward direction in parallel with the rod parts 502 and 504 as a center having a diameter that approximately coincides with the external diameter of the base end cap 340 of the overtube 300, a lower surface 524 along a plane which is parallel to the axis 520 (parallel to the forward-rearward direction and the leftward-rightward direction) and which intersects the column surface along which the side surface 522 runs, and a rear end surface 526 and a front end surface 528 along a plane orthogonal to the axis 520.

In addition, the axis 520 is arranged coaxially with the reference axis 300a (not illustrated) of the overtube 300 in a state where the inner needle 500 has been mounted on the overtube 300.

The front end surface 528 of the head part body 512 has the base end sides of the rod parts 502 and 504 fixed thereto, and the side surface 522 of the head part body 512 has the locking lever 514 provided along the direction (forward-rearward direction) of the axis 520 at a central part (topmost part) thereof in the circumferential direction.

The locking lever 514 is a constituent element of a fixing mechanism that detachably fixes the head part 510 of the inner needle 500 to the overtube 300, is formed in an elongated plate shape extending along the direction of the axis 520 (refer to FIG. 17), and is supported by the head part body 512 so as to be turnable in such an orientation that a front end part and a rear end part are opposite to each other in the upward-downward direction with the vicinity of the center in the direction of the axis 520 as a fulcrum.

A locking claw 532 (refer to FIG. 19) is provided to protrude from a lower surface side of a distal end part of the locking lever 514, and the locking claw 532, as illustrated in FIGS. 3 and 5, has such a shape that the locking claw is fitted to a locking hole 534 provided in the base end cap 340.

Additionally, a biasing member, such as a coil spring, is arranged at the head part body 512 at a position on a lower surface side of a base end part of the locking lever 514, and the locking lever 514 is biased so that the rear end part faces up and the front end part faces down.

(Action when Inner Needle is Mounted)

Figure 20:
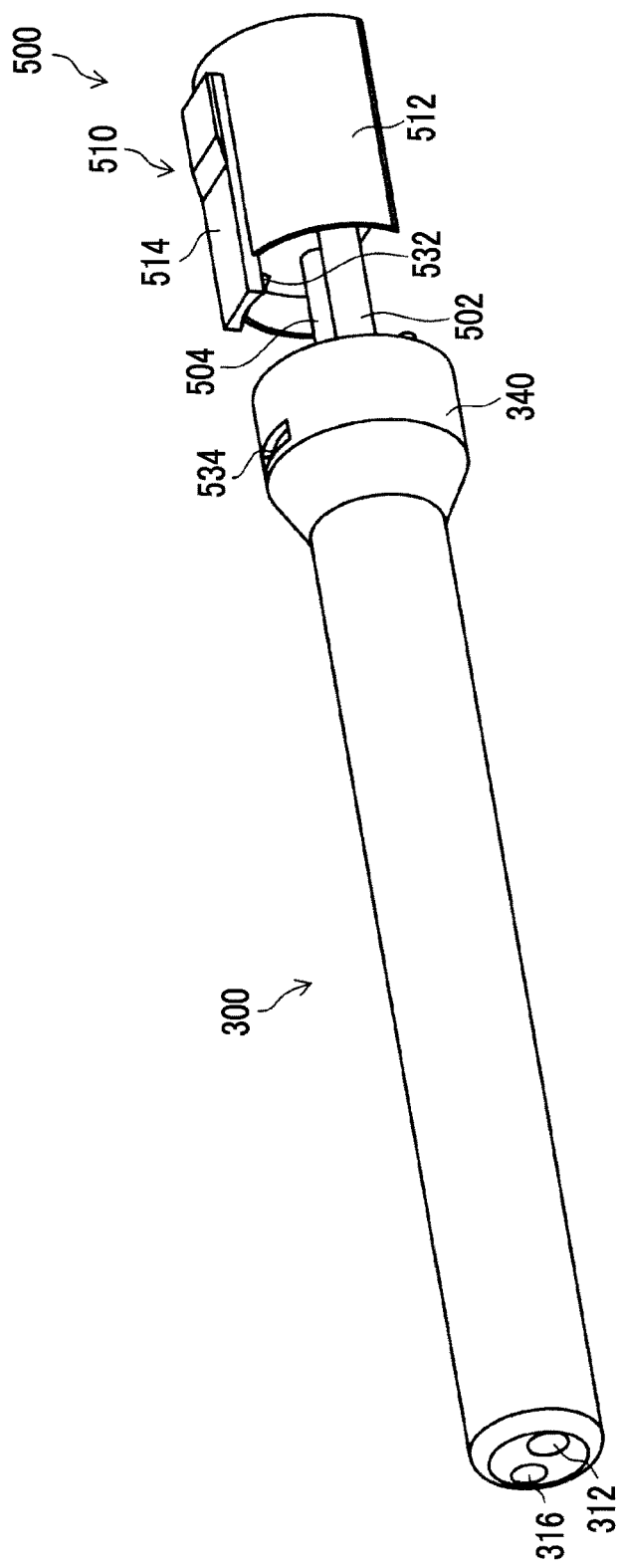
FIG. 20 is a perspective view illustrating a situation in which the inner needle is mounted on the overtube.

According to the inner needle 500 configured as above, if the rod parts 502 and 504 of the inner needle 500 are respectively inserted into the endoscope insertion passage 306 and the treatment tool insertion passage 308 from the endoscope insertion opening 310 and the treatment tool insertion opening 314, respectively, of the overtube 300, as illustrated in FIG. 20, the head part 510 of the inner needle 500 approaches the base end cap 340 of the overtube 300.

Then, if the inner needle 500 is further inserted, as illustrated in FIGS. 17 and 18, the front end surface 528 of the head part body 512 abuts against the base end surface 302 of the overtube 300 (base end cap 340), and the locking claw 532 of the locking lever 514 is fitted to the locking hole 534 of the base end cap 340 and is brought into a state where the inner needle 500 has been mounted on (fixed to) the overtube 300.

In this case, the distal end parts 506 and 508 of the rod parts 502 and 504 of the inner needle 500 are arranged so as to protrude by a predetermined length from the distal end of the overtube 300.

Meanwhile, if the base end part of the locking lever 514 is pressed in a state where the inner needle 500 has been mounted on the overtube 300, the locking claw 532 can be removed from the locking hole 534 of the base end cap 340, and if the inner needle 500 is pulled out to the hand side in that state, the inner needle 500 can be detached from the overtube 300.

Additionally, as described above, the head part body 512 of the inner needle 500 has such a shape that a lower side of a columnar member is cut out by the lower surface 524. That is, the head part body 512 is provided with a cutout part formed by cutting out a portion that interferes with the air supply connector 318 when the inner needle 500 has been mounted on the overtube 300.

Accordingly, the front end surface 528 of the head part body 512 can be made to abut against the base end surface 302 without interfering with the air supply connector 318 provided to protrude from the base end surface 302 of the overtube 300 (base end cap 340) as illustrated in FIG. 18 when the inner needle 500 has been mounted on the overtube 300, and the inner needle 500 can be mounted on the overtube 300 in a stable state.

In addition, the invention is not limited to the above form, and the head part body 512 only has to have the cutout part formed by cutting out the portion of the head part body 512 that interferes with at least the air supply connector 318 when the inner needle 500 has been mounted on the overtube 300. Additionally, since the rotation of the head part body 512 is restricted with respect to the overtube 300 by the rod parts 502 and 504, the head part body does not interfere with the air supply connector 318.

(Wall Surface Member of Overtube Body)

Next, the characteristic parts of the invention will be described. In addition, in the following, the same reference signs will be used for constituent elements of the same or similar actions as the constituent elements in the above basic configuration, and the description thereof will be omitted, and only differences from the above basic configuration will be described.

In the overtube 300 illustrated in FIGS. 3 to 10 in the basic configuration of the above endoscopic surgical device 10, special machining is not performed on the outer peripheral surface, and when the operation or the like of the treatment tool is performed by inserting the endoscope insertion part 102 and the treatment tool insertion part 202 therethrough after being inserted into a body wall, there is a possibility that the overtube 300 may rotate around (around the axis) of the reference axis 300a unintentionally with respect to a body wall or may move forward and backward in the direction (axial direction) of the reference axis 300a.

Particularly, the overtube 300 has a problem in which the position of the distal end of the endoscope insertion part may fluctuate and an observation visual field may fluctuate if the overtube 300 rotates around the axis unlike the overtube through which only the endoscope insertion part is inserted.

Additionally, a situation where the overtube 300 may move forward and backward with respect to a body wall with respect to the forward and backward movement of the treatment tool insertion part 202 due to the frictional force between the slider 400 and the overtube 300 occurs easily.

Thus, the overtube 300 in the present embodiment to be described below has a configuration in which unintended rotation of the overtube 300 around the axis with respect to a body wall or unintended forward and backward movement thereof in the axial direction can be prevented.

Figure 21:
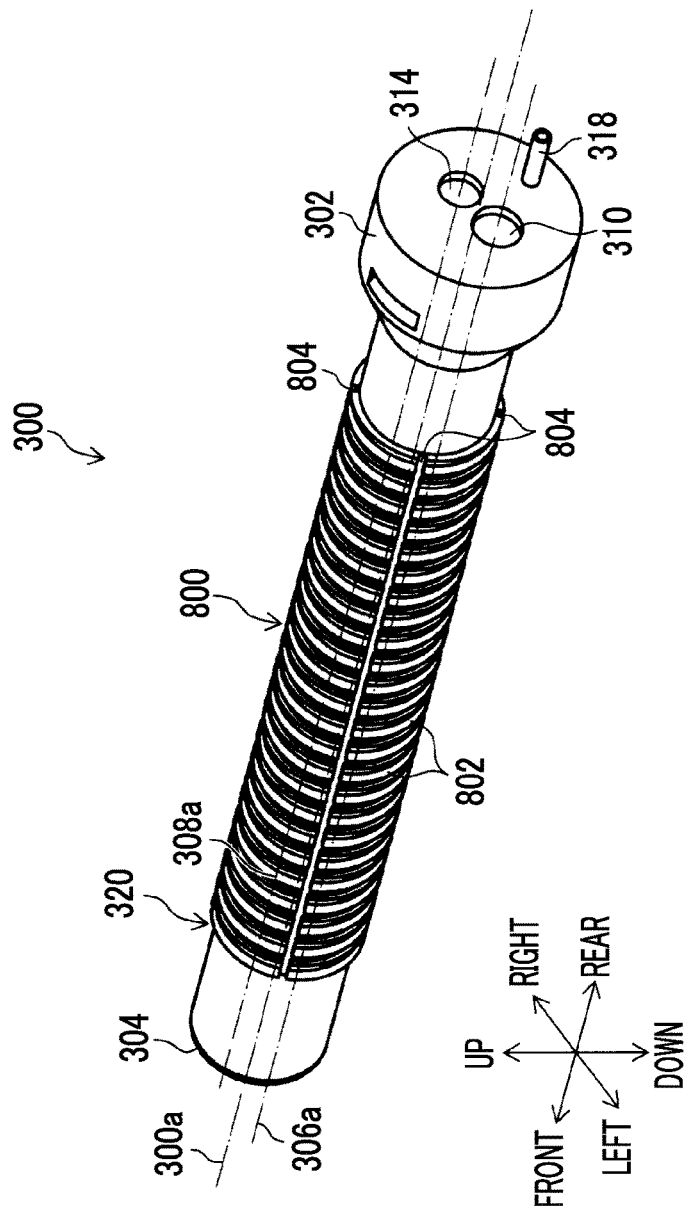
FIG. 21 is a perspective view illustrating the overtube in the endoscopic surgical device to which the present invention is applied.

FIG. 21 is a perspective view illustrating the external appearance of the overtube 300 in the present embodiment.

As illustrated in this drawing, the overtube body 320 includes a wall surface member 800 at an outer peripheral part thereof.

Figure 22:
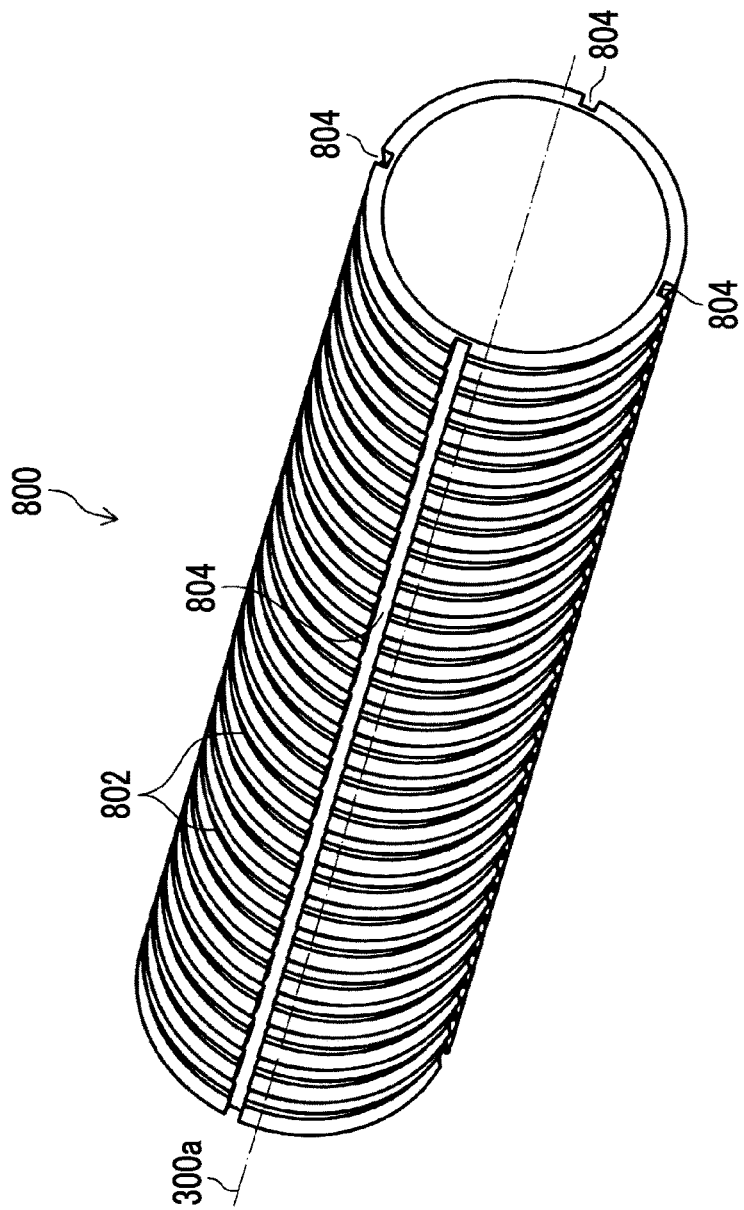
FIG. 22 is a perspective view illustrating a wall surface member in FIG. 21.

The wall surface member 800, as illustrated in FIG. 22, is formed in a cylindrical shape using plastic or the like, is fitted to an outer surface of the overtube body 320, and is fixed to a predetermined position of the overtube body 320.

Annular transverse grooves (recesses) 802 along the circumferential direction (the direction around the axis) and linear longitudinal grooves (recesses) 804 along the axial direction are formed in an outer peripheral part of the wall surface member 800.

(Transverse Grooves of Wall Surface Member)

Figure 23:
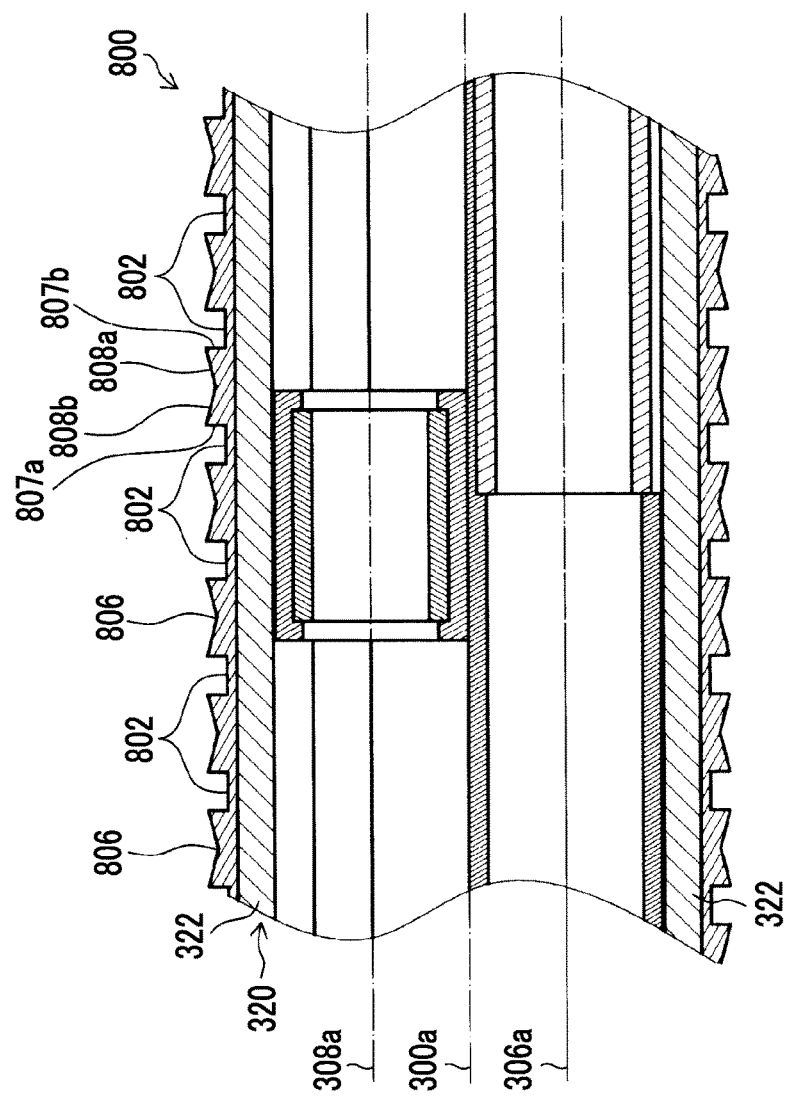
FIG. 23 is a sectional view illustrating a portion of the overtube in FIG. 21 in an enlarged manner.

The transverse grooves 802 form groove parts with a rectangular section, as illustrated in FIG. 23 that is a sectional view illustrating a portion of the overtube 300 in an enlarged manner.

Additionally, a protrusion 806 (projection part) that protrudes in the radial direction with respect to a bottom surface of a transverse groove 802 is formed between the transverse grooves 802 adjacent to each other.

The protrusion 806 has a first side surface 807a on the front side, out of the front and rear side surfaces erected from the bottom surface of the transverse groove 802 to the surface of the protrusion 806, and a second side surface 807b on the rear side.

The first side surface 807a and the second side surface 807b are surfaces along a plane perpendicular to the reference axis 300a.

Additionally, a first tapered surface 808a on the rear side and a second tapered surface 808b on the front side are formed on the surface of the protrusion 806.

The first tapered surface 808a is a tapered surface of which the diameter becomes gradually smaller from the rear side to the front side, and the second tapered surface 808b is a tapered surface of which the diameter becomes gradually smaller from the front side to the rear side. Then, when these surfaces are adjacent to each other, the surface of the protrusion 806 is formed in a V-shape of which a central part becomes depressed in the section of FIG. 23.

By alternately forming the transverse grooves 802 and the protrusions 806 in the direction of the reference axis 300a, a plurality of concavo-convex parts (second concavo-convex parts) each consisting of a transverse groove 802 and a protrusion 806 are periodically provided in the direction of the reference axis 300a at the outer peripheral part of the wall surface member 800.

According to the second concavo-convex parts, a portion of a body wall enters the transverse grooves 802 when the overtube 300 is inserted into the body wall. Therefore, the second concavo-convex parts resist the forward and backward movement in the axial direction (forward-rearward direction) of the overtube 300, and the unintended forward and backward movement of the overtube 300 in the axial direction is prevented.

Additionally, the first tapered surface 808a and the second tapered surface 808b of the surface of the protrusion 806 also respectively have an action that restricts the forward movement and backward movement of the overtube 300 with respect to a body wall (restricts the movements of the overtube to both sides in the axial direction), and contributes to the prevention of the unintended forward and backward movement of the overtube 300 in the axial direction.

That is, the first side surface 807a and the first tapered surface 808a act as a first locking surface that restricts the movement of the overtube 300 to the distal end side in the axial direction, and the second side surface 807b and the second tapered surface 808b act as a second locking surface that restricts the movement of the overtube 300 to the base end side in the axial direction.

In addition, the surface of the protrusion 806 may be flat.

(Longitudinal Grooves of Wall Surface Member)

The longitudinal grooves 804 form groove parts with a rectangular section that has the same depth as the transverse grooves 802. The longitudinal grooves 804 are formed at intervals of 90 degrees in the direction around the axis (the rotational direction centered on the reference axis 300a), and four longitudinal grooves 804 are formed at the outer peripheral part of the wall surface member 800.

Each longitudinal groove 804 constitutes a concavo-convex part (first concavo-convex part) with one protrusion 806 of the protrusions 806 adjacent to both sides in the direction around the axis, in a portion that does not intersect the transverse groove 802. Then, a rotation-preventing wall surface that prevents the rotation of the overtube 300 around the axis is formed by periodically providing a plurality of the concavo-convex parts in the direction around the axis.

According to the first concavo-convex parts, when the overtube 300 is inserted into a body wall, cells of the body wall enter the longitudinal grooves 804. Therefore, the first concavo-convex parts resist the rotation of the overtube 300 around the axis, and the unintended rotation of the overtube 300 around the axis is prevented.

In addition, although the number of longitudinal grooves 804 is four in the present form, the number of longitudinal grooves may be a number other than four. However, since the unintended forward and backward movement of the overtube 300 in the axial direction easily takes place if the number of longitudinal grooves 804 is too large, it is suitable that the number of longitudinal grooves 804 is four.

(Other Configuration Examples of Wall Surface Member)

Figure 24:
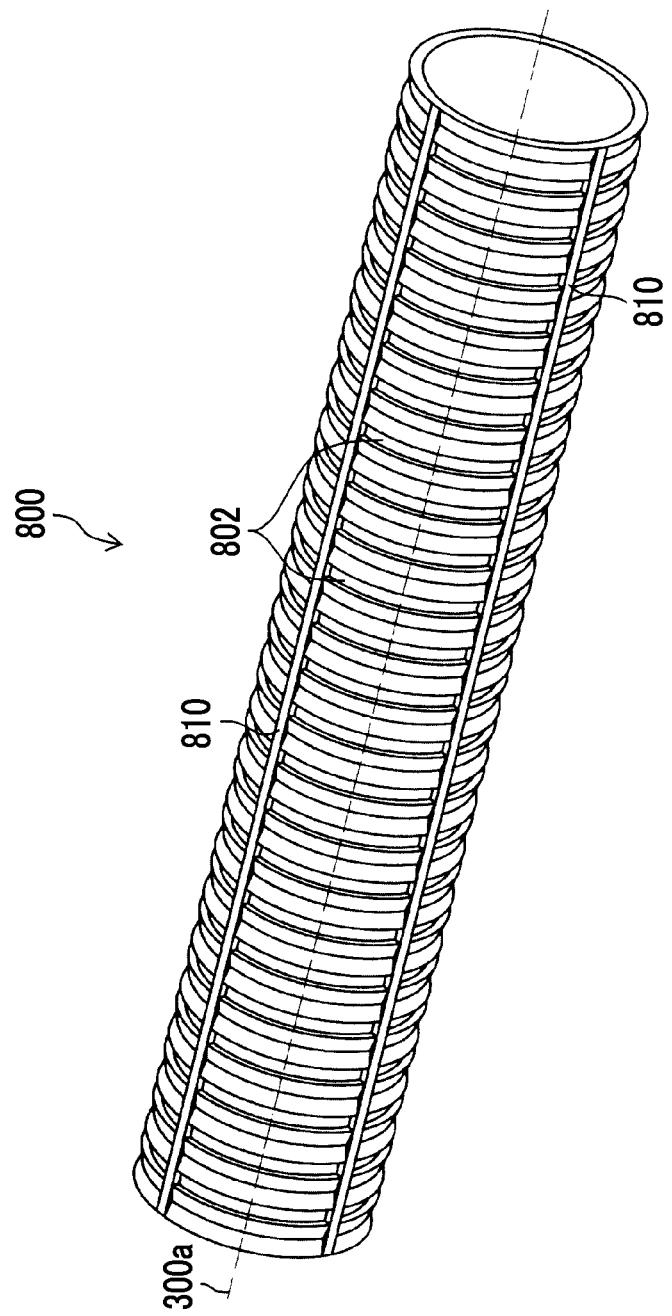
FIG. 24 is a perspective view illustrating the form of the wall surface member provided with protrusions in a longitudinal direction.

Although the linear longitudinal grooves (recesses) 804 along the direction of the reference axis 300a are formed in the above embodiment, as illustrated in FIG. 24, protrusions 810 (projection parts) may be provided instead of the longitudinal grooves 804.

In this case, since each protrusion 810 constitutes a concavo-convex part with one transverse groove 802 of the transverse grooves 802 adjacent to both sides in the rotational direction in a portion that intersects a transverse groove 802, the concavo-convex parts are periodically provided in the rotational direction. Therefore, the unintended rotation of the overtube 300 is prevented by the concavo-convex parts.

Additionally, the surface of the protrusion 810, similar to the surface of the above protrusion 806, consists of a first tapered surface and a second tapered surface, and may be formed so as to have a V-shape in the section orthogonal to the reference axis 300a.

Figure 25:
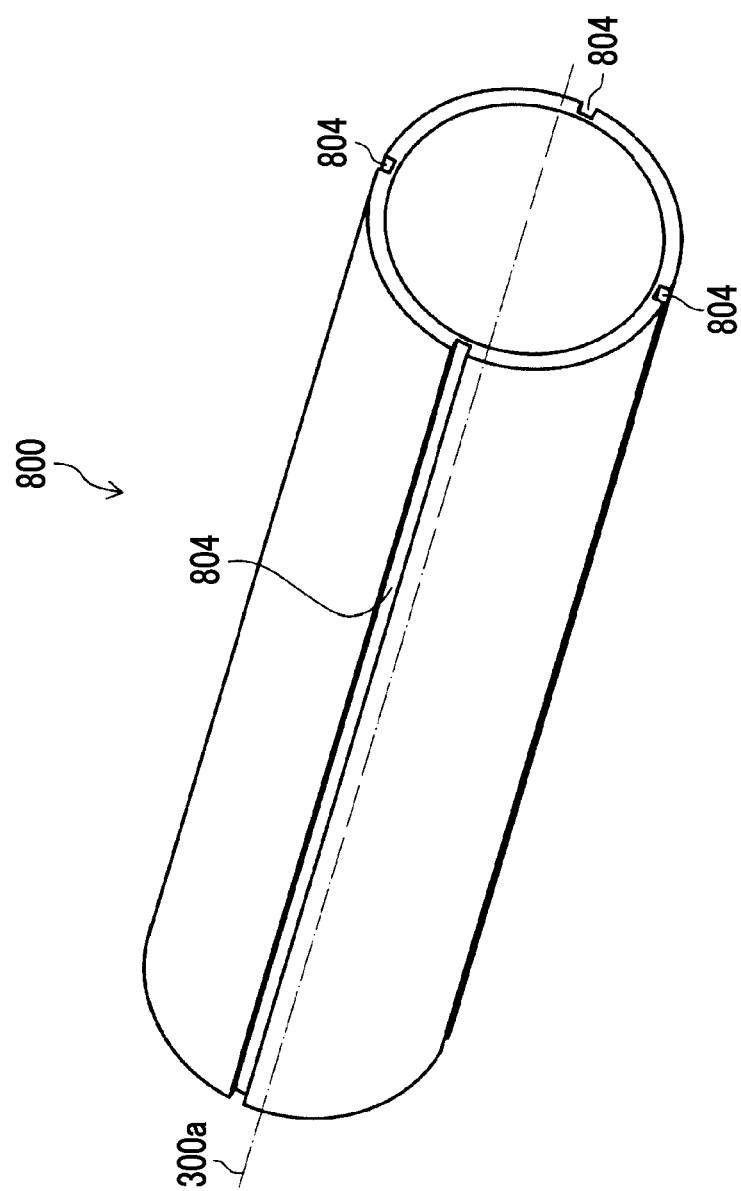
FIG. 25 is a perspective view illustrating the form of the wall surface member provided with grooves only in the longitudinal direction.
Figure 26:
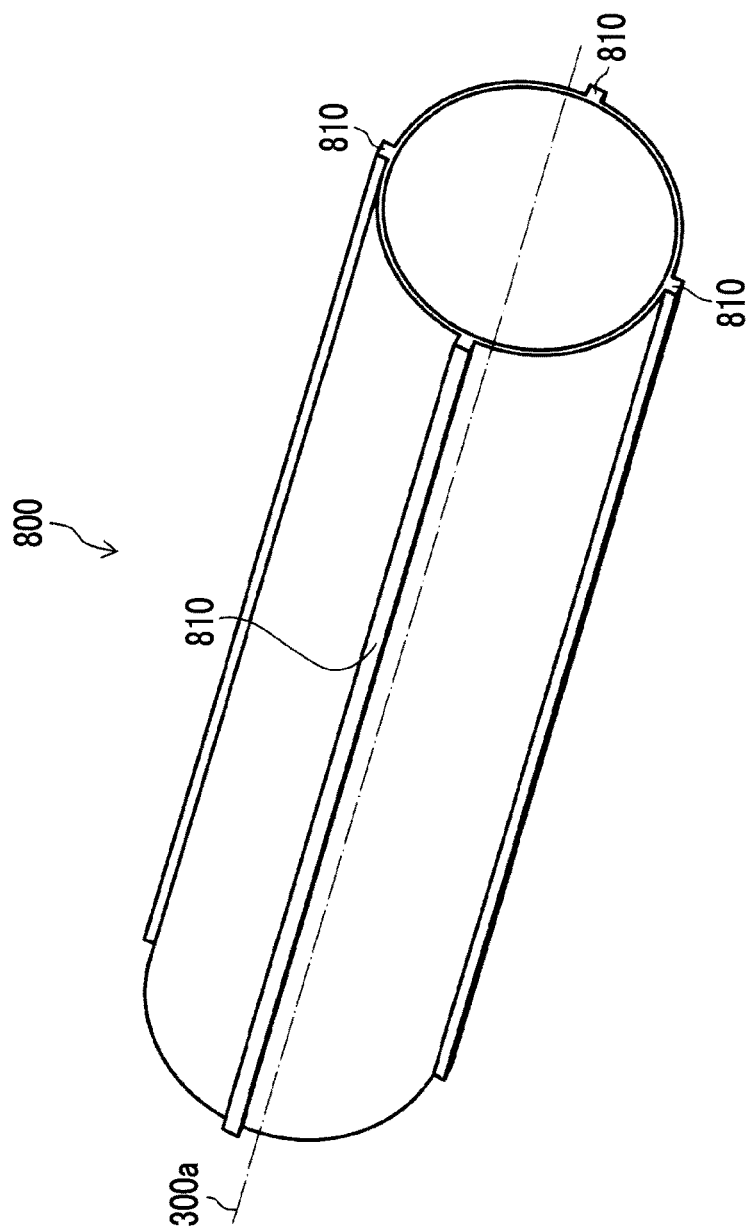
FIG. 26 is a perspective view illustrating the form of the wall surface member provided with the protrusions only in the longitudinal direction.
Figure 27:
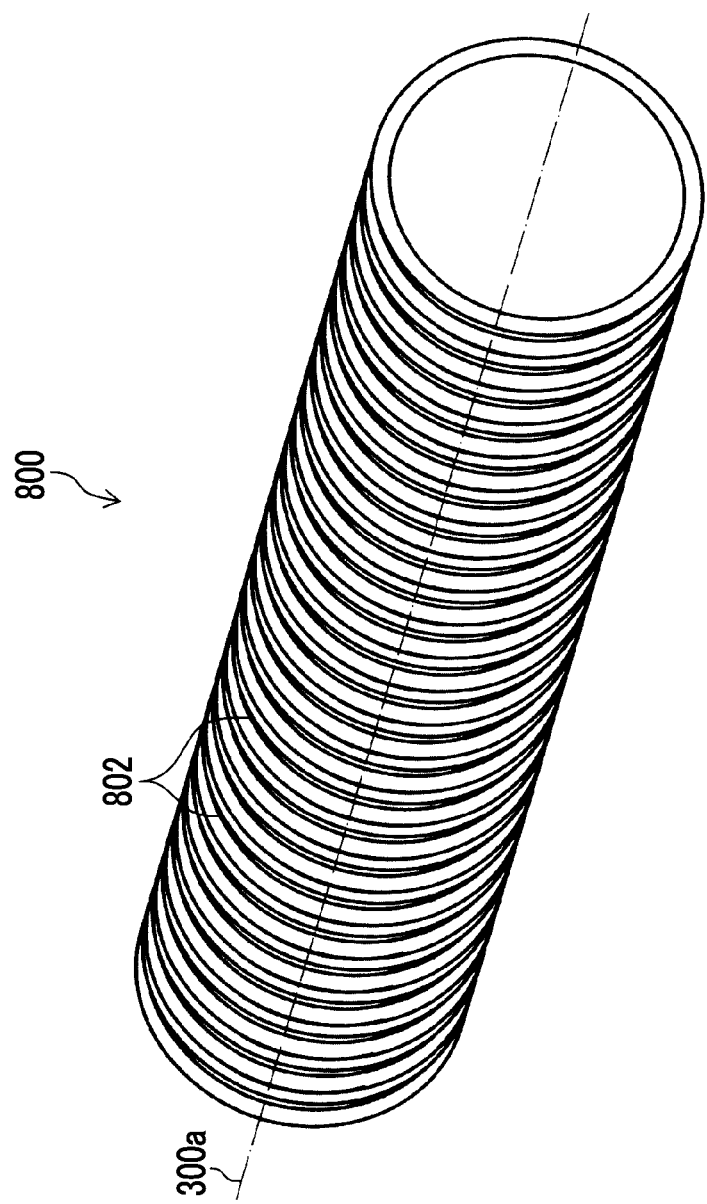
FIG. 27 is a perspective view illustrating the form of the wall surface member provided with grooves (protrusions) only in a transverse direction.

Additionally, although the wall surface member 800 of the above embodiment has a form in which both of the first concavo-convex parts and the second concavo-convex parts are included, as illustrated in FIGS. 25 to 27, a form in which only any one is included and the rotation around the axis and the forward and backward movement in the axial direction is prevented may be adopted.

FIG. 25 illustrates the wall surface member 800 including only the first concavo-convex parts, and four longitudinal grooves 804 are included at equal intervals in the direction (circumferential direction) around the axis at the outer peripheral part of the wall surface member 800. Accordingly, the unintended rotation of the overtube 300 around the axis is prevented.

FIG. 26 illustrates the wall surface member 800 including only the first concavo-convex parts, and four protrusions 810 are included at equal intervals in the direction (circumferential direction) around the axis at the outer peripheral part of the wall surface member 800. Accordingly, the unintended rotation of the overtube 300 around the axis is prevented.

FIG. 27 illustrates the wall surface member 800 including only the second concavo-convex parts, and a number of transverse grooves 802 are included at the outer peripheral part of the wall surface member 800. Accordingly, the unintended forward and backward movement of the overtube 300 in the axial direction is prevented.

Additionally, in the wall surface member 800 of the forms illustrated in FIGS. 21 to 26, the unintended forward and backward movement of the overtube 300 in the axial direction easily takes place if the number of longitudinal grooves 804 or protrusions 810 is increased. Therefore, the number of longitudinal grooves 804 or protrusions 810 is set to only four. Therefore, when the wall surface member 800 and a body wall do not come into contact with each other with uniform pressure over the whole circumference, contact pressure with the body wall becomes weak in all portions where the longitudinal grooves 804 or the protrusions 810 are provided, and a situation where the unintended rotation of the overtube 300 easily takes place may occur.

Thus, the wall surface member 800 may be divided into regions having a shorter length than the thickness of a body wall in the direction of the reference axis 300a, and the position of the longitudinal groove 804 or the protrusion 810 in each region in the direction around the axis may be shifted by a predetermined angle from the adjacent region.

Figure 28:
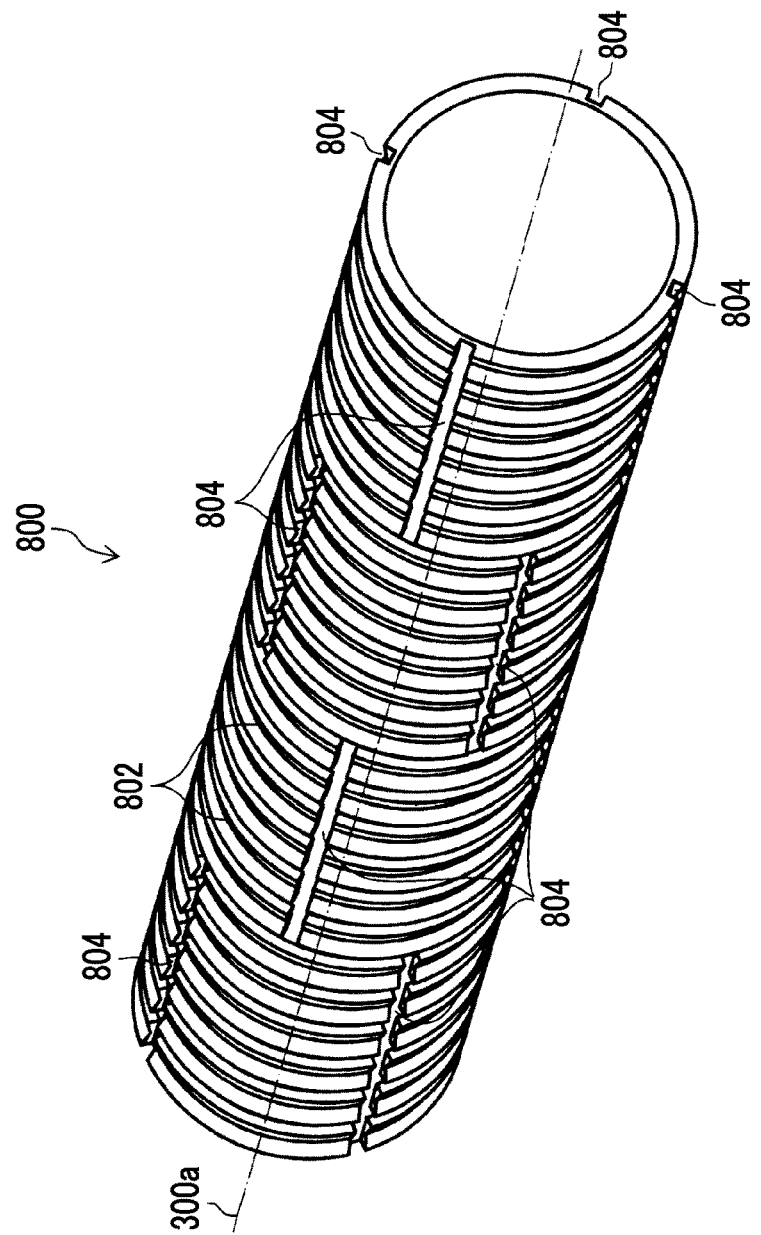
FIG. 28 is a perspective view illustrating a modification example of the wall surface member of FIG. 22.

FIG. 28 illustrates a form in which the wall surface member 800 is divided into four regions in the direction of the reference axis 300a, and the position of the longitudinal groove 804 in each region in the direction around the axis is shifted from the adjacent region by 45 degrees, in the form illustrated in FIG. 22.

According to this, at least two regions of the wall surface member 800 come into contact with a body wall in a state where the overtube 300 is inserted into the body wall. Therefore, even when the contact pressure of the body wall with the wall surface member 800 is not uniform as described above, a situation where the contact pressure becomes weak in the portions of the longitudinal grooves 804 in all the regions that come into contact with the body wall is reduced, and the rotation of the overtube 300 around the axis is appropriately prevented.

In addition, the form illustrated in FIG. 28 can also be similarly applied in the forms illustrated in FIGS. 24 to 26.

Additionally, in the wall surface members 800 of the forms illustrated in FIGS. 21 to 24, FIG. 27, and FIG. 28, the second concavo-convex parts that prevent the forward and backward movement in the axial direction with respect to a body wall are not limited to the form as illustrated in the section of FIG. 23.

Figure 29:
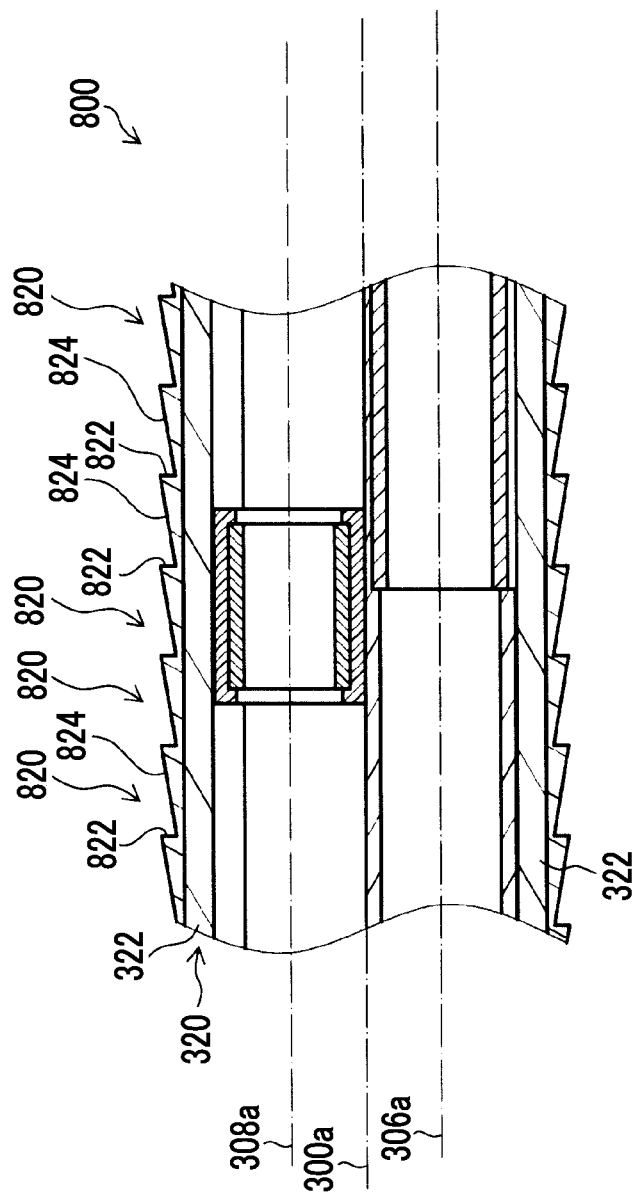
FIG. 29 is a sectional view illustrating another form of a second concavo-convex part of the wall surface member of FIG. 22.

FIG. 29 is a sectional view illustrating another form of the second concavo-convex parts. The second concavo-convex parts in this drawing consist of annular transverse grooves 820 along the circumferential direction in the outer peripheral part of the wall surface member 800. By continuously forming the transverse grooves 820 in the direction (axial direction) of the reference axis 300a, a plurality of second concavo-convex parts are periodically provided in the axial direction.

The transverse groove 820 is formed by a side surface 822, and a tapered surface 824 located on a base end side (rear side) with respect to the side surface 822.

The side surface 822 is a surface along a plane perpendicular to the reference axis 300a, and the tapered surface 824 is a tapered surface of which the diameter gradually becomes smaller from the base end side toward the distal end side (front side). The transverse grooves 820 adjacent to each other in the axial direction are connected at the position of a base end of the tapered surface 824 of the transverse groove 820 on the distal end side, and the position of an outer edge end of the side surface 822 of the transverse groove 820 on the base end side.

According to the second concavo-convex parts of the present form, a portion of a body wall enters the transverse grooves 820 in a state where the overtube 300 is inserted into the body wall. Therefore, the side surface 822 acts as the second locking surface that restricts the movement of the overtube 300 to the base end side in the axial direction, similar to the action of the second side surface 807b of the form of FIG. 23. That is, with respect to the movement of the overtube 300 in a slip-out direction, the side surface 822 is reversed, and the overtube 300 does not easily slip out from a body wall.

Meanwhile, the tapered surface 824 acts as the first locking surface that restricts the movement of the overtube 300 to the distal end side in the axial direction. Additionally, the tapered surface 824 enables smooth forward movement when the overtube 300 is inserted into a body wall. That is, the overtube 300 can be inserted into a body wall without crushing tissue.

As described above, in the above embodiment, various concavo-convex parts are formed in the outer peripheral part by the wall surface member 800 separate from the overtube 300. However, the above concavo-convex parts may be directly formed at the outer peripheral part of the overtube body 320.

Additionally, in the above embodiment, the transverse grooves 802, the longitudinal grooves 804, protrusions 810, or the like is provided at equal intervals in the direction around the axis, and the concavo-convex parts are periodically provided. However, these are not necessarily provided at equal intervals, and the concavo-convex parts may be periodically provided.

Additionally, in the above embodiment, the plurality of transverse grooves 802 illustrated in FIGS. 21 to 24, FIG. 27, and FIG. 28 and the plurality of transverse grooves 820 illustrated in FIG. 29 are provided in the axial direction. However, transverse grooves with the same sectional shape as that of the transverse grooves 802 and 820 may be spirally provided at the outer peripheral part of the overtube body 320.

(Outer Port Including Wall Surface Member)

Next, an outer port (exterior tube) including the above-described wall surface member 800 will be described. Although the above-described wall surface member 800 has a form in which the wall surface member is fitted on the outer surface of the overtube body 320 and fixed to a predetermined position, the outer port 830 to be described below can also have a form including a component equivalent to the wall surface member 800.

Figure 30:
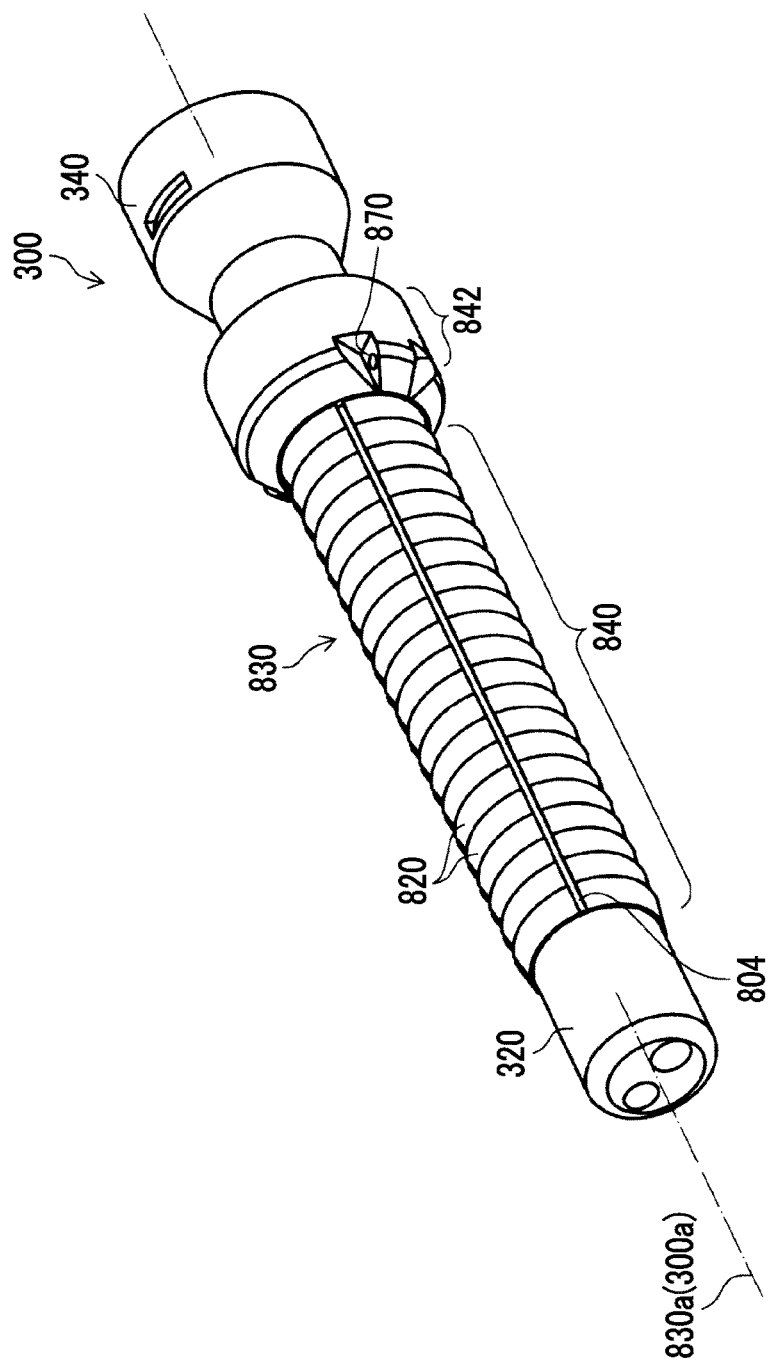
FIG. 30 is an appearance view illustrating an outer port through which the overtube is inserted, from the front upper left.
Figure 31:
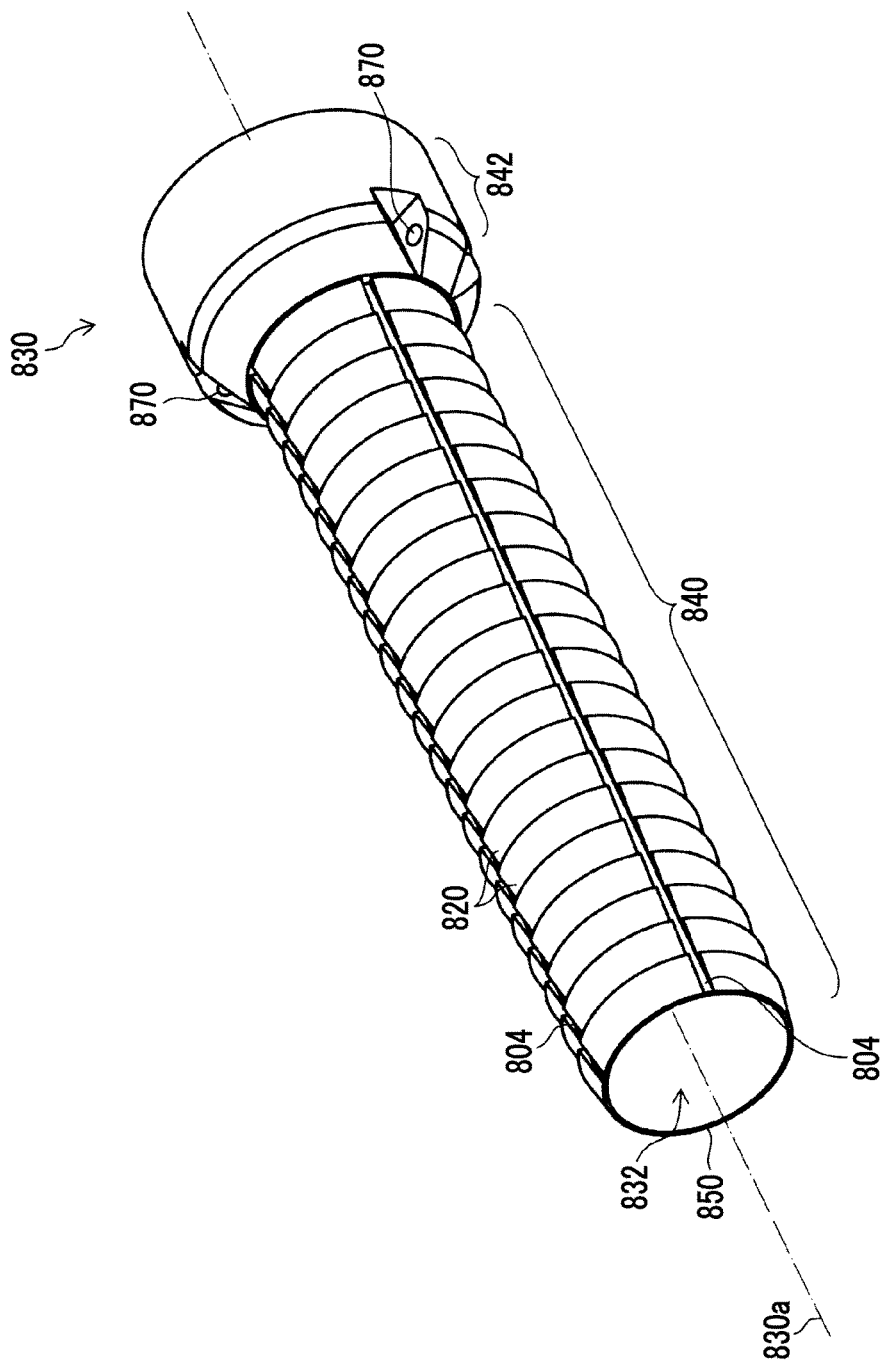
FIG. 31 is a perspective view illustrating only an outer port 830 from the diagonal front.
Figure 32:
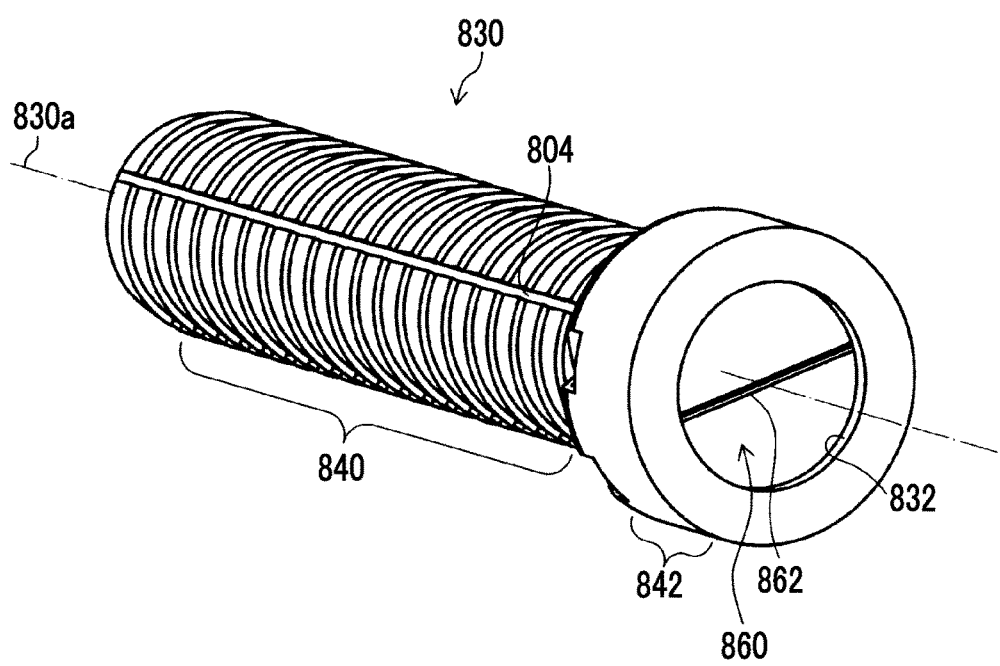
FIG. 32 is an appearance view illustrating only the outer port 830 from the diagonal rear.

FIG. 30 is an appearance view illustrating an outer port 830 through which the overtube 300 is inserted, from the front upper left. FIG. 31 is a perspective view illustrating only the outer port 830 from the diagonal front, and FIG. 32 is an appearance view illustrating only the outer port 830 from the diagonal rear.

As illustrated in these drawings, the outer port 830 that is an exterior tube is formed in a long tubular shape having the reference axis 830a as a central axis using plastic or the like, and has an insertion hole 832 that penetrates along the direction (axial direction) of the reference axis 830a from a base end of the outer port 830 to a distal end thereof.

The insertion hole 832 has a diameter of such a size that the overtube body 320 can move forward and backward in the axial direction and is inserted therethrough so as to be rotatable in the direction around the axis.

If the overtube body 320 is inserted into the insertion hole 832 from the base end side and is moved forward, the overtube body 320 is led out from the distal end side of the insertion hole 832. Accordingly, as illustrated in FIG. 30, the outer port 830 is set in a state where the outer port 830 has been fitted on the outer side of the overtube body 320.

In addition, the axial length of the outer port 830 is shorter than the axial length (the length of a portion closer to the distal end side than the front end of the base end cap 340 of the overtube 300) of the overtube body 320, and the outer port 830 falls within the axial range of the overtube body 320.

Additionally, the outer port 830 is constituted of an insertion part 840 on the distal end side, and a base end part 842 connected to the base end side from a base end of the insertion part 840.

The insertion part 840 is a portion that is inserted into a body wall together with the overtube body 320 inserted through the insertion hole 832 and is inserted into holes (ports) of the body wall and a body cavity, and has an outer wall 850 having a long tubular shape with substantially the same external diameter and internal diameter from the base end to the distal end with the reference axis 830a as a central axis. The lumen inside the outer wall 850 becomes a portion of the above-described insertion hole 832, and has substantially the same diameter as the external diameter of the overtube body 320.

Therefore, as illustrated in FIG. 30, an inner peripheral surface of the outer wall 850 in the insertion part 840 of the outer port 830 contacts or approaches the outer peripheral surface of the overtube body 320 without a substantial gap, in a state where the overtube body 320 is inserted through the insertion hole 832 of the outer port 830. Additionally, the position of the reference axis 830a of the outer port 830 and the position of the reference axis 300a of the overtube 300 substantially coincide with each other.

In addition, the axial length of the insertion part 840 is longer than the thickness of a body wall (abdominal wall or the like) in a region where the overtube 300 and the outer port 830 are inserted. It is suitable that the length of the insertion part 840 when being inserted into a human being's abdominal wall is about 75 mm.

Additionally, the insertion part 840 is a portion equivalent to the above-described wall surface member 800, and the first concavo-convex parts that prevent the forward and backward movement in the axial direction with respect to a body wall and the second concavo-convex parts that prevent the rotation in the direction around the axis with respect to a body wall are formed at the outer peripheral part of the outer wall 850, similar to the outer peripheral part of the wall surface member 800.

The first concavo-convex parts are configured similar to the first concavo-convex parts consisting of the longitudinal grooves 804 illustrated in FIGS. 21 and 22, and have longitudinal grooves (designated by the same reference sign 804) of the same form as the longitudinal grooves 804 of FIGS. 21 and 22. By providing the longitudinal grooves 804 at the positions of four places at intervals of 90 degrees in the direction around the axis, the plurality of first concavo-convex parts are periodically provided in the direction around the axis.

In addition, it is desirable that the intervals of the longitudinal grooves 804 in the direction around the axis are equal to or larger than 10 degrees and equal to or smaller than 120 degrees.

Additionally, it is desirable that the depth of the longitudinal grooves 804 is equal to or larger than 0.3 mm and equal to or smaller than 3.0 mm.

The second concavo-convex parts are configured similar to the second concavo-convex parts consisting of the transverse grooves 820 illustrated in FIG. 29 and have transverse grooves (designated by the same reference sign 820) of the same form as the transverse grooves 820 of FIG. 29. The plurality of transverse grooves 820 are periodically provided in the axial direction.

Each transverse groove 820, similar to the transverse groove 820 illustrated in FIG. 29, has the tapered surface 824 (base-end-side wall surface) that acts as the first locking surface that restricts the movement of the outer port 830 to the distal end side in the axial direction with respect to a body wall, and the side surface 822 (distal end-side wall surface) that acts as the second locking surface that restricts the movement of the outer port 830 to the base end side in the axial direction with respect to a body wall.

The unintended forward and backward movement of the outer port 830 in the axial direction with respect to a body wall and the rotation thereof in the direction around the axis are prevented by the first concavo-convex parts and the second concavo-convex parts (the details thereof will be described below).

In addition, it is desirable that the pitch of the transverse grooves 820 is equal to or larger than 1.0 mm and equal to or smaller than 5 mm, and it is desirable that the maximum depth of the transverse grooves 820 is equal to or larger than 0.3 mm and equal to or smaller than 2.0 mm.

The inclination angle (the inclination angle of the outer port 830 with respect to the radial direction perpendicular to the reference axis 830a) of the side surface 822 is made smaller than the inclination angle (the inclination angle of the outer port 830 with respect to the reference axis 830a perpendicular to the radial direction) of the tapered surface 824.

In the present form, the side surface 822 is formed parallel to the radial direction perpendicular to the reference axis 830a of the outer port 830. In other words, the normal direction of the side surface 822 is formed parallel to the reference axis 830a of the outer port 830. In addition, the side surface 822 may not necessarily be parallel to the radial direction perpendicular to the reference axis 830a of the outer port 830, for example, the inclination angle of the side surface 822 may be within a range of equal to or larger than 0 degrees and equal to or smaller than 30 degrees, and preferably equal to or larger than 0 degrees and equal to or smaller than 15 degrees on the distal end side or on the base end side.

Additionally, the inclination angle of the tapered surface 824 may be larger than the inclination angle of the side surface 822, for example, may be within a range of equal to or larger than 45 degrees and smaller than 90 degrees, and preferably equal to or larger than 60 degrees and smaller than 90 degrees on the base end side with respect to the radial direction perpendicular to the reference axis 830a of the outer port 830.

The base end part 842 of the outer port 830 has a larger external diameter than that of the insertion part 840. Accordingly, the base end part 842 is not inserted into holes (ports) of a body wall into which the insertion part 840 is inserted, and is a portion arranged outside of the body. In addition, the base end part 842 may be formed integrally with the insertion part 840, or may be formed separately from the insertion part 840 and may be fixed to the insertion part 840 by arbitrary fixing means.

Additionally, the base end part 842, as illustrated in FIG. 32, has an airtight valve (valve member) 860. A portion of the above-described insertion hole 832 that communicates with the insertion part 840 is formed at the base end part 842, and an airtight valve 860 is arranged at a position near a base-end-side opening of the insertion hole 832.

The airtight valve 860 has a slit (cut-in) 862 that opens only when the overtube body 320 is inserted into the insertion hole 832 and that comes into close contact with the outer peripheral surface of the overtube body 320 without a substantial gap. Accordingly, the airtightness of a space (the inside of a body cavity) that communicates with the insertion hole 832 closer to the distal end side than the airtight valve 860 even in any of a state where the overtube body 320 is inserted through the insertion hole 832 and a state where the overtube body 320 has been extracted from the insertion hole 832 is secured. In addition, the slit 862 provided in the airtight valve 860 may be one straight line or may be two straight lines orthogonal to each other. Additionally, as long as the configuration of the airtight valve 860 can maintain the same airtightness as the present form, any kind of form may be adopted.

Additionally, the airtight valve 860 fixes the overtube body 320 with a given fixing force due to a frictional force that acts between the insertion hole 832 and the overtube body 320 when the overtube body 320 is inserted through the insertion hole 832. Accordingly, the outer port 830 is connected (mounted) integrally with the overtube 300.

That is, the relative positional relationship between the outer port 830 and the overtube 300 does not change unless a surgeon applies force for relatively moving the outer port 830 and the overtube 300 with respect to both of them.

Moreover, holes 870 for allowing thread for fixing the outer port 830 and a body wall to pass therethrough are provided in two places in the base end part 842. The outer port 830 can be fixed to a body wall by passing thread through the holes 870, and piercing one end part of the thread through the body wall to connect the one end part to the other end part.

The action of the outer port 830 configured as above will be described. A surgeon grips the outer port 830 and the overtube 300 before the overtube 300 is inserted into a body wall, and inserts the overtube 300 (overtube body 320) through the insertion hole 832 of the outer port 830. Then, the axial position of the overtube 300 with respect to the outer port 830 and the rotational position thereof in the direction around the axis are adjusted. In this case, the fixing force (frictional force) of the airtight valve 860 of the outer port 830 acts on the overtube 300, and the outer port 830 is fixed (mounted) to the overtube 300 in a stable state at an adjustment position thereof.

Figure 33:
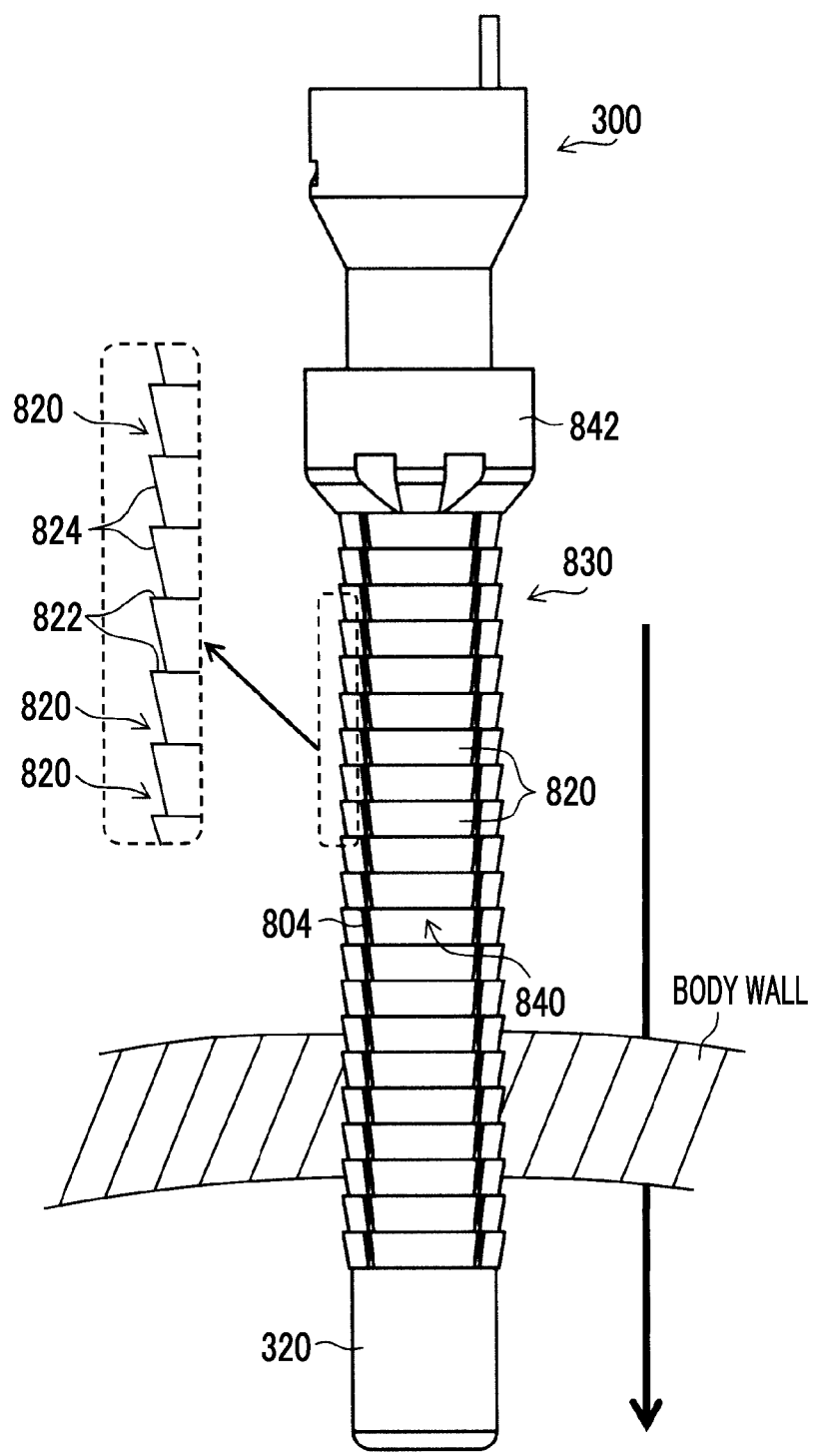
FIG. 33 is an explanatory view used for the description of the action of the outer port.

After the outer port 830 is mounted on the overtube 300, a surgeon inserts the outer port 830 as illustrated in FIG. 33 from holes (ports) of the body wall together with the overtube 300. That is, the overtube 300 and the outer port 830 are moved forward to the distal end side (insertion direction) in the axial direction.

In that case, a resistance force is received by the second concavo-convex parts consisting of the transverse grooves 820 formed at the insertion part 840 (outer wall 850) of the outer port 830.

However, since the first locking surface that restricts the movement of the outer port 830 to the distal end side in the axial direction is the tapered surface 824 of the transverse groove 820, and the inclination angle (the inclination angle of the tapered surface 824 with respect to the radial direction perpendicular to the reference axis 830a) of the tapered surface 824 is large as described above, the action that restricts the movement to the distal end side in the axial direction is weak. Therefore, the overtube 300 and the outer port 830 can be smoothly inserted into holes (ports) of a body wall. Additionally, a situation where the second concavo-convex parts crush the tissue of a body wall at the time of insertion does not occur.

As described above, after the overtube 300 and the outer port 830 have been inserted into a body wall and inserted to predetermined positions within a body cavity, a surgeon inserts the endoscope 100 and the treatment tool 200 through the overtube 300, and performs operation or the like of the treatment tool 200.

In that case, the operation or the like of the treatment tool 200 is accompanied with the outer port 830, and an unintended force is applied to the outer port 830 via the overtube 300 in the direction around the axis or the axial direction.

However, the first concavo-convex parts consisting of the longitudinal grooves 804 formed at the insertion part 840 (outer wall 850) of the outer port 830 restrict the movement of the outer port 830 in the direction around the axis. Therefore, the unintended rotation of the outer port 830 and the overtube 300 in the direction around the axis is prevented.

Additionally, the side surface 822 of the transverse groove 820 that acts as the second locking surface in the second concavo-convex part consisting of the transverse groove 820 formed at the insertion part 840 (outer wall 850) of the outer port 830 restricts the movement of the outer port 830 to the base end side in the axial direction. Therefore, the unintended backward movement of the outer port 830 and the overtube 300 to the base end side in the axial direction is prevented.

Meanwhile, the tapered surface 824 of the transverse groove 820 that acts as the first locking surface in the second concavo-convex part consisting of the transverse groove 820 formed at the insertion part 840 (outer wall 850) of the outer port 830 restricts the movement of the outer port 830 to the distal end side in the axial direction. However, since the action of the restriction is weak as described above, there is a concern that the unintended forward movement of the outer port 830 and the overtube 300 to the distal end side in the axial direction may occur.

Figure 34:
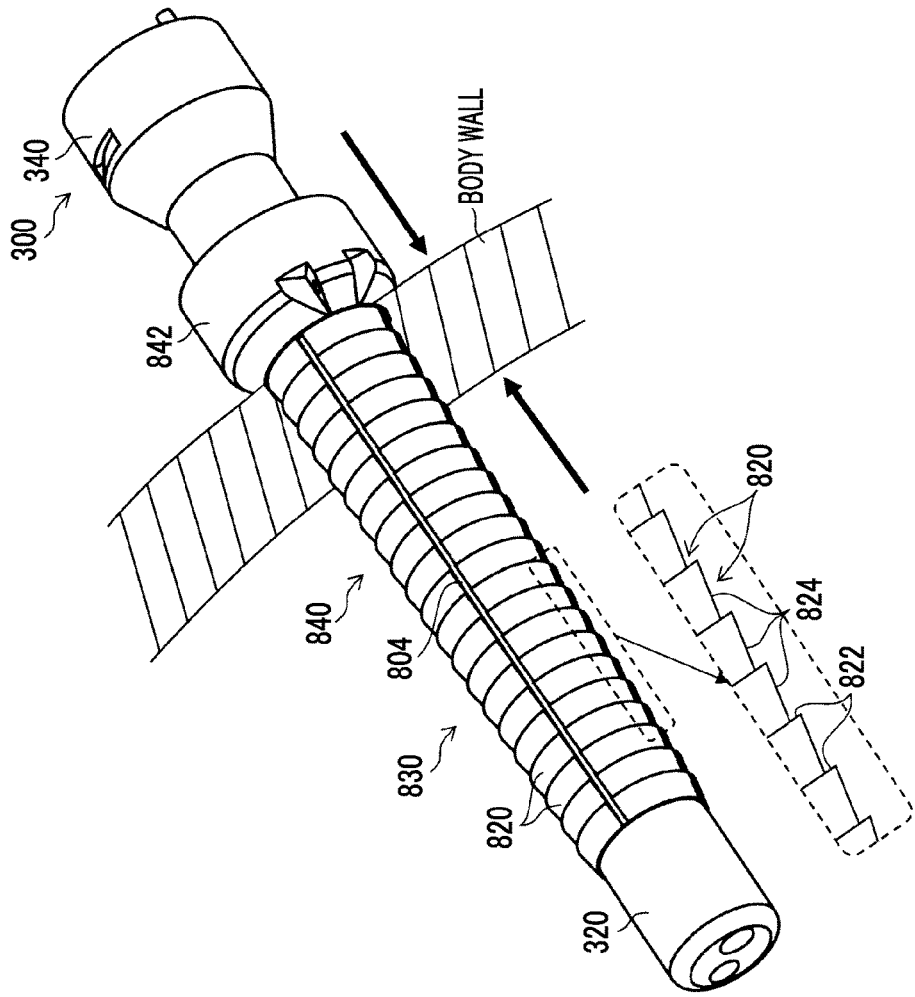
FIG. 34 is an explanatory view used for the description of the action of the outer port.

Thus, in order to prevent such a situation beforehand, setting to a state where the outer port 830 is inserted into a body cavity up to a position where the base end part 842 of the outer port 830 comes into contact with a body wall surface (body wall tissue) as illustrated in FIG. 34 is made, and the operation of the endoscope 100 and the treatment tool 200 is performed.

Accordingly, the base end part 842 serves as a stopper, and the unintended forward movement of the outer port 830 and the overtube 300 to the distal end side in the axial direction is reliably prevented. However, the invention is not necessarily limited to being used after being set to such a state.

Additionally, if necessary, the outer port 830 can also be fixed to the body wall with thread, using the holes 870 provided in the base end part 842 of the outer port 830.

In addition, when the rotation of the overtube 300 in the direction around the axis with respect to a body wall and the axial position of the overtube 300 are adjusted, it is not necessary to move the outer port 830 with respect to the body wall, and the overtube 300 only has to be moved with respect to the outer port 830 in a state where the outer port 830 is fixed to the body wall.

As described above, forms of arbitrary concavo-convex parts applicable to the wall surface members 800 illustrated in FIGS. 21 to 28 and the like can be applied as the forms of the concavo-convex parts formed at the outer peripheral part of the insertion part 840 of the outer port 830.

<Operation Method of Endoscopic Surgical Device>

Next, an example of operation methods using the endoscopic surgical device 10 of the present embodiment will be described.

FIGS. 35A to 39B are explanatory views illustrating a situation in which the endoscopic surgical device 10 of the present embodiment is operated.

FIGS. 35A to 35C are views illustrating a situation in which the overtube 300 is inserted into a body wall.

FIGS. 36A to 37B are views illustrating a situation in which the treatment tool insertion part 202 is pushed into an affected part side within a body cavity from the hand side.

FIGS. 38A to 39B are views illustrating a situation in which the treatment tool insertion part 202 is pulled to the hand side from the affected part side within the body cavity.

First, as a preparation step for starting the operation of the endoscopic surgical device 10, the overtube 300 is inserted into a skin-incised part (incised wound) formed in a body wall in a state where the inner needle 500 has been mounted on the overtube 300, and the overtube 300 is inserted into the body cavity like a state designated by reference sign 1000 of FIG. 35A. In addition, description will be omitted about a case where the outer port 830 illustrated in FIG. 30 and the like is used.

Next, the inner needle 500 is extracted from the endoscope insertion passage 306 and the treatment tool insertion passage 308 (the inner needle 500 is removed from the overtube 300), and one end part of the air supply tube 122 is connected to the air supply connector 318 of the overtube 300 like a state designated by reference sign 1002 of FIG. 35B. The other end part is connected to the pneumoperitoneum device 120. Then, pneumoperitoneum gas is delivered from the pneumoperitoneum device 120, and the pneumoperitoneum gas is injected into the body cavity through the air supply tube 122 and the overtube 300.

Next, the endoscope insertion part 102 is inserted into the endoscope insertion passage 306 from the endoscope insertion opening 310 of the overtube 300, and the distal end of the endoscope insertion part 102 is led out from the endoscope delivery opening 312.

In this case, the endoscope insertion part 102 has the endoscope-coupled part 420 of the slider 400 inserted therethrough, and is coupled to the slider body 402 as described above. Accordingly, the endoscope insertion part 102 and the slider 400 are brought into a state where they move integrally.

Subsequently, the treatment tool insertion part 202 is inserted into the treatment tool insertion passage 308 from the treatment tool insertion opening 314 of the overtube 300, and the distal end (treatment part 206) of the treatment tool insertion part 202 is led out from the treatment tool delivery opening 316.

In this case, the treatment tool insertion part 202 has the sleeve 440 of the treatment tool-coupled part 422 of the slider 400 inserted therethrough, and is coupled to the sleeve 440 as described above. Accordingly, the treatment tool insertion part 202 and the sleeve 440 are brought into a state where they move integrally.

If the preparation step is performed in this way, a state where the operation of the endoscopic surgical device 10 is operable is brought about like a state designated by reference sign 1004 of FIG. 35C.

In addition, the distal end position of the endoscope insertion part 102 is arranged behind at least the distal end position of the treatment tool insertion part 202 so that the situation of the treatment part 206 at the distal end of the treatment tool insertion part 202 can be observed by the endoscope 100. Additionally, the procedure of inserting the endoscope insertion part 102 and the treatment tool insertion part 202 into the overtube 300 is not limited to the above-described order, and the endoscope insertion part 102 may be inserted after the treatment tool insertion part 202 is inserted.

Next, a case where the treatment tool insertion part 202 is pushed into the affected part side within the body cavity from the hand side (a case where the treatment tool insertion part moves forward) will be described with reference to FIGS. 36A to 37B.

First, when the treatment tool insertion part 202 has been minutely displaced in the axial direction like a state designated by reference sign 1008 of FIG. 36B from a state designated by reference sign 1006 of FIG. 36A (when a forward and backward movement of a small amplitude has been performed), only the treatment tool insertion part 202 moves forward and backward, and the slider 400 does not move forward and backward. Therefore, since the endoscope insertion part 102 does not move forward and backward, the range of an observation image displayed on the monitor 112 does not change. For this reason, the size of an object to be observed can be prevented from fluctuating according to the minute displacement of the treatment tool insertion part 202, a sense of perspective can be suitably maintained, and a stable observation image can be obtained.

Figures 37A, 37B:
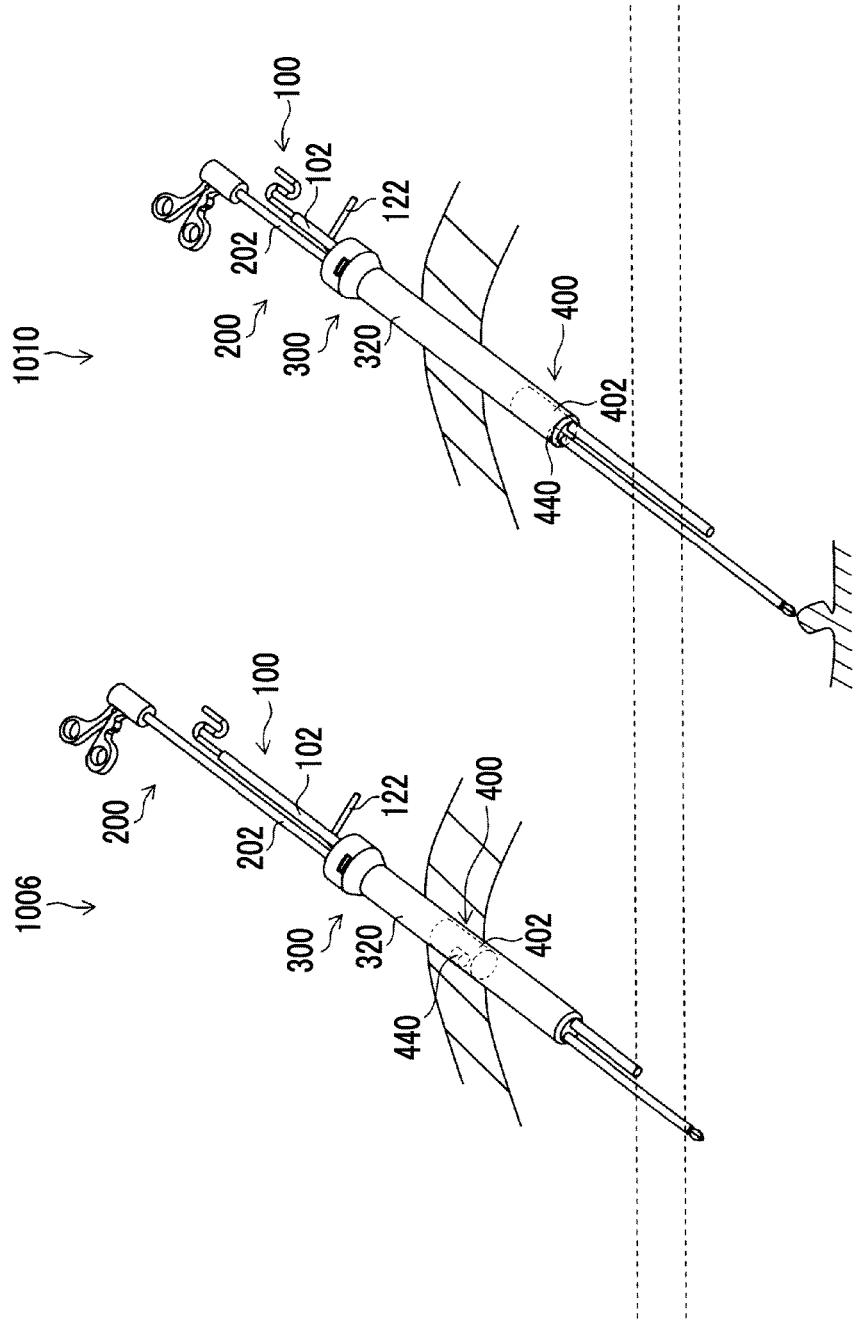
FIGS. 37A and 37B are views illustrating a situation in which the treatment tool insertion part is pushed into the affected part side within the body cavity from the hand side.

In contrast, when the treatment tool insertion part 202 has been largely displaced in the axial direction like a state designated by reference sign 1010 of FIG. 37B from a state designated by reference sign 1006 of FIG. 37A that is the same state as reference sign 1006 of FIG. 36A (when a forward and backward movement of a large amplitude has been performed), the slider 400 moves forward and backward in an interlocking manner with the forward and backward movement of the treatment tool insertion part 202. In this case, since the endoscope insertion part 102 moves forward and backward, the range of an observation image displayed on the monitor 112 is continuously changed so as to follow the forward and backward movement of the treatment tool insertion part 202. Accordingly, since the size of an object to be observed changes according to the operation of the treatment tool 200, it is possible to simply obtain an image desired by a surgeon.

Additionally, the same applies to a case where the treatment tool insertion part 202 is pulled to the hand side from the affected part side within the body cavity (when the treatment tool insertion part moves backward).

That is, when the treatment tool insertion part 202 has been minutely displaced in the axial direction like a state designated by reference sign 1014 of FIG. 38B from a state designated by reference sign 1012 of FIG. 38A (when a forward and backward movement of a small amplitude has been performed), only the treatment tool insertion part 202 moves forward and backward, and the slider 400 does not move forward and backward. Therefore, since the endoscope insertion part 102 does not move forward and backward, the range of an observation image displayed on the monitor 112 does not change. For this reason, the size of an object to be observed can be prevented from fluctuating according to the minute displacement of the treatment tool insertion part 202, a sense of perspective can be suitably maintained, and a stable observation image can be obtained.

Figure 39A:
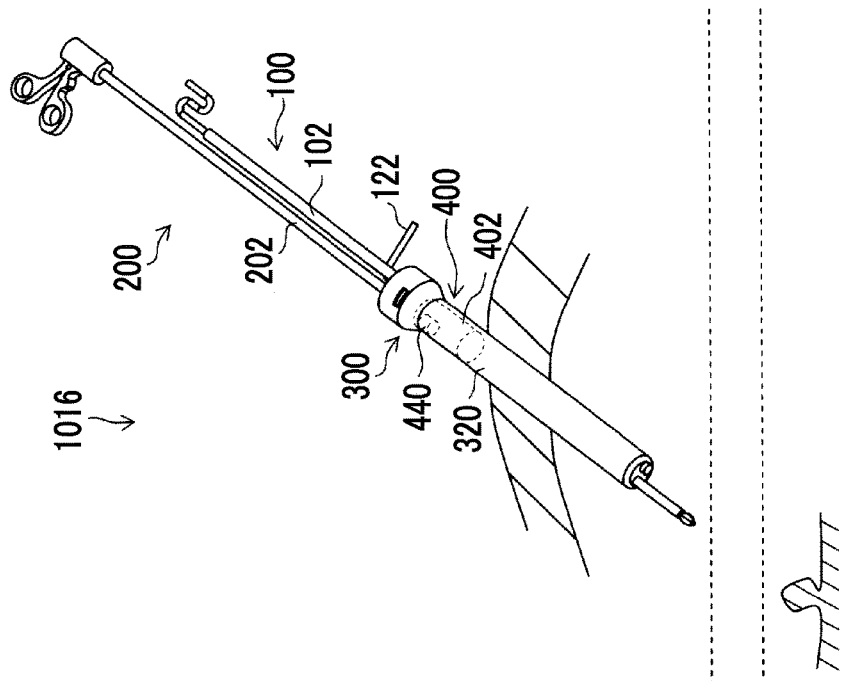
FIGS. 39A and 39B are views illustrating a situation in which the treatment tool insertion part is pulled to the hand side from the affected part side within the body cavity.
Figure 39B:
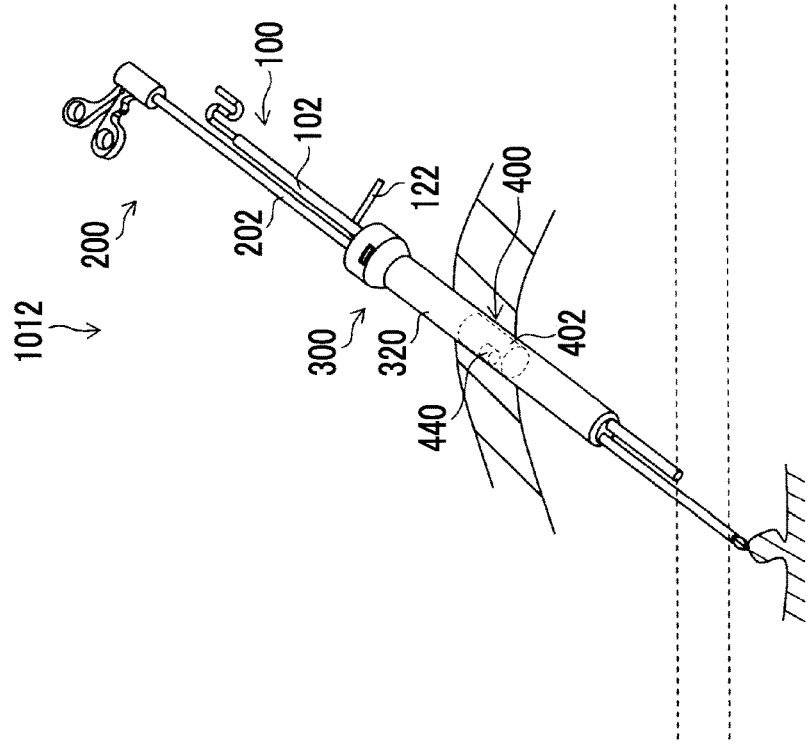

In contrast, when the treatment tool insertion part 202 has been largely displaced in the axial direction like a state designated by reference sign 1016 of FIG. 39B from a state designated by reference sign 1012 of FIG. 39A that is the same state as reference sign 1012 of FIG. 38A (when a forward and backward movement of a large amplitude has been performed), the slider 400 moves forward and backward in an interlocking manner with the forward and backward movement of the treatment tool insertion part 202. In this case, since the endoscope insertion part 102 moves forward and backward, the range of an observation image displayed on the monitor 112 is continuously changed so as to follow the forward and backward movement of the treatment tool insertion part 202. Accordingly, since the size of an object to be observed changes according to the operation of the treatment tool 200, it is possible to simply obtain an image desired by a surgeon.

<Endoscopic Surgery>

Next, an example of endoscopic surgery using the endoscopic surgical device 10 of the present embodiment will be described.

(Laparoscopic Hernia Reparative Surgery)

Next, laparoscopic hernia reparative surgery will be described as a first example of the endoscopic surgery.

In the laparoscopic hernia reparative surgery using the endoscopic surgical device 10 of the present embodiment, holes (ports) for allowing an endoscope and a treatment tool to be inserted into an abdominal cavity therethrough are formed in two places in a patient's abdomen. That is, in the present embodiment, the endoscope (equivalent to the above endoscope 100) and the treatment tool (equivalent to the above treatment tool 200) are inserted into a body cavity via an overtube (a first trocar equivalent to the above overtube 300) from the same port. Therefore, the number of ports is smaller by one compared to related-art multi-port (multi-hole type) laparoscopic hernia reparative surgery.

Figure 40:
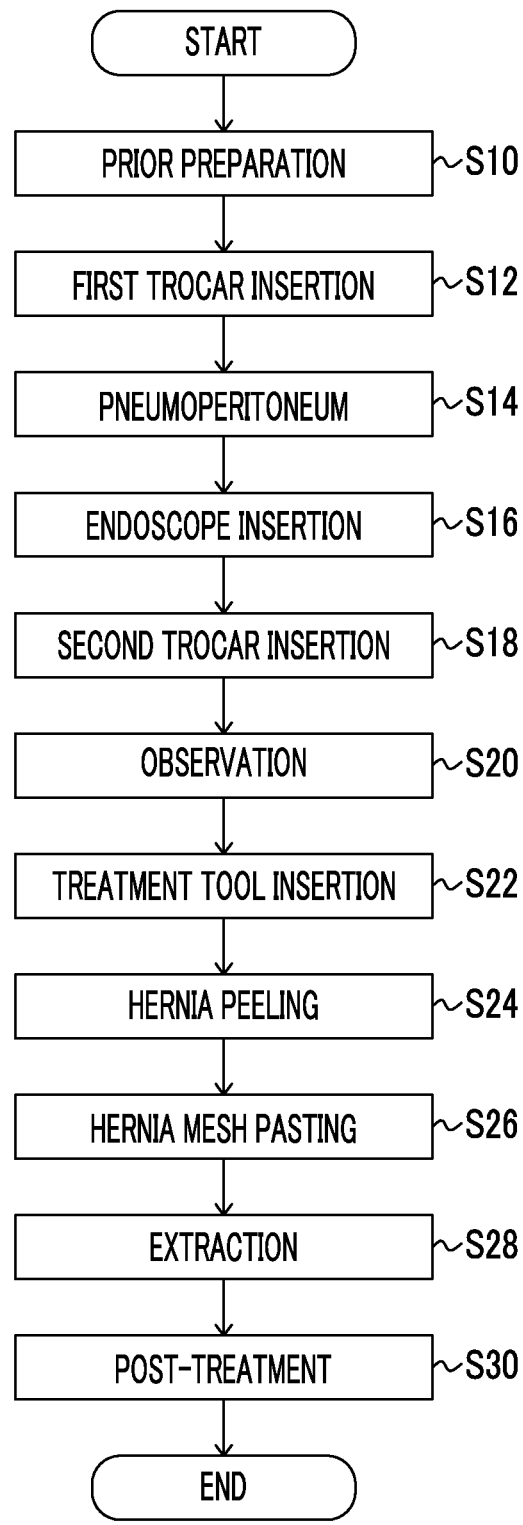
FIG. 40 is a view illustrating a procedure of laparoscopic hernia reparative surgery.

Next, a procedure of the laparoscopic hernia reparative surgery will be described. FIG. 40 is a view illustrating the procedure of the laparoscopic hernia reparative surgery. Hereinafter, respective steps of the invention will be described referring to FIG. 40.

[First Trocar Insertion Step]

First, after predetermined prior preparation has been performed (Step S10) a first trocar insertion step is performed (Step S12). In the first trocar insertion step, after a surgeon has incised a patient's abdominal wall surface, the surgeon and an assistant dilate the skin-incised part up to the peritoneum. Thereafter, the surgeon and the assistant integrally insert the first trocar and an outer port (equivalent to the above outer port 830) into the skin-incised part. The outer port has an internal diameter such that the first trocar can be inserted thereinto, and is inserted into the skin-incised part in a state where the first trocar is inserted into the outer port. Hereinbelow, a case where the first trocar and the outer port are integrated may simply be referred to as the first trocar. In addition, when the first trocar is inserted into an abdominal cavity, this insertion is performed in a state where an inner needle (equivalent to the above inner needle 500) is inserted through the inside of the first trocar. Then, after the insertion of the first trocar, the inner needle is extracted from the first trocar. Accordingly, at the time of the insertion of the first trocar, the tissue of an abdominal wall can be prevented from invading the inside of the first trocar. Moreover, the position (the forward and backward movement direction or the rotational direction) of the first trocar with respect to the outer port is appropriately adjusted. Additionally, when the outer port inserted into the patient's abdominal cavity is likely to move, the surgeon and the assistant fix the outer port to the abdominal wall with thread if necessary.

[Pneumoperitoneum Step]

Next, a pneumoperitoneum step is performed (Step S14). In a pneumoperitoneum step, first, a pneumoperitoneum tube (equivalent to the above air supply tube 122) is connected to the first trocar. Next, a pneumoperitoneum device (equivalent to the above pneumoperitoneum device 120) is mounted on the pneumoperitoneum tube, and the pneumoperitoneum device is operated. Accordingly, pneumoperitoneum gas is supplied into the patient's abdominal cavity via the pneumoperitoneum tube and the first trocar from the pneumoperitoneum device. In this case, it is preferable that the air supply pressure of the pneumoperitoneum gas supplied into the patient's abdominal cavity is adjusted to a range of 8 mmHg to 12 mmHg (1 mmHg is about 133.322 Pa). In addition, the pneumoperitoneum step is not limited to the present example. For example, a pneumoperitoneum needle (not illustrated) may puncture a patient's abdominal wall in advance, and pneumoperitoneum gas may be supplied for pneumoperitoneum.

Additionally, in the pneumoperitoneum step, when the supplied gas supplied into the patient's abdominal cavity begins to leak to the outside, the surgeon ligates and sutures the pneumoperitoneum gas leakage part.

[Endoscope Insertion Step]

Next, an endoscope insertion step is performed (Step S16). In the endoscope insertion step, the surgeon inserts an endoscope (equivalent to the above endoscope 100) into the first trocar while adjusting the fixed position of the endoscope insertion part to the slider (equivalent to the above slider 400) arranged inside the first trocar. In this case, it is preferable that the fixed position of the endoscope insertion part (equivalent to the above endoscope insertion part 102) with respect to the slider is adjusted so that a distal end part thereof protrudes from the first trocar by a predetermined length. Accordingly, the endoscope insertion part is inserted into the patient's abdominal cavity via the first trocar.

[Second Trocar Insertion Step]

Next, a second trocar insertion step is performed (Step S18). In the second trocar insertion step, the surgeon incises the patient's abdominal wall surface by about 7 mm to 8 mm and obtusely inserts the second trocar into the incised part (5 mm trocar) while checking an observation image (endoscope image) obtained by the endoscope inserted into the patient's abdominal cavity via the first trocar in the endoscope insertion step. Specifically, first, the surgeon directs the endoscope to another trocar breakthrough position, and projects an image of the peritoneum on a monitor. Next, the surgeon sends a finger sign of the abdominal wall while viewing the image, and checks the trocar breakthrough position. Thereafter, the surgeon incises the abdominal wall surface corresponding to the checked trocar breakthrough position by about 7 mm to 8 mm. After the incision, the surgeon obtusely inserts the second trocar into the incised part. In this case, the surgeon breaks through the abdominal wall while observing the endoscope image. Accordingly, the second trocar is safely inserted into the patient's abdominal cavity.

[Observation Step]

Next, an observation step is performed (Step S20). In the observation step, main parts are observed after the entire observation is performed. That is, the surgeon moves the endoscope backward to the hand side (rear side), observes the inside of the entire abdominal cavity with the endoscope, and performs checking of dissection and checking of an adhesion situation. Subsequently, the surgeon moves the endoscope forward to an affected part side (front side), and observes the vicinity of a hernia (for example, an inguinal region in the case of an inguinal hernia) with the endoscope.

[Treatment Tool Insertion Step]

Next, a treatment tool insertion step is performed (Step S22). In the treatment tool insertion step, the surgeon or the assistant sequentially inserts predetermined treatment tools into the patient's abdominal cavity via the first and second trocars, respectively.

Specifically, first, the surgeon inserts gripping forceps (5 mm gripping forceps) into the second trocar. The gripping forceps inserted into the second trocar are operated by a surgeon's left hand, and are hereinafter referred to as a surgeon left treatment tool (gripping forceps).

Subsequently, the surgeon inserts scissors forceps (5 mm scissors forceps) into the first trocar as a treatment tool. The treatment tool (equivalent to the above treatment tool 200) inserted into the first trocar is operated by a surgeon's right hand, and is hereinafter referred to as a surgeon right treatment tool. If the surgeon right treatment tool is moved forward and backward with the surgeon's right hand in a state where the surgeon right treatment tool is inserted into the first trocar by an interlocking mechanism (equivalent to the above slider 400) of the above-described first trocar, the endoscope moves forward and backward with a predetermined amount of play together with the surgeon right treatment tool in an interlocking manner with this operation. Accordingly, the endoscope always picks up images of forceps distal ends that enter the first trocar. Therefore, it is possible to operate the surgeon right treatment tool, thereby operating the endoscope simultaneously.

In addition, in the following steps, the treatment tools inserted into the first and second trocars, respectively, are replaced with other treatment tools if necessary, although not particularly clearly described.

[Hernia Peeling Step]

Next, a hernia peeling step is performed (Step S24). In the hernia peeling step, the surgeon peels intestines, which have come out of the patient's abdominal cavity, and returns the intestines to the inside of the abdominal cavity. Specifically, the hernia peeling step is performed according to the following procedure.

First, a peritoneum peeling step around a hernia part is performed. In the peritoneum peeling step, the surgeon peels the peritoneum with the surgeon right treatment tool (scissors forceps) while pulling the peritoneum around the hernia part with the surgeon left treatment tool (gripping forceps).

Next, the surgeon peels an adhered intestine and pulls out the adhered intestine from the hernia part to the abdominal cavity side while pulling the intestines, which have come out into the abdominal cavity from the hernia part, with the surgeon left treatment tool (gripping forceps). If the adhered intestine can be quickly peeled, the intestines besides the abdominal cavity are further pulled out and are all returned to the inside of the abdominal cavity. Specifically, first, the scissors forceps are extracted from the first trocar, and the gripping forceps are inserted into the first trocar. Since the first trocar is fixed to the abdominal wall via the outer port, the surgeon can extract the scissors forceps with one hand similar to a normal trocar, and can insert the gripping forceps into the first trocar with one hand. Next, the intestines are alternately gripped with the surgeon right treatment tool (gripping forceps) and the surgeon left treatment tool (gripping forceps), and the intestines are pulled back into the abdominal cavity.

Here, when the intestines are gripped with the surgeon right treatment tool, the gripped intestines may block a field of view and the intestines may not be easily gripped with the surgeon left treatment tool. In such a case, after the intestines gripped with the surgeon right treatment tool are released and a field of view is secured, the intestines are gripped with the surgeon left treatment tool. Alternatively, the intestines can be easily gripped with the surgeon left treatment tool even in a state where a wider field of view is secured by increasing the relative distance of the surgeon right treatment tool and the endoscope and the intestines are gripped with the surgeon right treatment tool.

Since all treatment, such as transfer of the intestines using the surgeon left treatment tool and the surgeon right treatment tool (that is, the left and right gripping forceps), becomes a closed procedure performed by one surgeon (there is no cooperation with the assistant), the treatment becomes smooth without stress.

[Hernia Mesh Pasting Step]

Next, a hernia mesh pasting step is performed (Step S26). In the hernia mesh pasting step, a hernia mesh is put into an abdominal cavity. Specifically, the hernia mesh pasting step is performed as follows.

(1) The surgeon right treatment tool (gripping forceps) is extracted from the first trocar.

(2) The first trocar is extracted from the outer port.

(3) A hernia mesh is folded so as to enter the outer port, and is put into the outer port.

(4) The first trocar is inserted into the outer port again, and the hernia mesh is pushed into the abdominal cavity while checking the hernia mesh with the endoscope image.

Next, the hernia mesh is pasted on the hernia part. Specifically, the hernia mesh pasting step is performed as follows.

(1) The surgeon right treatment tool (gripping forceps) is inserted into the first trocar again, and the hernia mesh is deployed using the surgeon left treatment tool and the surgeon right treatment tool (that is, the left and right gripping forceps) and is arranged in the hernia part.

(2) The surgeon right treatment tool is extracted from the first trocar, and a tacker (or clip) for pasting the hernia mesh on the abdominal wall is inserted into the first trocar.

(3) The hernia mesh is fixed to the abdominal wall with a tacker, avoiding blood vessels, a spermatic cord (in the case of an inguinal hernia), and the like. A hernia mesh outer edge is fixed once around so that the hernia mesh is not peeled.

Here, if the tacker is pressed against the abdominal wall when the angle between the abdominal wall and the tacker (clip) is small, the front of the endoscope may be covered with the abdominal wall, and a place to be tacked may not be able to be checked with the endoscope. In such a case, by changing the relative positions between the tacker and the endoscope (for example, projecting the tacker in an upper right direction on the endoscope), the relative distance between the tacker and the endoscope is increased and the place to be tacked is easily checked with the endoscope.

In addition, in the respective steps, the surgeon wipes the endoscope and cleans the distal end thereof when the endoscope is soiled and fog is generated. Additionally, the endoscope may be soaked in hot water or may be coated with a defogger.

Next, the peeled peritoneum is again pasted on the abdominal wall with the tacker, and it is checked that the peritoneum is not peeled with the endoscope. Moreover, the inside of the entire abdominal cavity is observed, and it is checked that there is no damage to the other internal organs.

The hernia mesh pasting step is completed as described above.

[Extraction Step]

Next, as an extraction step, the endoscope, the treatment tool, and the first and second trocars are extracted according to a predetermined order (Step S28).

[Post-Treatment Step]

Next, as a post-treatment step, the surgeon and the assistant ligate and suture one place of the incised part, and arrange a drain in the one place of the incised part (Step S30). Additionally, a pore part may be closed with an adhesive.

Thereafter, after predetermined work (clearing-up or the like) has been performed, the laparoscopic hernia reparative surgery is completed.

As described above, according to the laparoscopic hernia reparative surgery using the endoscopic surgical device 10 of the present embodiment, the first trocar can be reliably and easily fixed to the body wall by inserting the first trocar into the body wall in a state where the first trocar is inserted into the outer wall. Thus, excellent operability can be assured. Additionally, in the laparoscopic hernia reparative surgery, it is possible to use the outer port as an inlet for introducing the hernia mesh into the body cavity.

(Laparoscopic Gallbladder Removal Surgery)

Next, laparoscopic gallbladder removal surgery will be described as a second example of the endoscopic surgery.

In the laparoscopic gallbladder removal surgery using the endoscopic surgical device 10 of the present embodiment, holes (ports) for allowing the endoscope and the treatment tool to be inserted into the abdominal cavity therethrough are formed in three places in the patient's abdomen. That is, in the present embodiment, the endoscope (equivalent to the above endoscope 100) and the treatment tool (equivalent to the above treatment tool 200) are inserted into the body cavity via the overtube (the first trocar equivalent to the above overtube 300) from the same port. Therefore, the number of ports is smaller by one compared to related-art multi-port (multi-hole type) laparoscopic gallbladder removal surgery.

Figure 41:
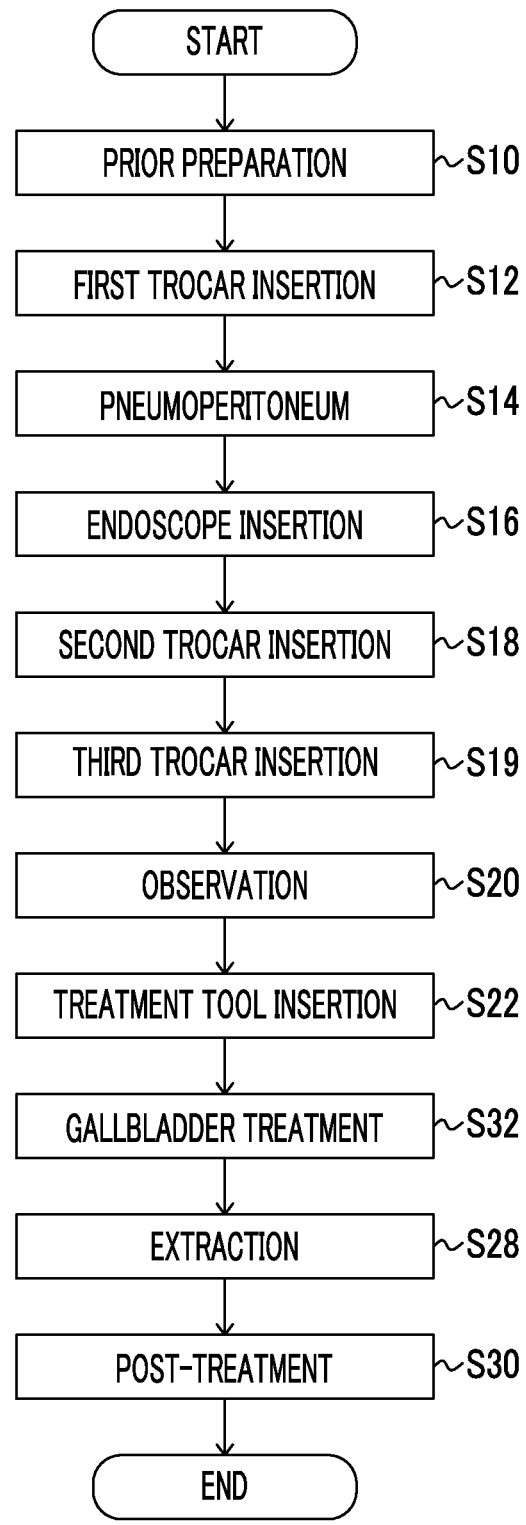
FIG. 41 is a view illustrating the procedure of laparoscopic gallbladder removal surgery.

FIG. 41 is a view illustrating a procedure of the laparoscopic gallbladder removal surgery. In FIG. 41, the same reference signs will be given to the same steps as those of FIG. 40, and the description thereof will be omitted or simply described. Hereinafter, the procedure of the laparoscopic gallbladder removal surgery will be described, referring to FIG. 41.

First, as illustrated in FIG. 41, similar to the laparoscopic hernia reparative surgery, the respective steps from Step S10 to Step S22, that is, the prior preparation step, the first trocar insertion step, the pneumoperitoneum step, the endoscope insertion step, the second trocar insertion step, a third trocar insertion step, the observation step, and the treatment tool insertion step are sequentially performed.

In addition, in the first trocar insertion step (Step S12), similar to the laparoscopic hernia reparative surgery, not only an aspect in which the first trocar and the outer port are integrally inserted into the skin-incised part but also an aspect in which the first trocar is independently inserted into the skin-incised part without using the outer port can be adopted.

Additionally, between the second trocar insertion step (Step S18) and the observation step (Step S20), the third trocar insertion step is performed similar to the second trocar insertion step (Step S19).

Additionally, in the observation step (Step S20), when the main parts are observed after the entire observation has been performed, the surgeon moves the endoscope forward to an affected part side (front side), and observes the gallbladder and the vicinity of the liver with the endoscope.

Additionally, in the treatment tool insertion step (Step S22), the surgeon inserts the gripping forceps (5 mm gripping forceps) into the second trocar as the surgeon left treatment tool, and subsequently inserts the gripping forceps (5 mm gripping forceps) into the first trocar as the surgeon right treatment tool. Subsequently, the assistant inserts the gripping forceps (5 mm gripping forceps) into a third trocar as an assistant treatment tool.

[Gallbladder Treatment Step]

Next, a gallbladder treatment step is performed (Step S32). In the gallbladder treatment step, the surgeon peels and removes the gallbladder from the inside of the patient's abdominal cavity. Specifically, the gallbladder treatment step is performed according to a procedure illustrated in FIG. 42.

Figure 42:
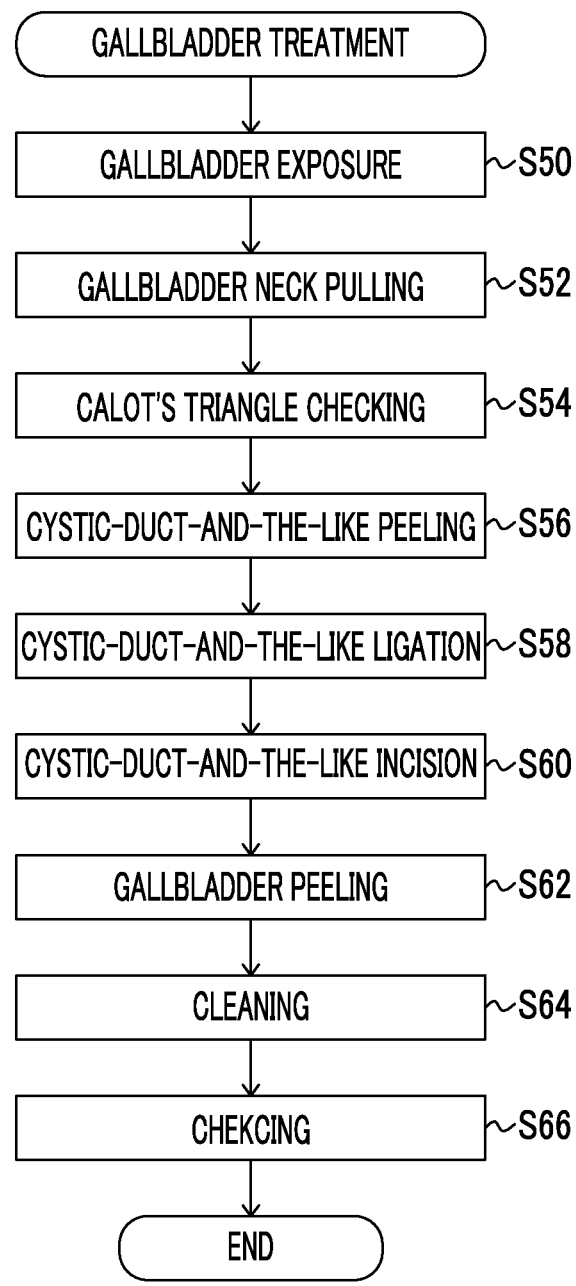
FIG. 42 is a view illustrating a procedure of a gallbladder treatment step.

That is, as illustrated in FIG. 42, first, a gallbladder exposure step is performed (Step S50). In the gallbladder exposure step, when the surgeon holds and pulls the neck of the gallbladder with the surgeon left treatment tool (gripping forceps) and the surgeon right treatment tool (gripping forceps), the gallbladder is exposed. In addition, specifically, the gallbladder exposure step is performed according to the following procedure.

(1) The surgeon operates the surgeon right treatment tool and picks up an image of the entire liver.

(2) The surgeon raises the gallbladder with a belly part of the surgeon left treatment tool (grips and raises the gallbladder if it can be gripped).

(3) The surgeon grips and lifts the neck of the gallbladder with the surgeon right treatment tool.

(4) The surgeon re-gips the bottom of the gallbladder and the neck of the gallbladder with the surgeon left treatment tool.

(5) The surgeon moves the surgeon right treatment tool backward to the hand side (rear side), and observes the inside of the entire abdominal cavity with the endoscope.

In addition, in the present embodiment, the observation range (image pick-up range) of the endoscope may become smaller than that of the multi-port laparoscopic surgery. When it is desired to see an entire image in that case, the internal organs may be switched from one hand to the other hand again. Meanwhile, if the surgeon moves a treatment tool forward and backward, the endoscope moves forward and backward in an interlocking manner with this movement. Therefore, the visual field of the endoscope can be changed without asking for an assistant's help. Additionally, since the surgeon can operate the treatment tool while always grasping a surrounding situation, stress is not placed on the switching work itself of the affected part (treatment part).

Next, as a gallbladder neck pulling step, the assistant grips and pulls the neck of the gallbladder with the assistant treatment tool (gripping forceps) (Step S52).

Next, as a Calot's triangle checking step, the surgeon visually checks the Calot's triangle with the endoscope, and sets a surgical field (Step S54). In this case, an adjustment is made by the treatment tool (gripping forceps) that is pulling the gallbladder and the liver so that the Calot's triangle appears.

Next, as a cystic-duct-and-the-like peeling step, the surgeon operates the surgeon left treatment tool (5 mm gripping forceps) with the left hand, and operates the surgeon right treatment tool (5 mm peeling forceps) with the right hand, and peels a cystic duct, a cystic artery, and a cystic vein (Step S56). In this case, since the peeling operation is a small operation, stroke falls within the play of the interlocking mechanism of the first trocar, and the endoscope does not interlock. Therefore, at the time of the peeling operation, a stable visual field is obtained and treatment becomes easy. Due to this peeling operation, three ducts are isolated from the liver by about 15 mm. In addition, specifically, the cystic-duct-and-the-like peeling step is performed according to the following procedure.

(1) The surgeon grips the cystic duct and the cystic artery and vein with the surgeon left treatment tool.

(2) The surgeon applies a large counter traction to the surgeon left side with the surgeon left treatment tool.

(3) The surgeon brings the surgeon right treatment tool close to the cystic duct and the cystic artery and vein. In this case, in an observation image of the endoscope, the cystic duct and the cystic artery and the cystic vein are gradually magnified in conformity with the forward movement of the surgeon right treatment tool.

(4) The surgeon performs peeling with the surgeon right treatment tool. In this case, since the pulling performed by the assistant is effective compared to single-port (single-hole type) laparoscopic surgery, the peeling can be easily performed. Additionally, the surgeon checks whether an internal organ is penetrated with the surgeon right treatment tool during the peeling.

In addition, in the cystic-duct-and-the-like peeling step, when the cystic duct, the cystic artery, and the cystic vein are bleeding at the time of the peeling thereof, the surgeon performs energization hemostasis or pressure hemostasis with gauze, and performs cleaning using a water supply suction pipe. Additionally, the surgeon wipes the endoscope and cleans the distal end thereof when the endoscope is soiled and fog is generated. Additionally, the endoscope may be soaked in hot water or may be coated with a defogger.

Next, as a cystic-duct-and-the-like ligation step, the surgeon ligates the cystic duct, the cystic artery, and the cystic vein in three places (one place on a removed organ side and two places on the body side) with 5 mm clips (Step S58). As treatment tools to be used in this case, the surgeon left treatment tool is 5 mm gripping forceps, and the surgeon right treatment tool is 5 mm clips.

Next, as a cystic-duct-and-the-like incision step, the surgeon incises the cystic duct, the cystic artery, and the cystic vein while performing mono-polar energization to the cystic duct, the cystic artery, and the cystic vein with the surgeon right treatment tool (5 mm scissors forceps) (Step S60). In this case, the incision is performed between clips in one place on the removed organ side and two places on the body side.

Next, as a gallbladder peeling step, the surgeon peels the gallbladder with the 5 mm peeling forceps (Step S62). In this case, the peeling proceeds from the bottom of the gallbladder to the neck thereof. Additionally, as treatment tools to be used in this case, the surgeon left treatment tool is 5 mm gripping forceps, and the surgeon right treatment tool is 5 mm peeling forceps. In addition, specifically, the cystic-duct-and-the-like incision step is performed according to the following procedure.

(1) The surgeon applies counter traction to an upper part with the surgeon left treatment tool.

(2) The endoscope is brought close to a peeling surface before the surgeon performs peeling with the surgeon right treatment tool. In this case, although the visual field of the endoscope becomes narrow, this is effective because a place to be peeled is followed. That is, operation is simple. Additionally, the relative positions of the endoscope and the surgeon right treatment tool can be changed as desired by the surgeon, and the setting adapted to the procedure of the surgeon is allowed.

(3) The surgeon performs energization removal while gripping the peeling surface with the surgeon right treatment tool. In addition, when the surgeon changes a gripping portion of the surgeon left treatment tool, the change is made while the gallbladder is held down with the surgeon right treatment tool.

(4) The peeling of the gallbladder is completed by repeating the above.

In addition, in the gallbladder peeling step, when the gallbladder is bleeding at the time of the peeling, the surgeon performs energization hemostasis or pressure hemostasis with gauze, and performs cleaning using the water supply suction pipe. In addition, the surgeon wipes the endoscope and cleans the distal end thereof when the endoscope is soiled and fog is generated. Additionally, the endoscope may be soaked in hot water or may be coated with a defogger.

Next, as a cleaning step, the surgeon cleans a liver-isolated portion with the water supply suction pipe after the isolation of the gallbladder (Step S64).

Next, as a checking step, the surgeon observes the liver-isolated portion with the endoscope, and performs checking about the presence/absence of bleeding, bile leakage, the presence/absence of liver damage, and the like, the inside of the entire abdominal cavity is further observed, and it is checked that there is no other internal organ damage (Step S66).

The gallbladder treatment step is completed as described above.

[Extraction Step]

Next, as an extraction step, the endoscope, the treatment tool, and the first to third trocars are extracted according to a predetermined order (Step S28). In this case, the surgeon grips the gallbladder with the treatment tool, and removes the gallbladder to the outside of the body when the trocars are extracted.

[Post-Treatment Step]

Next, as a post-treatment step, the surgeon and the assistant ligate and suture two places of an incised part, and arrange a drain in one place of the incised part (Step S30). Additionally, a pore part may be closed with an adhesive.

Thereafter, after predetermined work (clearing-up or the like) has been performed, the laparoscopic gallbladder removal surgery is completed.

(Laparoscopic Kidney Removal Surgery)

Next, laparoscopic kidney removal surgery will be described as a third example of the endoscopic surgery.

In the laparoscopic kidney removal surgery using the endoscopic surgical device 10 of the present embodiment, holes (ports) for allowing the endoscope and the treatment tool to be inserted into the abdominal cavity therethrough are formed in three places in the patient's abdomen. That is, in the present embodiment, the endoscope (equivalent to the above endoscope 100) and the treatment tool (equivalent to the above treatment tool 200) are inserted into the body cavity via the overtube (the first trocar equivalent to the above overtube 300) from the same port. Therefore, the number of ports is smaller by one compared to related-art multi-port (multi-hole type) laparoscopic kidney removal surgery.

Figure 43:
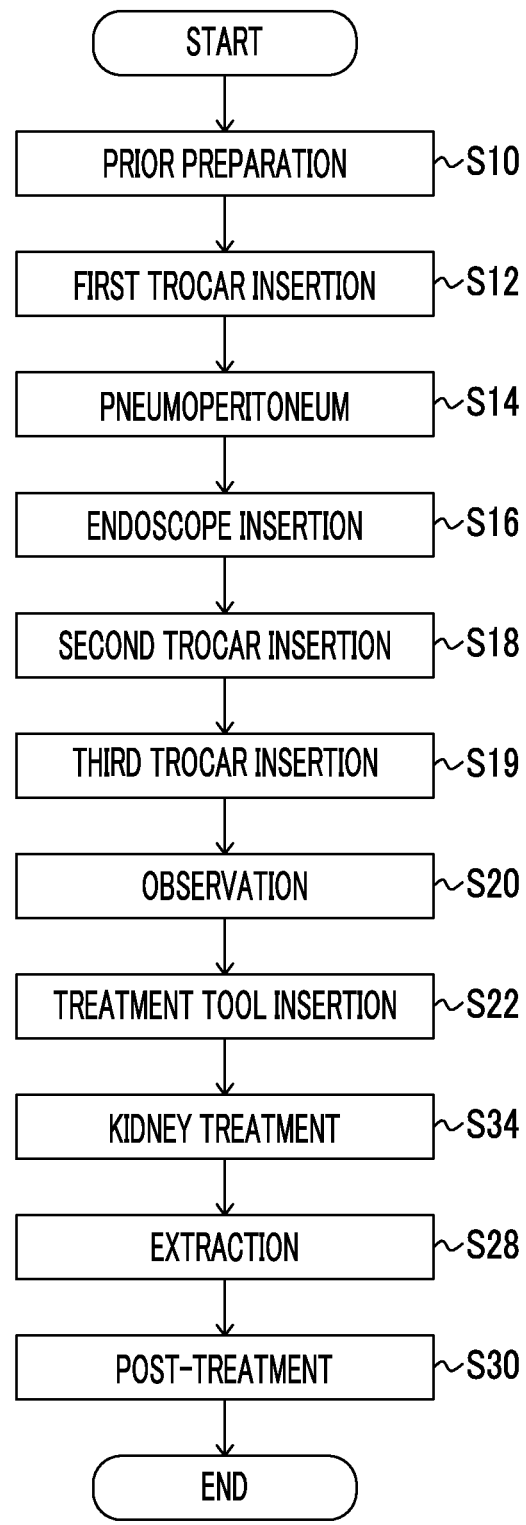
FIG. 43 is a view illustrating a procedure of laparoscopic kidney removal surgery.

FIG. 43 is a view illustrating a procedure of the laparoscopic kidney removal surgery. In FIG. 43, the same reference signs will be given to the same steps as those of FIG. 40 or 41, and the description thereof will be omitted or simply described.

First, as illustrated in FIG. 43, similar to the laparoscopic gallbladder removal surgery, the respective steps from Step S10 to Step S22, that is, the prior preparation step, the first trocar insertion step, the pneumoperitoneum step, the endoscope insertion step, the second trocar insertion step, the third trocar insertion step, the observation step, and the treatment tool insertion step are sequentially performed.

In addition, in the observation step (Step S22), when the main parts are observed after the entire observation has been performed, the surgeon moves the endoscope forward to an affected part side (front side), and observes a certain retroperitoneum of the kidney with the endoscope.

[Kidney Treatment Step]

Next, a kidney treatment step is performed (Step S34). In the kidney treatment step, the surgeon peels the retroperitoneum from the inside of the patient's abdominal cavity and peels and removes the kidney. Specifically, the kidney treatment step is performed according to a procedure illustrated in FIG. 44.

Figure 44:
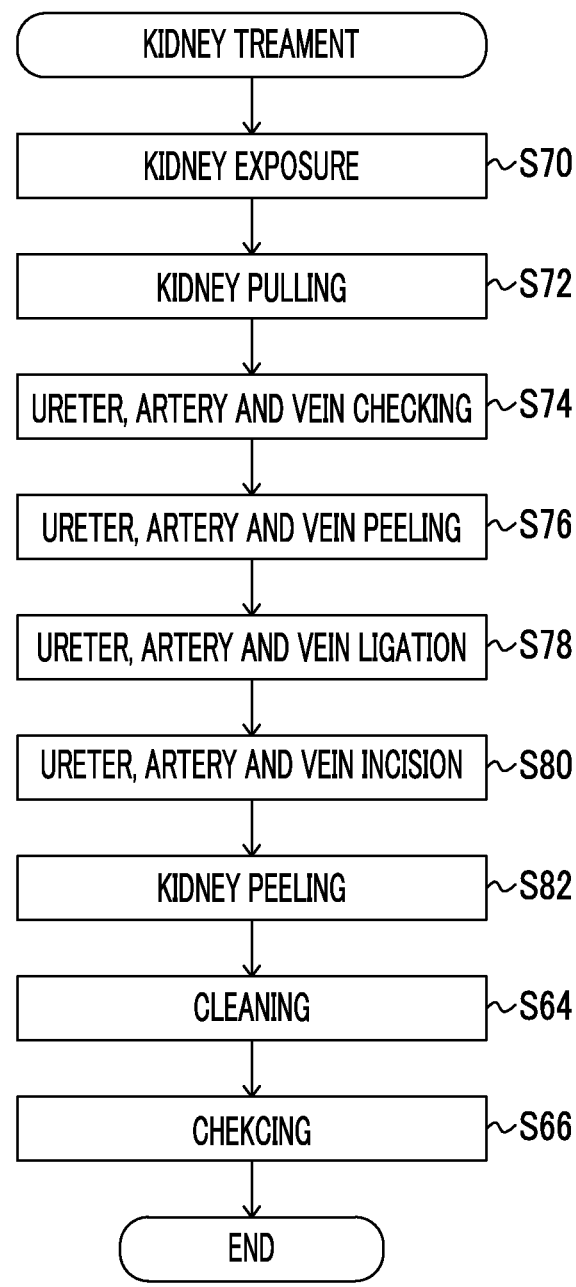
FIG. 44 is a view illustrating a procedure of a kidney treatment step.

That is, as illustrated in FIG. 44, first, a kidney exposure step is performed (Step S70). In the kidney exposure step, the surgeon peels the retroperitoneum with the surgeon left treatment tool (gripping forceps) and the surgeon right treatment tool (peeling forceps), and exposes the kidney. In addition, specifically, the kidney exposure step is performed according to the following procedure.

(1) The surgeon operates the surgeon right treatment tool and picks up an image at the position of the kidney.

(2) The surgeon grips the retroperitoneum with the surgeon left treatment tool.

(3) The surgeon peels the retroperitoneum with the surgeon right treatment tool. In this case, a monopolar electrode treatment tool, a bipolar electrode treatment tool, or an ultrasonic incision treatment tool may be used.

(4) The assistant pulls the peeled kidney.

(5) The surgeon performs the above treatment and exposes the entire kidney, a kidney artery, a kidney vein, and a ureter.

In addition, in the present embodiment, the observation range (image pick-up range) of the endoscope may become smaller than that of the multi-port laparoscopic surgery. When it is desired to see an entire image, in that case, the internal organs may be switched from one hand to the other hand again. Meanwhile, if the surgeon moves a treatment tool forward and backward, the endoscope moves forward and backward in an interlocking manner with this movement. Therefore, the visual field of the endoscope can be changed without asking for an assistant's help. Additionally, since the surgeon can operate the treatment tool while always grasping a surrounding situation, stress is not placed on the switching work itself of the affected part (treatment part).

Next, as a kidney pulling step, the assistant pulls the kidney with the assistant treatment tool (gripping forceps) (Step S72).

Next, as a ureter, artery and vein checking step, the surgeon visually checks the ureter, the artery, and the vein on a main artery side with the endoscope, and sets a surgical field (Step S74). In this case, an adjustment is made by the treatment tool (gripping forceps) that is pulling the kidney so that the ureter, the artery, and the vein appear. If necessary, the small intestine is moved by the treatment tool (gripping forceps) so as to be out of the surgical field.

Next, as a ureter, artery and vein peeling step, the surgeon operates the surgeon left treatment tool (5 mm gripping forceps) with the left hand, and operates the surgeon right treatment tool (5 mm peeling forceps) with the right hand, and peels a ureter, a kidney artery, and a kidney vein (Step S76). In this case, since the peeling operation is a small operation, stroke thereof falls within the play of the interlocking mechanism of the first trocar, and the endoscope does not interlock. Therefore, at the time of the peeling operation, a stable visual field is obtained and treatment becomes easy. Due to this peeling operation, three ducts are isolated by about 15 mm. In addition, specifically, the ureter, artery and vein peeling step is performed according to the following procedure.

(1) The surgeon grips the ureter and the kidney artery and vein with the surgeon left treatment tool.

(2) The surgeon applies a large counter traction to the surgeon left side with the surgeon left treatment tool.

(3) The surgeon brings the surgeon right treatment tool close to the ureter and the kidney artery and vein. In this case, in an observation image of the endoscope, the ureter and the kidney artery and vein are gradually magnified in conformity with the forward movement of the surgeon right treatment tool.

(4) The surgeon performs peeling with the surgeon right treatment tool. In this case, since the pulling performed by the assistant is effective compared to the single-port (single-hole type) laparoscopic surgery, the peeling can be easily performed. Additionally, the surgeon checks whether an internal organ is penetrated with the surgeon right treatment tool during the peeling.

In addition, in the ureter, artery and vein peeling step, when the ureter, the kidney artery, and the kidney vein are bleeding at the time of the peeling thereof, the surgeon performs energization hemostasis or pressure hemostasis with gauze, and performs cleaning using the water supply suction pipe. In addition, the surgeon wipes the endoscope and cleans the distal end thereof when the endoscope is soiled and fog is generated. Additionally, the endoscope may be soaked in hot water or may be coated with a defogger.

Next, as a ureter, artery and vein ligation step, the surgeon ligates the ureter, the kidney artery, and the kidney vein in three places (one place on the removed organ side and two places on the body side) for each with 5 mm clips (Step S78). As treatment tools to be used in this case, the surgeon left treatment tool is 5 mm gripping forceps, and the surgeon right treatment tool is 5 mm clips. In this case, the ligation is performed from the artery.

Next, as a ureter, artery and vein incision step, the surgeon incises the ureter, the kidney artery, and the kidney vein while performing mono-polar energization to the ureter, the kidney artery, and the kidney vein with the surgeon right treatment tool (5 mm scissors forceps) (Step S80). In this case, the incision is performed between clips in one place on the removed organ side and two places on the body side.

Next, as a kidney peeling step, the surgeon peels the kidney with the 5 mm peeling forceps (Step S62). As treatment tools to be used in this case, the surgeon left treatment tool is 5 mm gripping forceps, and the surgeon right treatment tool is 5 mm peeling forceps. In addition, specifically, the kidney peeling step is performed according to the following procedure.

(1) The surgeon applies counter traction to an upper part with the surgeon left treatment tool.

(2) The endoscope is brought close to a peeling surface before the surgeon performs peeling with the surgeon right treatment tool. In this case, although the visual field of the endoscope becomes narrow, this is effective because a place to be peeled is followed. That is, operation is simple. Additionally, the relative positions of the endoscope and the surgeon right treatment tool can be changed as desired by the surgeon, and the setting adapted to the procedure of the surgeon is allowed.

(3) The surgeon performs energization removal while gripping the peeling surface with the surgeon right treatment tool. In addition, when the surgeon changes a gripping portion of the surgeon left treatment tool, the change is made while the kidney is held down with the surgeon right treatment tool.

(4) The peeling of the kidney is completed by repeating the above.

In addition, in the kidney peeling step, when the kidney is bleeding at the time of the peeling, the surgeon performs energization hemostasis or pressure hemostasis with gauze, and performs cleaning using the water supply suction pipe. In addition, the surgeon wipes the endoscope and cleans the distal end thereof when the endoscope is soiled and fog is generated. Additionally, the endoscope may be soaked in hot water or may be coated with a defogger.

Next, as a cleaning step, the surgeon cleans an isolated portion with the water supply suction pipe after the isolation of the kidney (Step S64).

Next, as a checking step, the surgeon observes the isolated portion with the endoscope, and performs checking about the presence/absence of bleeding, the presence/absence of tissue damage, and the like, the inside of the entire abdominal cavity is further observed, and it is checked that there is no other internal organ damage (Step S66).

The kidney treatment step is completed as described above.

[Extraction Step]

Next, as an extraction step, the endoscope, the treatment tool, and the first to third trocars are extracted according to a predetermined order (Step S28). In this case, the surgeon grips the kidney with the treatment tool, and removes the kidney to the outside of the body when the trocars are extracted. In this case, a pouch may be used. Additionally, in order to take out the kidney, the skin may be additionally incised.

[Post-Treatment Step]

Next, as a post-treatment step, the surgeon and the assistant ligate and suture two places of an incised part, and arrange a drain in one place of the incised part (Step S30). Additionally, a pore part may be closed with an adhesive.

Thereafter, after predetermined work (clearing-up or the like) has been performed, the laparoscopic kidney removal surgery is completed.

(Laparoscopic Uterus and Ovary Removal Surgery)

Next, laparoscopic uterus and ovary removal surgery will be described as a fourth example of the endoscopic surgery.

In the laparoscopic uterus and ovary removal surgery using the endoscopic surgical device 10 of the present embodiment, similar to the above-described laparoscopic gallbladder removal surgery and laparoscopic kidney removal surgery, holes (ports) for allowing the endoscope and the treatment tool to be inserted into the abdominal cavity therethrough are formed in three places in the patient's abdomen. That is, in the present embodiment, the endoscope (equivalent to the above endoscope 100) and the treatment tool (equivalent to the above treatment tool 200) are inserted into the body cavity via the overtube (the first trocar equivalent to the above overtube 300) from the same port. Therefore, the number of ports is smaller by one compared to the related-art multi-port (multi-hole type) laparoscopic surgery.

Next, a procedure of the laparoscopic uterus and ovary removal surgery will be described.

First, in the laparoscopic uterus and ovary removal surgery, similar to the laparoscopic gallbladder removal surgery, the prior preparation step, the first trocar insertion step, the pneumoperitoneum step, the second trocar insertion step, the third trocar insertion step, the observation step, and the treatment tool insertion step are sequentially performed (refer to FIG. 41).

In addition, in the observation step, when the main parts are observed after the entire observation has been performed, the surgeon moves the endoscope forward to an affected part side (front side), and observes the vicinity of the uterus with the endoscope.

Additionally, in the treatment tool insertion step, the surgeon inserts the bipolar forceps (5 mm bipolar forceps) into the second trocar as the surgeon left treatment tool, and subsequently inserts the scissors forceps (5 mm scissors forceps) into the first trocar as the surgeon right treatment tool. Subsequently, the assistant inserts the gripping forceps (5 mm gripping forceps) into the third trocar as the assistant treatment tool.

[Uterus Isolation Step]

Next, a uterus isolation step is performed. In the uterus isolation step, the surgeon isolates a patient's uterus from a round ligament of the uterus, a broad ligament of the uterus, and a suspensory ligament of the ovary. Specifically, the uterus isolation step is performed according to the following procedure.

First, a round-ligament-of-uterus cutting step is performed. Specifically, the round-ligament-of-uterus cutting step is performed according to the following procedure.

(1) The surgeon picks up an image of the left side of the uterus.

(2) The assistant grips the vicinity of the uterus in a left round ligament of the uterus with the assistant treatment tool (gripping forceps), and pulls the vicinity of the uterus to the right side.

(3) The surgeon performs bipolar energization to the round ligament of the uterus with the surgeon right treatment tool (scissors forceps), coagulates the round ligament of the uterus, and then cuts the round ligament of the uterus.

Next, a broad-ligament-of-uterus incision step is performed. Specifically, the broad-ligament-of-uterus incision step is performed according to the following procedure.

(1) The surgeon incises the broad ligament of the uterus while performing bipolar energization to the broad ligament of the uterus on a patient's front side with the surgeon right treatment tool (scissors forceps) up to a vaginal part (in front of a uterine artery).

(2) The surgeon incises the broad ligament of the uterus while performing bipolar energization to the broad ligament of the uterus on a patient's rear side with the surgeon right treatment tool (scissors forceps) up to the vaginal part (in front of the uterine artery).

(3) The surgeon incises the broad ligament of the uterus while performing bipolar energization to the broad ligament of the uterus on a patient's front side with the surgeon right treatment tool (scissors forceps) up to the suspensory ligament of the ovary.

(4) The surgeon incises the broad ligament of the uterus while performing bipolar energization to the broad ligament of the uterus on the patient's rear side with the surgeon right treatment tool (scissors forceps) up to the suspensory ligament of the ovary.

In addition, since the surgeon right treatment tool (scissors forceps) is part of a main procedure and the endoscope always follows the surgeon right treatment tool, the surgeon can perform a procedure smoothly without stress.

Next, a suspensory-ligament-of-ovary cutting step is performed. Specifically, the suspensory-ligament-of-ovary cutting step is performed according to the following procedure.

(1) The assistant grips the vicinity of the ovary of the suspensory ligament of the ovary with the assistant treatment tool (gripping forceps), and pulls the vicinity of the uterus to the right side.

(2) The surgeon performs bipolar energization to the suspensory ligament of the ovary with the surgeon right treatment tool (scissors forceps) near the ovary, coagulates the suspensory ligament of the ovary, and then cuts the suspensory ligament of the ovary.

In addition, the surgeon wipes the endoscope and cleans the distal end thereof when the endoscope is soiled and fog is generated. Additionally, the endoscope may be soaked in hot water or may be coated with a defogger.

Next, also on the right side of the uterus, the round-ligament-of-uterus cutting step, the broad-ligament-of-uterus incision step, and the suspensory-ligament-of-ovary cutting step are similarly performed.

Next, a bladder peeling step is performed. Specifically, the bladder peeling step is performed according to the following procedure.

(1) The assistant pulls the bladder upward with the assistant treatment tool (gripping forceps).

(2) The surgeon isolates the bladder and the uterus, using the surgeon right treatment tool (bipolar forceps) and the surgeon left treatment tool (gripping forceps).

In addition, since the peeling is performed by the cooperation of the surgeon left treatment tool and the surgeon right treatment tool, the surgeon left treatment tool may deviate from the surgical field. Meanwhile, since a closed procedure is performed by one surgeon (there is no cooperation with the assistant), the surgeon can perform a procedure smoothly without stress.

[Uterus Cutting Step]

Next, a uterus cutting step is performed. In a uterus cutting step, the uterine artery is coagulated and cut, and the uterus is cut off from a vagina. In addition, the uterus cutting step is performed according to the following procedure.

First, a uterine-artery cutting step is performed. Specifically, the uterine-artery cutting step is performed according to the following procedure.

(1) The assistant pulls the uterus to a patient's right side with the assistant treatment tool (gripping forceps), and the surgeon picks up an image of a uterine artery part of a uterus root.

(2) The position of the ureter is checked so that the ureter is not erroneously damaged.

(3) The surgeon coagulates and cuts the uterine artery with the surgeon right treatment tool (bipolar forceps).

(4) The right side of the uterus is similarly treated.

Next, a uterus removal step is performed. Specifically, the uterus removal step is performed according to the following procedure.

(1) The surgeon cuts the vagina from the upper side of the vagina along a guide of a manipulator for a uterus with the surgeon left treatment tool (hook forceps).

(2) The surgeon appropriately stops bleeding with the surgeon right treatment tool (peeling forceps).

(3) The assistant pulls the uterus rightward with the assistant treatment tool (gripping forceps), and the surgeon cuts the left side (about 180°) of the vagina with the surgeon left treatment tool (hook forceps).

(4) The right side of the vagina is similarly treated.

(5) Since the uterus cannot be pulled to the left side, the surgeon cuts the right side of the vagina with the surgeon right treatment tool (hook forceps) while holding down the uterus on the left side with the belly part of the surgeon left treatment tool (peeling forceps).

(6) The assistant takes out the uterus from the vagina to the outside of the body together with the manipulator for a uterus.

In addition, in the uterus removal step, when there is bleeding, the surgeon performs energization hemostasis or pressure hemostasis with gauze, and performs cleaning using the water supply suction pipe. In addition, the surgeon wipes the endoscope and cleans the distal end thereof when the endoscope is soiled and fog is generated. Additionally, the endoscope may be soaked in hot water or may be coated with a defogger.

Next, the vagina suturing step is performed. Specifically, the vagina suturing step is performed according to the following procedure.

(1) The surgeon sutures a mucous membrane of the vagina.

(2) The surgeon sutures the peritoneum and a sacral uterine ligament.

The uterus removal step is completed as described above.

[Extraction Step]

Next, as an extraction step, the endoscope, the treatment tool, and the first to third trocars are extracted according to a predetermined order.

[Post-Treatment Step]

Next, as a post-treatment step, the surgeon and the assistant ligate and suture two places of an incised part, and arrange a drain in one place of the incised part. Additionally, a pore part may be closed with an adhesive.

Thereafter, after predetermined work (clearing-up or the like) has been performed, the laparoscopic uterus and ovary removal surgery is completed.

(Laparoscopic Appendix Removal Surgery)

Next, laparoscopic appendix removal surgery will be described as a fifth example of the endoscopic surgery.

In the laparoscopic appendix removal surgery using the endoscopic surgical device 10 of the present embodiment, holes (ports) for allowing the endoscope and the treatment tool to be inserted into the abdominal cavity therethrough are formed in two places in the patient's abdomen. That is, in the present embodiment, the endoscope (equivalent to the above endoscope 100) and the treatment tool (equivalent to the above treatment tool 200) are inserted into the body cavity via the overtube (the first trocar equivalent to the above overtube 300) from the same port. Therefore, the number of ports is smaller by one compared to related-art multi-port (multi-hole type) laparoscopic appendix surgery.

First, in the laparoscopic appendix removal surgery, similar to the laparoscopic hernia reparative surgery, the prior preparation step, the first trocar insertion step, the pneumoperitoneum step, the second trocar insertion step, the observation step, and the treatment tool insertion step are sequentially performed (refer to FIG. 40). In the laparoscopic appendix removal surgery, the number of ports is two as described above. Therefore, the third trocar insertion step as in the laparoscopic gallbladder removal surgery is not performed.

In addition, in the observation step, when the main parts are observed after the entire observation has been performed, the surgeon moves the endoscope forward to an affected part side (front side), and observes the vicinity of the appendix with the endoscope.

Additionally, in the treatment tool insertion step, the surgeon inserts the gripping forceps (5 mm gripping forceps) into the second trocar as the surgeon left treatment tool, and subsequently inserts the gripping forceps (5 mm gripping forceps) into the first trocar as the surgeon right treatment tool.

[Appendix Peeling Step]

Next, an appendix peeling step is performed. In the appendix peeling step, the surgeon peels a patient's appendix from a mesoappendix. Specifically, the appendix peeling step is performed according to the following procedure.

First, the surgeon finds an appendix buried in the intestines using the surgeon left treatment tool and the surgeon right treatment tool (that is, the left and right gripping forceps), and lifts the appendix so that treatment is easily performed. Next, after the surgeon right treatment tool has been replaced with peeling forceps from the gripping forceps, the mesoappendix is separated with the surgeon right treatment tool (peeling forceps) while the appendix is lifted with the surgeon left treatment tool (gripping forceps). Here, since a closed procedure is performed by one surgeon (there is no cooperation with the assistant), the treatment of the pulling and the peeling can be smoothly performed without stress.

In addition, the surgeon wipes the endoscope and cleans the distal end thereof when the endoscope is soiled and fog is generated. Additionally, the endoscope may be soaked in hot water or may be coated with a defogger.

[Appendix Removal Step]

Next, appendix removal is performed. Specifically, the appendix removal is performed according to the following procedure.

(1) The appendix is pulled with the surgeon left treatment tool (gripping forceps).

(2) The surgeon ligates the root of the appendix twice.

(3) A side where the appendix is removed is ligated.

(4) The surgeon right treatment tool is replaced with scissors forceps.

(5) The appendix is cut so that the twice ligation side remains inside the body.

The appendix removal step is completed as described above.

[Extraction Step]

Next, as an extraction step, the endoscope, the treatment tool, and the first and second trocars are extracted according to a predetermined order. In this case, the surgeon grips the appendix with the treatment tool, and removes the appendix to the outside of the body when the trocars are extracted.

[Post-Treatment Step]

Next, as a post-treatment step, the surgeon and the assistant ligate and suture one place of an incised part, and arrange a drain in one place of the incised part. Additionally, a pore part may be closed with an adhesive.

Thereafter, after predetermined work (clearing-up or the like) has been performed, the appendix removal surgery is completed.

Although the endoscopic surgical device, the overtube, and the exterior tube related to the invention have been described above in detail, the invention is not limited to the above embodiment, and various improvements and modifications may be made without departing from the scope of the invention.

EXPLANATION OF REFERENCES

10: endoscope surgical device
100: endoscope
102: endoscope insertion part
104: operating part
106: universal cable
108: processor device
110: light source device
112: monitor
114: distal end surface
116: observation window
118: illumination window
120: pneumoperitoneum device
122: air supply tube
200: treatment tool
202: treatment tool insertion part
204: operating part
206: treatment part
208: sheath
210: fixed handle
214: movable handle
300: overtube
300a: reference axis
302: base end surface
304: distal end surface
306: endoscope insertion passage
306a: endoscope insertion axis
308: treatment tool insertion passage
308a: treatment tool insertion axis
310: endoscope insertion opening
312: endoscope delivery opening
314: treatment tool insertion opening
316: treatment tool delivery opening
318: air supply connector
320: overtube body
322: outer wall
324: lumen
340: base end cap
342: through-hole
344: through-hole
346: valve member
348: valve member
350: through-hole
360: distal end cap
362: through-hole
364: through-hole
370: guide groove
372: guide groove
374: guide plate
376: guide plate
400: slider (interlocking member)
402: slider body
404: upper surface
406: lower surface
408: protruding strip
410: protruding strip
420: endoscope-coupled part
422: treatment tool-coupled part
424: through-hole
426: pressure-contact member
428: pressure-contact member attachment part 430: opening
432: through-hole
440: sleeve (sleeve member)
444: sleeve body (frame body)
446: pressure-contact member
448: through-hole
450: through-hole
460: guide part
462: guide surface
464: sleeve housing space
466: end edge part
468: end edge part
470: guide rod
472: guide rod
474: guide hole
476: guide hole
500: inner needle
502: shaft part
504: shaft part
506: distal end part
508: distal end part
510: head part
512: head part body
514: locking lever
520: axis
522: side surface
524: lower surface
526: rear end surface
528: front end surface
532: locking claw
534: locking hole
800: wall surface member
802: transverse groove
804: recess
806: protrusion
807a: first side surface
807b: second side surface
808a: first tapered surface
808b: first tapered surface
810: protrusion
820: transverse groove
822: side surface
824: tapered surface
830: outer port
830a: reference axis
832: insertion hole
840: insertion part
842: base end part
850: outer wall
860: airtight valve
862: slit
870: hole

What is claimed is:

1. An endoscopic surgical device comprising:
an endoscope that observes the inside of a body cavity;
a treatment tool that inspects or treats an affected part within the body cavity; and
an overtube that guides the endoscope and the treatment tool into the body cavity,
wherein the overtube includes
an overtube body that passes through a body wall and is inserted into the body cavity,
a slider member provided in the overtube; and
a sleeve member provided in the overtube;
wherein the slider member has a first stopper and a second stopper which are provided separately from each other in a longitudinal axis direction of the overtube, the sleeve member is slidably located on a first path formed between the first stopper and the second stopper,
the slider member has a first holder part configured to hold the endoscope and a second path through which the endoscope is inserted,
the sleeve member has a third path through which the treatment tool is inserted, and the sleeve member comprises a second holding part configured to hold the treatment tool inserted through the third path,
wherein a contact surface of the overtube body with a body wall includes a rotation-preventing wall surface for preventing rotation in a rotational direction with an axial direction of the overtube body as a center.

2. The endoscopic surgical device according to claim 1, wherein the rotation-preventing wall surface is provided with a first concavo-convex part including a groove part or a projection part that is formed along an axial direction of the overtube body.

3. The endoscopic surgical device according to claim 2, wherein a plurality of the first concavo-convex parts are provided in the rotational direction of the overtube body.

4. The endoscopic surgical device according to claim 3, wherein the plurality of first concavo-convex parts are periodically provided in the rotational direction of the overtube body.

5. The endoscopic surgical device according to claim 2, wherein the rotation-preventing wall surface is provided with a second concavo-convex part including a groove part or a projection part that is formed along the rotational direction of the overtube body.

6. The endoscopic surgical device according to claim 5, wherein a plurality of the second concavo-convex parts are provided in the axial direction of the overtube body.

7. The endoscopic surgical device according to claim 6, wherein the plurality of second concavo-convex parts are periodically provided in the axial direction of the overtube body.

8. The endoscopic surgical device according to claim 5, wherein the second concavo-convex part includes a first locking surface that restricts the movement of the overtube body to a distal end side in the axial direction, and a second locking surface that restricts the movement of the overtube body to a base end side in the axial direction.

9. The endoscopic surgical device according to claim 8, wherein each of the first locking surface and the second locking surface includes a surface including a plane perpendicular to the axial direction of the overtube body.

10. The endoscopic surgical device according to claim 1, wherein a range where the sleeve member is movable forward and backward with respect to the slider member is limited.

11. The endoscopic surgical device according to claim 1, wherein a following formula is satisfied when a fixing force for fixing the first holding part to the endoscope is defined as F1 and a fixing force for the second holding part to the treatment tool is defined as F2, $$F1>F2.$$

12. The endoscopic surgical device according to claim 1, further comprising:
a first valve member that is provided in the second path and secures airtightness within the body cavity; and a second valve member that is provided in the third path and secures airtightness within the body cavity, wherein following formulas are satisfied when a fixing force for fixing the first holding part to the endoscope is defined as F1, a fixing force for fixing the second holding part to the treatment tool is defined as F2, and a frictional force that the endoscope receives from the first valve member when the endoscope moves forward and backward is defined as F3, $$F1 > F3$$

$$F2 > F3.$$

13. An overtube comprising:
an overtube body that passes through a body wall and is inserted into a body cavity;
a slider member provided in the overtube; and
a sleeve member provided in the overtube;
wherein the slider member has a first stopper and a second stopper which are provided separately from each other in a longitudinal axis direction of the overtube,
the sleeve member is slidably located on a first path formed between the first stopper and the second stopper,
the slider member has a first holder part configured to hold the endoscope and a second path through which the endoscope is inserted,
the sleeve member has a third path through which the treatment tool is inserted, and the sleeve member comprises a second holding part configured to hold the treatment tool inserted through the third path,
wherein a contact surface of the overtube body with a body wall includes a rotation-preventing wall surface for preventing rotation in a rotational direction with an axial direction of the overtube body as a center.

14. The overtube according to claim 13,
wherein the rotation-preventing wall surface is provided with a first concavo-convex part including a groove part or a projection part that is formed along an axial direction of the overtube body.

15. The overtube according to claim 14,
wherein a plurality of the first concavo-convex parts are provided in the rotational direction of the overtube body.

16. The overtube according to claim 15,
wherein the plurality of first concavo-convex parts are periodically provided in the rotational direction of the overtube body.

17. The overtube according to claim 14,
wherein the rotation-preventing wall surface is provided with a second concavo-convex part including a groove part or a projection part that is formed along the rotational direction of the overtube body.

18. The overtube according to claim 17,
wherein a plurality of the second concavo-convex parts are provided in the axial direction of the overtube body.

19. The overtube according to claim 18,
wherein the plurality of second concavo-convex parts are periodically provided in the axial direction of the overtube body.

20. The overtube according to claim 17,
wherein the second concavo-convex part includes a first locking surface that restricts the movement of the overtube body to a distal end side in the axial direction, and a second locking surface that restricts the movement of the overtube body to a base end side in the axial direction.

21. The overtube according to claim 20,
wherein each of the first locking surface and the second locking surface includes a surface including a plane perpendicular to the axial direction of the overtube body.

* * * * *